United States Patent
Nicoli et al.

(10) Patent No.: US 7,496,463 B2
(45) Date of Patent: Feb. 24, 2009

(54) SENSORS AND METHODS FOR HIGH-SENSITIVITY OPTICAL PARTICLE COUNTING AND SIZING

(75) Inventors: David F. Nicoli, Goleta, CA (US); Paul Toumbas, Patchogue, NY (US)

(73) Assignee: Agilent Technologies, Inc., Santa Clara, CA (US)

( * ) Notice: Subject to any disclaimer, the term of this patent is extended or adjusted under 35 U.S.C. 154(b) by 127 days.

(21) Appl. No.: 11/518,874

(22) Filed: Sep. 12, 2006

(65) Prior Publication Data

US 2007/0010974 A1 Jan. 11, 2007

Related U.S. Application Data

(62) Division of application No. 10/847,618, filed on May 18, 2004, now Pat. No. 7,127,356, which is a division of application No. 10/196,714, filed on Jul. 17, 2002, now Pat. No. 6,794,671.

(51) Int. Cl.
*G01C 19/00* (2006.01)
(52) U.S. Cl. ...................................... 702/104
(58) Field of Classification Search ................. 702/104; 250/574
See application file for complete search history.

(56) References Cited

U.S. PATENT DOCUMENTS

| | | | |
|---|---|---|---|
| 5,654,797 A | 8/1997 | Moreau et al. | |
| 5,793,478 A | 8/1998 | Rader et al. | |
| 6,417,920 B1 | 7/2002 | Shimaoka | |
| 6,794,671 B2 * | 9/2004 | Nicoli et al. | ................. 250/574 |

OTHER PUBLICATIONS

Holve, Don et al. "Optical Particle Sizing for In Situ Measurements: Part 1 and 2." Applied Optics, vol. 18, No. 10, May 15, 1979, pp. 1632-1652.

* cited by examiner

*Primary Examiner*—Tung S Lau
*Assistant Examiner*—Xiuquin Sun

(57) ABSTRACT

A single-particle optical sensor, which has high sensitivity and responds to relatively concentrated suspensions, uses a relatively narrow light beam to illuminate an optical sensing zone nonuniformly. The zone is smaller than the flow channel so that the sensor responds to only a fraction of the total number of particles flowing through the channel, detecting a statistically significant number of particles of any relevant diameter. Because different particle trajectories flow through different parts of the zone illuminated at different intensities, it is necessary to deconvolute the result. Two methods of deconvolution are used: modified matrix inversion or successive subtraction. Both methods use a few basis vectors measured empirically or computed from a theoretical model, and the remaining basis vectors are derived from these few. The sensor is compensated for turbidity. Several embodiments are disclosed employing light-extinction or light-scattering detection, or both.

4 Claims, 38 Drawing Sheets

FIG. 16A

| | Col 1 | Col 2 | Col 3 | Col 4 | Col 5 | Col 6 | Col 7 | Col 8 | Col 9 | Col 10 | Col 11 | Col 12 | Col 13 | Col 14 | Col 15 | Col 16 |
|---|---|---|---|---|---|---|---|---|---|---|---|---|---|---|---|---|
| Row 1 | 1 | 0.983 | 0.704 | 0.482 | 0.358 | 0.252 | 0.218 | 0.127 | 0.126 | 0.116 | 0.095 | 0.059 | 0.066 | 0.068 | 0.069 | 0.056 |
| Row 2 | 0.264 | 1 | 0.983 | 0.704 | 0.482 | 0.358 | 0.242 | 0.184 | 0.133 | 0.125 | 0.11 | 0.084 | 0.07 | 0.072 | 0.072 | 0.072 |
| Row 3 | 0.053 | 0.264 | 1 | 0.983 | 0.704 | 0.482 | 0.321 | 0.233 | 0.182 | 0.138 | 0.124 | 0.105 | 0.092 | 0.08 | 0.079 | 0.077 |
| Row 4 | 0.041 | 0.053 | 0.264 | 1 | 0.983 | 0.704 | 0.42 | 0.283 | 0.226 | 0.18 | 0.143 | 0.123 | 0.114 | 0.1 | 0.09 | 0.085 |
| Row 5 | 0.026 | 0.041 | 0.053 | 0.264 | 1 | 0.983 | 0.613 | 0.359 | 0.277 | 0.219 | 0.178 | 0.148 | 0.131 | 0.124 | 0.107 | 0.101 |
| Row 6 | 0.006 | 0.026 | 0.041 | 0.053 | 0.264 | 1 | 0.88 | 0.523 | 0.344 | 0.27 | 0.212 | 0.176 | 0.155 | 0.139 | 0.133 | 0.115 |
| Row 7 | 0.003 | 0.006 | 0.026 | 0.041 | 0.053 | 0.264 | 1 | 0.777 | 0.487 | 0.33 | 0.263 | 0.206 | 0.181 | 0.162 | 0.147 | 0.143 |
| Row 8 | 0.001 | 0.003 | 0.006 | 0.026 | 0.041 | 0.053 | 0.271 | 1 | 0.713 | 0.451 | 0.318 | 0.256 | 0.212 | 0.186 | 0.169 | 0.155 |
| Row 9 | 0 | 0.001 | 0.003 | 0.006 | 0.026 | 0.041 | 0.046 | 0.277 | 1 | 0.649 | 0.415 | 0.302 | 0.257 | 0.219 | 0.192 | 0.176 |
| Row 10 | 0 | 0 | 0 | 0.003 | 0.006 | 0.026 | 0.037 | 0.039 | 0.308 | 1 | 0.584 | 0.379 | 0.3 | 0.257 | 0.225 | 0.197 |
| Row 11 | 0 | 0 | 0 | 0.001 | 0.003 | 0.006 | 0.03 | 0.034 | 0.034 | 0.339 | 1 | 0.52 | 0.375 | 0.298 | 0.258 | 0.232 |
| Row 12 | 0 | 0 | 0 | 0 | 0.001 | 0.003 | 0.007 | 0.034 | 0.03 | 0.029 | 0.37 | 1 | 0.512 | 0.371 | 0.297 | 0.259 |
| Row 13 | 0 | 0 | 0 | 0 | 0 | 0.001 | 0.003 | 0.009 | 0.028 | 0.025 | 0.025 | 0.401 | 1 | 0.505 | 0.367 | 0.295 |
| Row 14 | 0 | 0 | 0 | 0 | 0 | 0 | 0.001 | 0.003 | 0.007 | 0.021 | 0.02 | 0.02 | 0.352 | 1 | 0.497 | 0.364 |
| Row 15 | 0 | 0 | 0 | 0 | 0 | 0 | 0 | 0.001 | 0.002 | 0.005 | 0.015 | 0.015 | 0.018 | 0.302 | 1 | 0.489 |
| Row 16 | 0 | 0 | 0 | 0 | 0 | 0 | 0 | 0 | 0.001 | 0.002 | 0.003 | 0.008 | 0.014 | 0.016 | 0.252 | 1 |
| Row 17 | 0 | 0 | 0 | 0 | 0 | 0 | 0 | 0 | 0 | 0.001 | 0.001 | 0.001 | 0.007 | 0.012 | 0.014 | 0.203 |
| Row 18 | 0 | 0 | 0 | 0 | 0 | 0 | 0 | 0 | 0 | 0 | 0 | 0.001 | 0.001 | 0.005 | 0.011 | 0.012 |
| Row 19 | 0 | 0 | 0 | 0 | 0 | 0 | 0 | 0 | 0 | 0 | 0 | 0 | 0 | 0.001 | 0.004 | 0.009 |
| Row 20 | 0 | 0 | 0 | 0 | 0 | 0 | 0 | 0 | 0 | 0 | 0 | 0 | 0 | 0 | 0.001 | 0.002 |
| Row 21 | 0 | 0 | 0 | 0 | 0 | 0 | 0 | 0 | 0 | 0 | 0 | 0 | 0 | 0 | 0 | 0 |
| Row 22 | 0 | 0 | 0 | 0 | 0 | 0 | 0 | 0 | 0 | 0 | 0 | 0 | 0 | 0 | 0 | 0 |
| Row 23 | 0 | 0 | 0 | 0 | 0 | 0 | 0 | 0 | 0 | 0 | 0 | 0 | 0 | 0 | 0 | 0 |
| Row 24 | 0 | 0 | 0 | 0 | 0 | 0 | 0 | 0 | 0 | 0 | 0 | 0 | 0 | 0 | 0 | 0 |
| Row 25 | 0 | 0 | 0 | 0 | 0 | 0 | 0 | 0 | 0 | 0 | 0 | 0 | 0 | 0 | 0 | 0 |
| Row 26 | 0 | 0 | 0 | 0 | 0 | 0 | 0 | 0 | 0 | 0 | 0 | 0 | 0 | 0 | 0 | 0 |
| Row 27 | 0 | 0 | 0 | 0 | 0 | 0 | 0 | 0 | 0 | 0 | 0 | 0 | 0 | 0 | 0 | 0 |
| Row 28 | 0 | 0 | 0 | 0 | 0 | 0 | 0 | 0 | 0 | 0 | 0 | 0 | 0 | 0 | 0 | 0 |
| Row 29 | 0 | 0 | 0 | 0 | 0 | 0 | 0 | 0 | 0 | 0 | 0 | 0 | 0 | 0 | 0 | 0 |
| Row 30 | 0 | 0 | 0 | 0 | 0 | 0 | 0 | 0 | 0 | 0 | 0 | 0 | 0 | 0 | 0 | 0 |
| Row 31 | 0 | 0 | 0 | 0 | 0 | 0 | 0 | 0 | 0 | 0 | 0 | 0 | 0 | 0 | 0 | 0 |
| Row 32 | 0 | 0 | 0 | 0 | 0 | 0 | 0 | 0 | 0 | 0 | 0 | 0 | 0 | 0 | 0 | 0 |

FIG. 16B

| | Col 17 | Col 18 | Col 19 | Col 20 | Col 21 | Col 22 | Col 23 | Col 24 | Col 25 | Col 26 | Col 27 | Col 28 | Col 29 | Col 30 | Col 31 | Col 32 |
|---|---|---|---|---|---|---|---|---|---|---|---|---|---|---|---|---|
| Row 1 | 0.039 | 0.046 | 0.041 | 0.03 | 0.04 | 0.043 | 0.047 | 0.046 | 0.045 | 0.036 | 0.059 | 0.07 | 0.062 | 0.059 | 0.046 | 0.046 |
| Row 2 | 0.055 | 0.055 | 0.054 | 0.042 | 0.043 | 0.05 | 0.05 | 0.053 | 0.05 | 0.048 | 0.065 | 0.082 | 0.086 | 0.07 | 0.056 | 0.046 |
| Row 3 | 0.076 | 0.071 | 0.071 | 0.056 | 0.053 | 0.055 | 0.06 | 0.058 | 0.059 | 0.054 | 0.075 | 0.094 | 0.104 | 0.081 | 0.078 | 0.056 |
| Row 4 | 0.081 | 0.085 | 0.088 | 0.064 | 0.064 | 0.064 | 0.067 | 0.071 | 0.063 | 0.065 | 0.082 | 0.103 | 0.122 | 0.089 | 0.075 | 0.078 |
| Row 5 | 0.092 | 0.099 | 0.093 | 0.073 | 0.073 | 0.072 | 0.075 | 0.08 | 0.081 | 0.069 | 0.093 | 0.109 | 0.131 | 0.108 | 0.075 | 0.075 |
| Row 6 | 0.111 | 0.109 | 0.118 | 0.093 | 0.081 | 0.082 | 0.08 | 0.086 | 0.092 | 0.091 | 0.101 | 0.122 | 0.136 | 0.114 | 0.094 | 0.094 |
| Row 7 | 0.123 | 0.133 | 0.125 | 0.102 | 0.1 | 0.09 | 0.091 | 0.089 | 0.098 | 0.105 | 0.113 | 0.132 | 0.151 | 0.116 | 0.098 | 0.098 |
| Row 8 | 0.153 | 0.147 | 0.155 | 0.114 | 0.108 | 0.107 | 0.098 | 0.099 | 0.097 | 0.109 | 0.118 | 0.134 | 0.164 | 0.115 | 0.095 | 0.095 |
| Row 9 | 0.163 | 0.171 | 0.171 | 0.118 | 0.119 | 0.114 | 0.114 | 0.107 | 0.108 | 0.105 | 0.118 | 0.13 | 0.156 | 0.117 | 0.08 | 0.08 |
| Row 10 | 0.183 | 0.189 | 0.189 | 0.134 | 0.127 | 0.124 | 0.121 | 0.12 | 0.115 | 0.117 | 0.122 | 0.127 | 0.143 | 0.112 | 0.07 | 0.07 |
| Row 11 | 0.202 | 0.212 | 0.216 | 0.154 | 0.141 | 0.135 | 0.129 | 0.127 | 0.127 | 0.124 | 0.127 | 0.138 | 0.137 | 0.114 | 0.068 | 0.068 |
| Row 12 | 0.238 | 0.236 | 0.242 | 0.176 | 0.16 | 0.148 | 0.143 | 0.133 | 0.134 | 0.134 | 0.13 | 0.137 | 0.154 | 0.113 | 0.085 | 0.085 |
| Row 13 | 0.259 | 0.274 | 0.271 | 0.192 | 0.182 | 0.166 | 0.154 | 0.152 | 0.138 | 0.14 | 0.144 | 0.137 | 0.147 | 0.12 | 0.089 | 0.089 |
| Row 14 | 0.293 | 0.31 | 0.309 | 0.213 | 0.197 | 0.188 | 0.172 | 0.161 | 0.16 | 0.143 | 0.145 | 0.154 | 0.143 | 0.114 | 0.085 | 0.085 |
| Row 15 | 0.36 | 0.36 | 0.36 | 0.242 | 0.219 | 0.203 | 0.194 | 0.178 | 0.168 | 0.168 | 0.153 | 0.15 | 0.164 | 0.124 | 0.08 | 0.08 |
| Row 16 | 0.481 | 0.453 | 0.426 | 0.274 | 0.246 | 0.225 | 0.208 | 0.2 | 0.184 | 0.174 | 0.176 | 0.162 | 0.155 | 0.13 | 0.105 | 0.105 |
| Row 17 | 1 | 0.685 | 0.547 | 0.321 | 0.283 | 0.25 | 0.231 | 0.214 | 0.206 | 0.189 | 0.182 | 0.183 | 0.172 | 0.133 | 0.096 | 0.096 |
| Row 18 | 0.153 | 1 | 0.888 | 0.407 | 0.324 | 0.291 | 0.255 | 0.237 | 0.219 | 0.212 | 0.196 | 0.19 | 0.191 | 0.136 | 0.111 | 0.111 |
| Row 19 | 0.01 | 0.085 | 1 | 0.526 | 0.413 | 0.326 | 0.3 | 0.259 | 0.243 | 0.225 | 0.209 | 0.203 | 0.197 | 0.155 | 0.1 | 0.1 |
| Row 20 | 0.008 | 0.009 | 0.017 | 1 | 0.548 | 0.42 | 0.328 | 0.308 | 0.263 | 0.249 | 0.228 | 0.206 | 0.21 | 0.153 | 0.119 | 0.119 |
| Row 21 | 0.001 | 0.005 | 0.009 | 0.513 | 1 | 0.571 | 0.426 | 0.33 | 0.317 | 0.267 | 0.242 | 0.232 | 0.204 | 0.162 | 0.109 | 0.109 |
| Row 22 | 0 | 0 | 0.002 | 0.029 | 0.43 | 1 | 0.594 | 0.432 | 0.333 | 0.325 | 0.273 | 0.234 | 0.235 | 0.158 | 0.114 | 0.114 |
| Row 23 | 0 | 0 | 0 | 0.012 | 0.025 | 0.347 | 1 | 0.616 | 0.438 | 0.335 | 0.315 | 0.28 | 0.227 | 0.187 | 0.113 | 0.113 |
| Row 24 | 0 | 0 | 0 | 0.001 | 0.01 | 0.021 | 0.265 | 1 | 0.639 | 0.444 | 0.337 | 0.305 | 0.286 | 0.18 | 0.138 | 0.138 |
| Row 25 | 0 | 0 | 0 | 0 | 0.001 | 0.008 | 0.017 | 0.182 | 1 | 0.662 | 0.431 | 0.339 | 0.295 | 0.223 | 0.133 | 0.133 |
| Row 26 | 0 | 0 | 0 | 0 | 0 | 0 | 0.006 | 0.013 | 0.099 | 1 | 0.619 | 0.417 | 0.341 | 0.236 | 0.16 | 0.16 |
| Row 27 | 0 | 0 | 0 | 0 | 0 | 0 | 0 | 0.004 | 0.01 | 0.017 | 1 | 0.577 | 0.403 | 0.295 | 0.178 | 0.178 |
| Row 28 | 0 | 0 | 0 | 0 | 0 | 0 | 0 | 0 | 0.002 | 0.006 | 0.19 | 1 | 0.535 | 0.355 | 0.249 | 0.249 |
| Row 29 | 0 | 0 | 0 | 0 | 0 | 0 | 0 | 0 | 0 | 0 | 0.004 | 0.364 | 1 | 0.566 | 0.307 | 0.307 |
| Row 30 | 0 | 0 | 0 | 0 | 0 | 0 | 0 | 0 | 0 | 0 | 0 | 0.002 | 0.538 | 1 | 0.596 | 0.596 |
| Row 31 | 0 | 0 | 0 | 0 | 0 | 0 | 0 | 0 | 0 | 0 | 0 | 0 | 0 | 0.269 | 1 | 1 |
| Row 32 | 0 | 0 | 0 | 0 | 0 | 0 | 0 | 0 | 0 | 0 | 0 | 0 | 0 | 0 | 0 | 1 |

FIG. 17

| | PULSE HEIGHT (mV) | MEASURED PHD DATA | | | DECONVOLUTION RESULTS MATRIX INVERSION | | | DECONVOLUTION RESULTS SUCCESSIVE SUBTRACTION | | |
|---|---|---|---|---|---|---|---|---|---|---|
| | | PHD-A | PHD-B | PHD-C | dPHD-A | dPHD-B | dPHD-C | dPHD-A | dPHD-B | dPHD-C |
| Row 1 | 5.6 | 1077 | 1019 | 738 | 0 | 0 | 0 | 0 | 0 | 0 |
| Row 2 | 7 | 1527 | 1344 | 1061 | 197 | 138 | 464 | 0 | 253 | 0 |
| Row 3 | 8.7 | 1883 | 1669 | 1275 | 33 | 487 | 0 | 0 | 22 | 0 |
| Row 4 | 10.9 | 2166 | 1842 | 1580 | 0 | 0 | 365 | 0 | 0 | 0 |
| Row 5 | 13.6 | 2512 | 2205 | 1789 | 0 | 116 | 0 | 0 | 0 | 0 |
| Row 6 | 17 | 3280 | 2649 | 2095 | 0 | 0 | 0 | 0 | 17 | 0 |
| Row 7 | 21.3 | 3765 | 2999 | 2511 | 99 | 401 | 161 | 0 | 0 | 0 |
| Row 8 | 26.6 | 4569 | 3538 | 2995 | 0 | 0 | 0 | 0 | 0 | 0 |
| Row 9 | 33.2 | 5305 | 4099 | 3366 | 0 | 172 | 0 | 0 | 0 | 0 |
| Row 10 | 41.5 | 6334 | 4683 | 4001 | 0 | 0 | 438 | 0 | 0 | 408 |
| Row 11 | 51.9 | 8093 | 5840 | 4680 | 1838 | 1082 | 1237 | 1843 | 1107 | 1171 |
| Row 12 | 64.8 | 11725 | 7831 | 5762 | 28485 | 14138 | 7582 | 28592 | 14299 | 7601 |
| Row 13 | 81 | 6312 | 5703 | 4698 | 9474 | 6511 | 2469 | 9381 | 6585 | 1992 |
| Row 14 | 101.2 | 4556 | 4787 | 4656 | 0 | 22 | 0 | 0 | 22 | 0 |
| Row 15 | 126.5 | 5576 | 5732 | 5555 | 465 | 56 | 0 | 467 | 57 | 0 |
| Row 16 | 158.1 | 7062 | 7427 | 7445 | 2776 | 3279 | 2435 | 2794 | 3321 | 2481 |
| Row 17 | 197.6 | 10375 | 10853 | 11239 | 23151 | 24988 | 25093 | 23270 | 25264 | 25649 |
| Row 18 | 246.9 | 7632 | 8075 | 8609 | 1435 | 3861 | 8580 | 1442 | 3909 | 8777 |
| Row 19 | 308.5 | 8210 | 8093 | 7477 | 33255 | 34347 | 31941 | 33423 | 34738 | 32660 |
| Row 20 | 385.5 | 211 | 213 | 205 | 666 | 737 | 720 | 669 | 745 | 732 |
| Row 21 | 481.7 | 86 | 72 | 70 | 308 | 267 | 273 | 310 | 261 | 280 |
| Row 22 | 602 | 19 | 18 | 12 | 70 | 73 | 48 | 70 | 65 | 53 |
| Row 23 | 752.2 | 3 | 1 | 1 | 12 | 0 | 0 | 4 | 0 | 0 |
| Row 24 | 940 | 0 | 4 | 0 | 0 | 4 | 4 | 0 | 9 | 4 |
| Row 25 | 1174.7 | 3 | 4 | 2 | 8 | 4 | 4 | 8 | 9 | 0 |
| Row 26 | 1467.9 | 1 | 4 | 1 | 0 | 13 | 4 | 0 | 13 | 4 |
| Row 27 | 1834.3 | 1 | 2 | 0 | 0 | 4 | 4 | 0 | 4 | 4 |
| Row 28 | 2292.2 | 3 | 2 | 2 | 4 | 4 | 4 | 4 | 4 | 4 |
| Row 29 | 2864.4 | 3 | 1 | 1 | 12 | 4 | 4 | 12 | 4 | 4 |
| Row 30 | 3579.4 | 0 | 0 | 0 | 0 | 0 | 0 | 0 | 0 | 0 |
| Row 31 | 4441.9 | 0 | 0 | 0 | 0 | 0 | 0 | 0 | 0 | 0 |
| Row 32 | 5420 | 0 | 0 | 0 | 0 | 0 | 0 | 0 | 0 | 0 |

SENSORS AND METHODS FOR HIGH-SENSITIVITY OPTICAL PARTICLE COUNTING AND SIZING

This application is a divisional of application Ser. No. 10/847,618, filed on May 18, 2004 now U.S. Pat. No. 7,127,356, which is a divisional of application Ser. No. 10/196,714, filed on Jul. 17, 2002 now U.S. Pat. No. 6,794,671, the entire contents of which are hereby incorporated by reference.

BACKGROUND OF THE INVENTION

1. Field of the Invention

This invention relates to methods and apparatus for optical sensing, including counting and sizing of individual particles of varying size in a fluid suspension, and more particularly, to such methods and apparatus which yield higher sensitivity and coincidence concentration than can be realized by optical sensors of conventional design.

2. Description of Related Art

It is useful to review the principles underlying the traditional method of optical particle counting, hereinafter referred to as single-particle optical sensing (SPOS). Sensors that are used to implement SPOS are based on the physical technique of light extinction (LE) or light scattering (LS), or some combination of the two. The optical design of a traditional SPOS sensor based on the LE technique is shown schematically in FIG. 1. A fluid, consisting of a gas or liquid, in which particles of various sizes are suspended, is caused to flow through a physical flow channel 10, typically of rectangular cross section. Two of the opposing parallel surfaces 12 and 14 defining the flow channel are opaque, while the remaining two opposing parallel surfaces 16 and 18 perpendicular to the opaque pair are transparent, comprising the "front" and "back" windows of the flow cell 10. A beam of light 20 of appropriate shape enters front window 16 of flow cell 10, passes through the flowing fluid and particles, exits flow cell 10 through back window 18 and impinges on a relatively distant light-extinction detector $D_{LE}$.

The width of front and back windows 16 and 18 along the direction defined by the x-axis is defined as "a" (FIG. 1). The depth of flow cell 10, along the direction defined by the y-axis, parallel to the axis of the incident light beam, is defined as "b." Suspended particles of interest are caused to pass through flow cell 10 along the direction defined by the z-axis (from top to bottom in FIG. 1) at a steady, appropriate rate of flow, F, expressed in units of milliliters (ml) per second, or minute.

The optical sensing zone 22 ("OSZ"), or "view volume," of the sensor is the thin region of space defined by the four internal surfaces of flow channel 10 and the ribbon-like beam of light that traverses channel 10. The resulting shape of the OSZ resembles a thin, approximately rectangular slab (having concave upper and lower surfaces, as described below), with a minimum thickness defined as 2w, oriented normal to the longitudinal axis of flow cell 10 (FIG. 1). Source of illumination 24 is typically a laser diode, having either an elliptical- or circular-shaped beam, with a gaussian intensity profile along each of two mutually orthogonal axes and a maximum intensity at the center of the beam. Two optical elements are typically required to create the desired shape of the incident light beam that, together with the front and back windows of the flow channel 10, defines the OSZ. The first optical element is usually a lens 26, used to focus the starting collimated beam at the center (x-y plane) of flow cell 10. The focused beam "waist," or width, 2w, is proportional to the focal length of the lens and inversely proportional to the width of the starting collimated beam, defined by its $1/e^2$ intensity values. The focused beam width, 2w, also depends on the orientation of the beam, if its cross section is not circular.

The second optical element is typically a cylindrical lens 28, used to "defocus," and thereby widen, the light beam in one direction—i.e. along the x-axis. In effect, cylindrical lens 28 converts what otherwise would be a uniformly focused beam (of elliptical or circular cross section) impinging on the flow cell, into a focused "line-source" that intersects flow channel 10 parallel to the x-axis. The focal length and location of cylindrical lens 28 are chosen so that the resulting beam width (defined by its $1/e^2$ intensity points) along the x-axis at the center of the flow cell is much larger than the width, a, of the flow channel 10. As a result, front window 16 of the sensor captures only the top portion of the gaussian beam, where the intensity is nearly uniform. Substantial uniformity of the incident intensity across the width (x-axis) of the flow channel 10 is essential in order to achieve optimal sensor resolution. The intensity profile along the z-axis of the resulting ribbon-like light beam is also gaussian, being brightest at the center of the OSZ and falling to $1/e^2$ at its "upper" and "lower" edges/faces, where the distance between these intensity points defines the thickness, 2w, of the OSZ.

The shape of the OSZ 22 deviates from that of an idealized, rectangular slab shape suggested in FIG. 1. Rather, the cross-sectional shape of the OSZ in the y-z plane resembles a bow tie, or hourglass, owing to the fact that the incident light beam is focused along the y-axis. However, assuming that the optical design of the sensor has been optimized, the focal length of the focusing lens will be much larger than the depth, b, of the flow cell. Therefore, the "depth of field" of the focused beam—defined as the distance between the two points along the y-axis at which the beam thickness expands to $\sqrt{2} \times 2w$—will be significantly larger than the depth, b, of the flow cell. Consequently, the variation in light intensity will be minimal along the y-axis.

The ribbon-like light beam passes through the fluid-particle suspension and impinges on a suitable light detector DLE (typically a silicon photodiode). In the absence of a particle in the OSZ, detector $D_{LE}$ receives the maximum illumination. A particle that passes through the OSZ momentarily "blocks" a small fraction of the incident light impinging on detector $D_{LE}$, causing a momentary decrease in the photocurrent output of detector $D_{LE}$ and the corresponding voltage "$V_{LE}$" produced by suitable signal-conditioning means. The resulting signal consists of a negative-going pulse 30 of height $\Delta V_{LE}$, superimposed on a d.c. "baseline" level 32 of relatively large magnitude, $V_0$, shown schematically in FIG. 2. Obviously, the larger the particle, the larger the pulse height, $\Delta V_{LE}$, both in absolute magnitude and as a fraction of $V_0$.

The detector signal, $V_{LE}$, is processed by an electronic circuit 34, which effectively removes the baseline voltage, $V_0$, typically either by subtracting a fixed d.c.voltage from $V_{LE}$ or by "a.c. coupling," using an appropriate high-pass filter. This action allows for capture of the desired negative-going pulses of various heights, $\Delta V_{LE}$. The resulting signal pulses are then "conditioned" further, typically including inversion and amplification. Each pulse is digitized using a fast, high-resolution analog-to-digital (A/D) converter, allowing its height to be determined with relatively high accuracy. A calibration table is generated, using a series of "standard" particles (typically polystyrene latex spheres) of known diameter, d, spanning the desired size range. This set of discrete values of $\Delta V_{LE}$ vs d is stored in computer memory and typically displayed as log $\Delta V_{LE}$ vs log d, with a continuous curve connecting the points. The set of measured pulse heights, $\Delta V_{LE}$, are easily converted to a set of particle diameters, d, by interpolation of the calibration table values.

In principle, there are several physical mechanisms that can contribute to the light extinction effect. These include refraction, reflection, diffraction, scattering and absorbance. The mechanisms of refraction and reflection dominate the LE effect for particles significantly larger than the wavelength of the incident light, typically 0.6-0.9 micrometers (μm). In the case of refraction, the light rays incident on a particle are deflected toward or away from the axis of the beam, depending on whether the refractive index of the particle is larger or smaller, respectively, than the refractive index of the surrounding fluid. Provided the two refractive indices differ sufficiently and the (small) detector element, $D_{LE}$, is located sufficiently far from the flow cell, the refracted rays of light will diverge sufficiently that they fail to impinge on detector $D_{LE}$, thus yielding the desired signal, $\Delta V_{LE}$. The mechanism of reflection necessarily accompanies refraction, and the greater the refractive index "contrast" between the particles and fluid, the greater the fraction of incident light reflected by the particle. The phenomenon of diffraction typically has a negligible effect on the LE signal, because the angles associated with the major intensity maxima and minima are smaller than the typical solid angle defined by the distant detector $D_{LE}$.

By contrast, however, the light scattering phenomenon typically makes an important contribution to the LE signal. It is the dominant mechanism for particles comparable in size to, or smaller than, the wavelength of the incident light. The magnitude and angular distribution of the scattered light intensity depends on the size, shape and orientation of the particle, as well as the contrast in refractive index and the wavelength of the beam. The well-known Mie and Rayleigh scattering theories describe in detail the behavior of the light scattering intensity. The greater the amount of light scattered off-axis, away from the axis of the incident light beam, the smaller the light flux that reaches the extinction detector $D_{LE}$.

The mechanism of absorbance may be significant for particles that are highly pigmented, or colored. The magnitude of this effect depends on the wavelength of the incident light, as well as the size of the particle. The contribution of absorbance to the overall LE signal may be significant for particles significantly larger than the wavelength.

There is a simple, approximate relationship between the particle size and the magnitude of the LE signal, $\Delta V_{LE}$. The total light flux incident on the detector, $D_{LE}$, in the absence of a particle in the OSZ is proportional to the area of illumination, $A_0$. This is approximated by $$A_0 \approx 2aw \tag{1}$$

Assuming that the intensity of the beam incident on the flow channel 10 is uniform along both its width, a, and over the thickness, $2w$, of the beam (i.e. assumed to have a rectangular, rather than gaussian, profile).

If one makes the additional simplifying assumption that a particle completely blocks the light that impinges on it (i.e. perfect, 100% extinction), then the fraction of incident light blocked by the particle is given by $\Delta A/A_0$, where $\Delta A$ represents the cross-sectional area of the particle. The pulse height, $\Delta V_{LE}$, of the light-extinction signal for particle diameters$<2w$ can then be expressed by $$\Delta V_{LE} = (\Delta A/A_0)V_0 \tag{2}$$

For simplicity, the particles are assumed to be spherical and homogeneous, in order to avoid complicating details related to particle shape and orientation. Quantity $\Delta A$ for a particle of diameter d is therefore given by $$\Delta A = \pi d^2/4 \tag{3}$$

In cases where the particle blocks less than 100% of the light incident on it—e.g. where the dominant mechanism for extinction is mostly light scattering, rather than refraction and reflection—quantity $\Delta A$ represents the "effective" cross-sectional area, smaller than the actual physical area.

The velocity, v, of the particles that pass through the OSZ is given by $$v = F/ab \tag{4}$$

The pulse width, $\Delta t$, represents the time of transit of the particle through the OSZ—i.e. between the $1/e^2$ intensity points that define the width, $2w$. Neglecting the size of the particle compared to quantity $2w$, the pulse width is given by $$\Delta t2 = w/v \tag{5}$$

It is instructive to calculate the values of the parameters above for a typical LE sensor—the Model LE400-1E sensor (Particle Sizing Systems, Santa Barbara, Calif.), with a=400 μm, b=1000 μm, and $2w \approx 35$ μm, assuming F=60 ml/min.

$$A_0 = 1.4 \times 10^4 \, \mu m^2$$

$$v = 250 \, cm/sec$$

$$t = 14 \times 10^{-6} \, sec = 14 \, \mu sec$$

The smallest particle diameter that typically can be reliably detected (i.e. where $\Delta V_{LE}$ exceeds the typical r.m.s. noise level by at least a 2:1 ratio) is approximately 1.3 μm. This corresponds to a physical blockage ratio, $\Delta A/A_0$, of 0.000095, or less than 0.01%.

Increasing the intensity of the light source should, in theory, have no influence on the sensitivity, or lower particle size limit, of an extinction-type sensor. For a given baseline voltage, $V_0$, the pulse height, $\Delta V_{LE}$, depends only on the fraction of the illuminated detector area effectively blocked by the particle, $\Delta A/A_0$. (The effect of sample turbidity is discussed later.) Only if a more powerful light source possesses lower noise, will the sensor be able to detect reliably a smaller fractional change in effective blocked area, and therefore a smaller particle diameter. However, any such improvement in performance, due to increased S/N ratio, represents only a second-order effect and is usually not significant.

Using the parameters for the LE-type sensor discussed above, one obtains an estimate of the effective volume, $V_{OSZ}$, of the OSZ, $$V_{OSZ} = 2abw = 1.4 \times 10^7 \, \mu m^3 = 1.4 \times 10^{-5} \, cm^3 \tag{6}$$

The reciprocal of the OSZ volume, $1/V_{OSZ}$, equals the number of "view volumes" contained in 1 $cm^3$ (i.e. 1 ml) of fluid—i.e. $1/V_{OSZ} \approx 7 \times 10^4$ for the example above.

The quantity $1V_{OSZ}$ provides a measure of the "coincidence limit" of the sensor—the concentration (# particles/ml) at which the particles pass one at a time through the OSZ, provided they are spaced uniformly throughout the fluid, with each particle effectively occupying one view volume at any given time. In reality, of course, the particles are located randomly throughout the fluid. Therefore, the particle concentration must be reduced substantially with respect to this "ideal" value—i.e. by 10:1 or more—in order to ensure the presence of only one particle at a time in the OSZ. The actual coincidence limit of the sensor is usually defined as the concentration at which only 1% of the particle counts are associated with two or more particles passing through the OSZ at the same time, possibly giving rise to a single detected pulse of exaggerated pulse height. Hence, the useful coincidence limit of the sensor is typically only 10% (or less) of the value $1/V_{OSZ}$. Using the example above, this implies a coincidence concentration of approximately 7,000 particles/ml. In practice the coincidence limit of a sensor of given design will also be a function of particle size. The value indicated is appropriate in the case of very fine particles, having diameters much smaller than the effective thickness, $2w$, of the OSZ. The coincidence limit may be significantly lower in the case of particles comparable in size to, or larger than, parameter $2w$. Therefore, in practice one often chooses to collect data at a particle concentration of only 50% (or less) of the value given above, in order to eliminate erroneous particle "counts" and distortion of the resulting particle size distribution (PSD).

For applications involving concentrated suspensions and dispersions, it is very desirable to increase the coincidence concentration of the sensor, so that less extensive dilution of the starting sample is required. First, this improvement lowers the volume of clean fluid needed to dilute the sample and reduces the extent to which the diluent fluid must be free of particle contamination. Second, and more important, extensive dilution of the starting concentrated suspension may not be feasible, if it results in significant changes in the PSD—e.g. due to promotion of particle agglomeration. Examples include pH-sensitive oxide "slurries" used for processing semiconductor wafers by the method known as chemical mechanical planarization (CMP). Also, for a variety of applications it is useful, if not essential, to increase the sensitivity of the SPOS method—i.e. to reduce the minimum detectable particle size. Increases in the coincidence concentration and improvements in the sensitivity of LE-type sensors are usually related, and there are several ways in which improvements in both parameters can be achieved.

The most obvious way in which the sensitivity of an extinction-type sensor can be improved is to decrease the cross-sectional area of illumination, $A_0$. Using the example above, this is accomplished by decreasing the lateral cell dimension, a, or the incident beam thickness, $2w$, or both. Concerning the latter course of action, the effective thickness, $2w$, of the OSZ can be reduced only to a limited extent. This limitation is imposed by the relationship between the focal length of the focusing lens, the depth of the flow cell, and the width of the starting light beam. Given the nature of gaussian beam optics and the limitations imposed by diffraction, it is impractical to decrease parameter $2w$ below approximately 5 µm. This reduction represents only a 7-fold improvement over the 35-µm value assumed in the example above. Furthermore, in order to achieve relatively high size resolution for smaller particles, it is useful to retain the quadratic dependence of the light-extinction pulse height, $\Delta V_{LE}$, on the particle diameter, d, which obtains only for values of d (substantially) smaller than $2w$. Hence, in order to achieve optimal performance for many important applications, it is usually not desirable to make the thickness of the OSZ appreciably thinner than about 10 µm.

Instead, it appears to be more attractive to reduce the lateral dimension, a, of the OSZ—e.g. from 400 µm (using the example above) to 40 µm. To a first approximation (ignoring nonlinear signal/noise effects), this 10-fold reduction in $A_0$ results in a similar 10-fold reduction in the effective cross-sectional area, $\Delta A_{LE}$, required to achieve a given fraction of blocked area, $\Delta A_{LE}/A_0$.

There is a second significant advantage that results from this 10-fold reduction of the width of the flow channel 10. The volume of the OSZ (Equation 6) is also reduced 10-fold, resulting in a reduction of the coincidence concentration by the same factor. Hence, the working sample concentration can be increased 10-fold, permitting a 10-fold lower extent of dilution required for the starting concentrated particle dispersion. Of course, the same 10-fold increase in the coincidence concentration can be achieved through a 10-fold reduction in the cell depth, b, rather than the cell width, a, considered above. However, the improvement in sensor sensitivity would no longer be obtained. Clearly, while dimensions "a" and "b" play equivalent roles with respect to determining $V_{OSZ}$, and therefore the coincidence concentration, they are not equivalent with respect to influencing sensor sensitivity.

Unfortunately, there is a serious disadvantage to this proposed approach. It is not practical to reduce dimension a (or b, for that matter) to such an extent (i.e. significantly smaller than 100 µm) for reasons that are obvious to anyone familiar with the use of SPOS technology. Such a small dimension virtually invites clogging of the flow channel 10, due to the inevitable existence of contaminant ("dirt") particles in the diluent fluid and/or large particles associated with the sample, such as over-size "outliers" and agglomerates of smaller "primary" particles. Generally, the minimum lateral dimension (either a or b) of the flow channel 10 in an LE-type sensor should be at least two, and preferably three to four, times larger than the largest particle expected to occur in the sample of interest. Otherwise, frequent clogging of the flow cell is inevitable, thus negating one of the principal advantages of the SPOS technique over an alternative single-particle sensing technique known as "electro-zone," or "resistive-pore," sensing (e.g. the "Coulter counter," manufactured by Beckman-Coulter Inc, Hialeah, Fla.).

One of the previously established ways of increasing the sensitivity of a conventional SPOS-type sensor is to use the method of light scattering (LS), rather than light extinction. With the LS technique the background, or baseline, signal is ideally zero in the absence of a particle in the OSZ. (In reality, there is always some low-level noise due to scattering from contaminants and solvent molecules, plus contributions from the light source, detector and amplifier.) Therefore, the height of the detected signal pulse due to a particle passing through the OSZ can be increased, for a given particle size and composition, simply by increasing the intensity of the light source. This simple expedient has resulted in sensors that can detect individual particles as small as 0.2 µm or smaller.

Fortunately, by adopting a completely different measurement approach, significantly higher sensitivity and coincidence concentration can be achieved from an SPOS device than is provided by a conventional LE or LS sensor. The resulting new apparatus and method form the basis of the present invention. The most significant difference in the optical design of the new sensor concerns the light beam that is used to define the OSZ. Rather than resembling a thin "ribbon" of light that extends across the entire flow channel (i.e. in the x-y plane, FIG. 1), it now consists of a thin "pencil" of light (aligned with the y-axis) that probes a narrow region of the flow channel 10. This beam, typically having an approximately gaussian intensity profile and circular cross section, effectively illuminates only a small fraction of the particles that flow through the sensor. The resulting area of illumination, $A_0$, is much smaller than the value typically found in a conventional sensor, which requires that the beam span the entire width (x-axis) of the flow channel 10. By definition, the intensity of the new beam is highly non-uniform in both the lateral (x-axis) direction and the direction of particle flow (z-axis).

Consequently, particles that pass through the sensor are necessarily exposed to different levels of maximum light intensity (i.e. at z=0), depending on their trajectories. The resulting signal pulse height generated by a particle now depends not only on its size, but also its path through the flow channel 10. Particles that pass through the center of the illuminating beam, where the intensity is highest, will generate LE (or LS) pulses of maximum height for a given size, while those that pass through regions of lesser intensity will produce pulses of corresponding reduced height. Hence, the use of a beam of non-uniform (usually, but not necessarily gaussian) intensity profile gives rise to the so-called "trajectory ambiguity" problem. A number of researchers have attempted to address this problem, using a variety of approaches.

The problem of trajectory ambiguity in the case of remote in-situ measurement of scattered light signals produced by unconfined particles was discussed more than twenty years ago by D. J. Holve and S. A. Self, in *Applied Optics*, Vol. 18, No. 10, pp. 1632-1652 (1979), and by D. J. Holve, in *J. Energy*, Vol. 4, No. 4, pp. 176-183 (1980). A mathematical deconvolution scheme, based on a non-negative least-squares (NNLS) procedure, was used to "invert" the set of measured light scattering pulse heights produced by combustion particles moving in free space. The measurement volume was defined by a ribbon (elliptical) beam with a gaussian intensity profile and an off-axis distant pinhole and detector, reverse imaged onto the beam. Holve et al explicitly rejected the well-known method of matrix inversion, as it was said to be ineffective when applied to their typical light scattering data. From the results and explanation provided, it is apparent that the resolution and accuracy of the PSDs that could be obtained using their light scattering scheme and NNLS deconvolution procedure were relatively poor. Multimodal distributions required relatively widely spaced particle size populations in order to be resolved reasonably "cleanly" using the referenced apparatus and method.

As disclosed in the Holve articles, the measurement region from which the scattered light signal is detected originates from a portion of the cross section of the illuminating beam. As will be discussed, the present invention also utilizes a beam that is spatially non-uniform in intensity, preferable having a circular gaussian profile. However, the present invention fully "embraces" this non-uniformity. That is, the measurement zone encompasses the entire cross section of the beam and not just the central region of highest (and least-variable) intensity. The particles to be counted and sized are caused to flow uniformly through a confined, well-defined space (flow channel) where the fraction of particles of any given size that is measured is fixed and ultimately known. The region from which data are collected is similarly fixed and well-defined and relatively immune to vibrations and optical misalignment. Given the inherent stability and different nature of the physical design associated with the present invention, it should not be surprising that the PSD results possess not only high sensitivity but also superior, unprecedented particle size resolution compared to the results obtained from the Holve approach. It is observed also that Holve's system is necessarily confined to light scattering as the means of detection. By contrast, the novel apparatus and methods taught in the present invention make possible sensors that are equally effective based on light scattering or light extinction.

Partly because of the limited quality of the PSD results that could be achieved using the apparatus and method described by Holve et al, there was subsequent recognition of the need to develop alternative methods that would permit gaussian beams to be used effectively for particle size determination. Of course, the simplest remedy, if appropriate, was seen to be elimination of the gaussian beam, itself, that is the source of the problem. Foxvag, in U.S. Pat. No. 3,851,169 (1974), proposed altering the intensity distribution of the laser beam, in order to reduce the non-uniformity inherent in its gaussian profile. Separately, G. Grehan and G. Gouesbet, in *Appl.* *Optics*, Vol 25, No. 19, pp 3527-3537 (1986), described the use of an "anti-gaussian" correcting filter in an expanded beam before focusing, thereby producing a "top-hat" beam profile, having substantially uniform intensity over an extended region. Fujimori et al, in U.S. Pat. No. 5,316,983 (1994), used a "soft" filter to convert a gaussian laser beam into a flattened intensity distribution.

Other proposals involved physically confining the flowing particles, so that they are forced to pass through the central portion of the laser beam, where the intensity is substantially uniform. An example is described by J. Heyder, in *J. Aerosol Science*, Vol 2, p. 341 (1971). This approach was also adopted by Bowen, et al, in U.S. Pat. No. 4,850,707 (1989), using a focused elliptical laser beam with a gaussian intensity profile, with a major axis much longer than the width of a hydrodynamically-focused "channel" containing the flowing particles. All of the particles are therefore exposed to substantially the same maximum intensity as they flow through the beam.

An early proposal for accommodating gaussian beams, proposed by Hodkinson, in *Appl. Optics*, Vol. 5, p. 839 (1966), and by Gravitt, in U.S. Pat. No. 3,835,315 (1974), was to determine the ratio of the peak scattered intensity signals detected simultaneously at two different scattering angles. This ratio is ideally independent of the intensity incident on the particle and, according to Mie theory, is uniquely related to its size. The reliability of this method was improved using the proposal of Hirleman, Jr., et al, in U.S. Pat. No. 4,188,121 (1980). The peak scattered intensities at more than two scattering angles are measured and the ratios of all pairs of values calculated. These ratios are compared with calibration curves in order to establish the particle diameter.

Several methods were suggested for selecting only those particles that have passed substantially through the center of the gaussian beam. A scheme for collecting off-axis scattered light from a distant, in-situ measurement volume, similar to the apparatus used by Holve et al, was described by J. R. Fincke, et al, in *J. Phys. E: Sci. Instrum.*, Vol 21, pp. 367-370 (1988). A beam splitter is used to distribute the scattered light between two detectors, each having its own pinhole aperture. One of the apertures is smaller than the beam waist in the measurement volume. Its detector is used to "select" particles suitable for measurement by the second detector, having a considerably larger aperture, ensuring that they pass substantially through the center of the beam, and therefore are eligible for counting and sizing. Notwithstanding the simplicity and apparent attractiveness of this approach, it was ultimately rejected by the authors, because of the difficulty of maintaining precise, stable alignment of the various optical elements. (This rejection is not unrelated to the limited quality of the PSD results obtained by Holve et al, alluded to above.)

Another set of proposed methods suggested the use of two concentric laser beams of different diameters, focused to a common region, through which particles are allowed to transversely flow, with the outside beam significantly larger in diameter than the inner beam. Two detectors are used to measure the amplitudes of light signals scattered by particles passing through each respective beam, distinguished by different wavelength (color) or polarization. Only those particles that pass through the central portion of the larger measurement beam, where the intensity is substantially uniform, produce signals from the smaller "validating" beam. Schemes using beams of two different colors are described by Goulas, et al, in U.S. Pat. No. 4,348,111 (1982), and Adrian, in U.S. Pat. No. 4,387,993 (1983). A variation on the concentric two-beam method is described by Bachalo, in U.S. Pat. No. 4,854,705 (1989). A mathematical formulation is used to process the two independently measured signal amplitudes together with the known beam diameters and intensities to determine the particle trajectory and, ultimately, the particle size. A variation on this approach is described by Knollenberg, in U.S. Pat. No. 4,636,075 (1987), using two focused, concentric beams distinguished by polarization. An elongated, elliptical beam shape is used to reduce the ratio of beam diameters needed to achieve acceptable particle size resolution and higher concentration limits.

Yet another variation of the two-beam approach is described by Flinsenberg, et al, in U.S. Pat. No. 4,444,500 (1984). A broad "measuring" beam and a narrower "validating" beam are again utilized, but in this case the latter is located outside the former, allowing both beams to have the same color and polarization. The plane containing the axes of the two beams is aligned parallel to the flow velocity of the particles. Achieving coincidence of two scattering signals detected separately from each beam ensures that the only particles to be counted and sized are those that have traversed the narrow beam, and hence the central region of the broad, measuring beam. Still another variation of the two-beam approach is described by Hirleman, Jr., in U.S. Pat. No. 4,251,733 (1981). Through the use of two physically separated gaussian beams, the particle trajectory can be determined from the relative magnitudes of the two scattered light signal pulses. This, in turn, permits the intensity incident on the particle everywhere along its trajectory to be calculated, from which the particle size can be determined.

Other proposals take advantage of an interferometric technique commonly utilized in laser Doppler velocimetry—i.e. crossing two coherent laser beams to obtain a fixed fringe pattern in a spatially localized region. The particle size can be determined from the peak scattering intensity, provided differences in trajectory can be accounted or compensated for. A straightforward scheme was proposed by Erdmann, et al, in U.S. Pat. No. 4,179,218 (1979), recognizing that a series of scattered light pulses is produced by each particle, related to the number of fringes through which it passes. The number of pulses establishes how close the particle has approached the center of the "probe" volume established by the fringe pattern, where the number of fringes is greatest and the intensity is brightest, corresponding to the center of each gaussian beam. An alternative method was proposed by C. F. Hess, in *Appl. Optics*, Vol. 23, No. 23, pp. 4375-4382 (1984), and in U.S. Pat. No. 4,537,507 (1985). In one embodiment, two coherent beams of unequal size are crossed, forming a fringe pattern. The small beam "identifies" the central region of the larger beam, having substantially uniform (maximal) intensity. A signal that contains the maximum a.c. modulation indicates that the particle has passed through the center of the fringe pattern and, hence, the middle of the large beam. The particle size is extracted from the "pedestal" (d.c.) signal after low-pass filtering removes the a.c. component. In a second embodiment, two crossed laser beams of one color are used to establish a fringe pattern at the center of a third, larger beam of a second color. A first detector establishes from the magnitude of the a.c. component of the scattered light signal whether a particle has passed substantially through the center of the fringe pattern. If so, the pulse height of the scattered light produced by the large beam, obtained from a second detector, is recorded. Bachalo, in U.S. Pat. No. 4,329,054 (1982), proposed distinguishing the central portion of a fringe pattern, corresponding to the central region of each gaussian beam, by using an additional small "pointer" beam of different color or polarization, responding to a separate detector means.

Finally, assorted other techniques have been proposed for addressing the gaussian beam/trajectory ambiguity problem. Bonin, et al, in U.S. Pat. No. 5,943,130 (1999), described a method for rapidly scanning a focused laser beam through a measurement volume, resulting in a scattered intensity pulse each time the beam crosses a particle. Given the high scanning frequency and velocity and the relatively low particle velocity, each particle is scanned several times while it is in the measurement volume. The resulting series of pulses can be fitted to the beam intensity profile and the maximum of the gaussian fit mapped to a particle diameter using a calibrated response function that correlates particle size with scattered light intensity. DeFreez, et al, in U.S. Pat. No. 6,111,642 (2000), proposed a "flow aperturing" technique. A particle/fluid delivery nozzle is designed so that the lateral velocity profile of the emerging particles approximately matches the gaussian intensity profile of the laser beam. The reduction in incident light level due to increasing distance of the particle trajectory from the beam axis is compensated approximately by the increase in integration time of the scattering signal, due to the lower velocity. The net integrated scattering signal is therefore ideally independent of the trajectory. An improvement was proposed by Girvin, et al, in U.S. Pat. No. 6,016,194 (2000), using a linear detector array to individually detect the scattered light signals associated with substantially each particle trajectory. The gain of each detector element can be adjusted to compensate for variations that remain in the net signal response of the system in the lateral direction, due to incomplete matching of the nozzle velocity and laser beam intensity profiles, differences in individual detector efficiencies and other effects.

SUMMARY OF THE INVENTION

It is the object of the invention to provide an SPOS device and method which provide significantly higher sensitivity and the ability to respond effectively to fluid suspensions which are relatively concentrated with a higher concentration of particles than is usual in the art and which, therefore, need not be diluted to the same degree as is required with prior art SPOS devices.

An SPOS device according to the invention establishes flow of the suspension through a physically well-defined measurement flow channel. A relatively narrow beam of light is directed through the measurement flow channel to illuminate an optical sensing zone within the measurement flow channel, the beam of light and the optical sensing zone being of such size relative to the size of the measurement flow channel that the SPOS device responds to a small fraction of the total number of particles flowing through the measurement flow channel with the result that the SPOS device will respond effectively to a relatively concentrated fluid suspension. The beam illuminates the optical sensing zone non-uniformly, having a central maximum intensity portion and a continuum of lesser intensities for positions spaced from the maximum intensity portion, so that some of the particles have trajectories through the maximum intensity portion, others of the particles have trajectories through the lesser intensity portions, and still others of the particles may have trajectories outside the zone.

The measurement flow channel has a thickness dimension axially of the beam of light, a width, or lateral, dimension transverse to the beam and a flow direction perpendicular to the thickness and width dimensions. The beam, which is much narrower than the measurement flow channel in the width direction, may be focused with a depth of field which is substantially larger than the thickness dimension, so that the beam has an effective width which does not vary substantially over the thickness dimension. The effective width which is defined as the width between opposing positions in the beam at which said lesser intensities have fallen to a given fraction, such as $1/e^2$, of said maximum intensity, is chosen so that particles can be effectively sized over the range of particles to be sized and is typically substantially one half the size of the largest particle to be sized. The intensity of the beam is highly non-uniform in the lateral direction and the direction of particle flow and may have a gaussian intensity profile. The beam may be circular in cross-section or elliptical, being wider transverse to the beam in the direction perpendicular to particle flow than in the direction parallel to particle flow.

The SPOS device of the invention uses a photo-detector and may operate on a light-extinction or light-scattering principle. Indeed, some sensor embodiments include both detection techniques. The photo-detector detects light from the zone to provide pulse height signals, each responsive to a particle flowing through said zone, the pulse height signals being functions of the sizes and trajectories of detected particles, particles of a given size providing a maximum pulse height signal when flowing through the maximum intensity portion and lesser pulse height signals when flowing through the lesser intensity positions of the zone. The pulse height signals, collectively, form a pulse height distribution (PHD). A statistically significant number of particles of the given size flow through the lesser intensity positions of the zone.

The use of a non-uniform beam creates the "trajectory ambiguity" problem. For this reason, the device and method include means for mathematically deconvoluting the pulse height distribution to provide a particle size distribution of the particles in the suspension. According to the invention, the deconvolution method is an improvement over deconvolution as taught in the prior art. The invention proposes the use of two deconvolution techniques: one using matrix inversion, and the other using successive subtraction.

Both techniques use a matrix. According to this invention, the process of setting up the matrix is simplified. The matrix has column basis vectors, each corresponding to a particular particle size. It has been proposed in the prior art to empirically base the values of all of the column basis vectors on measurements of particles of uniform, known size. Since the matrix may have a large number of columns (32, 64 and 128 are proposed in this application), according to the present invention only one or a few of the column basis vectors, or alternatively, none of them, need be empirically based on measurements of particles of known size. The remaining column basis vectors are computed by interpolation and/or extrapolation from empirically based column basis vectors. It is also proposed by this invention that some, or all, of the column basis vectors can be computed from a theoretical model. If some of them are so computed, the remaining column basis vectors can be computed by interpolation and/or extrapolation from those computed from existing data.

It is proposed to modify a method of deconvolution by matrix inversion. Each column basis vector has a maximum count pulse height at a location for a row which relates to a pulse height channel corresponding to a particle of known size associated with the column basis vector, the maximum count pulse height values for successive columns being arranged in a diagonal of the matrix. The matrix is modified by setting all terms below the diagonal to zero—that is to say, all terms corresponding to pulse height values greater than the maximum count pulse height value in a column are set to zero. This improves the accuracy, signal/noise ratio and reproducibility of the result.

The proposed method of deconvolution by successive subtraction involves setting up a matrix having a plurality of columns each containing a basis vector comprising a pulse height distribution of particles of a known size, each successive column containing a basis vector for particles of successively larger sizes, and a maximum-size basis vector containing a pulse height distribution for maximum size particles. The successive subtraction algorithm comprises the steps of:

starting with the basis vector with its maximum count value in the row corresponding to the largest pulse height;

scaling a column basis vector by a factor corresponding to the value of the row in the PHD that matches the column number; subtracting said scaled basis vector from the PHD to form an element of the deconvoluted PHD (dPHD), leaving an intermediate PHD vector with a smaller total number of particles;

and repeating this process using the remaining basis vectors until the entire PHD has been substantially consumed and all the elements of deconvoluted dPHD have been formed.

Using a calibration curve of the relationship of pulse height and diameter, each deconvoluted pulse height value in the dPHD is translated into a unique particle diameter associated with this pulse height value yielding a raw particle size distribution, PSD. The raw PSD is converted into a final PSD by normalizing the raw PSD by multiplying it by the value $1/\Phi_d$, where $\Phi_d$ is the fraction of particles actually detected by said device for particles of each size, d.

When the fluid suspension is relatively concentrated, light extinction type sensors may be affected by turbidity. Compensation for turbidity may be provided in one of three ways. First the baseline voltage levels for turbid and non-turbid liquids are sensed, a ratio is computed, and this ratio is used to increase the amplitude of the light-extinction signal such that the baseline voltage level for the turbid liquid is increased to approximately the baseline voltage level for the non-turbid liquid. Second, the pulse height signals generated by the turbid liquid are corrected by the computed ratio. Third, the intensity of the starting beam of light is adjusted in response to the ratio to compensate for turbidity.

An embodiment of the invention includes both a light-extinction (LE) detector and a light-scattering (LS) detector. Scattered light from the zone is passed to the (LS) detector through a mask to select light scattered between a first and a second angle to the beam. Light transmitted through the zone is directed to the LE detector. Another embodiment uses an optical fiber for conveying light from a light source to the optical sensing zone and projecting said light through the zone and an optical fiber for conveying the light from the zone to a LE detector. Scattered light from the zone is passed through a mask to select light scattered between a first and a second angle to the beam and this scattered light is collected by the LS detector. A further embodiment comprises a light source, a beam splitter for providing two light beams directed through a pair of optical sensing zones positioned within the measuring flow channel, each beam having an effective width compatible with a different range of particle sizes. Another embodiment comprises a light-scattering detector and means for passing a portion of the light through one of a plurality of masks located on a rotatable wheel, and means for selecting one of these masks by rotating the wheel to a desired orientation, each mask defining different angles between which the light is scattered and collected. A final embodiment projects a relatively wide collimated beam through the optical sensing zone. The beam has a central axis, and an acceptance aperture captures only those light rays that closely surround the central axis of the beam. This reduces the effective width of the beam to a width in a direction transverse to the axis of the light beam that is substantially one-half the size of the largest particle to be sized. An optical fiber couples the light rays to a detector.

BRIEF DESCRIPTION OF THE DRAWINGS

These and other objects, features and advantages of the invention will be more fully appreciated with reference to the accompanying Figures, in which:

FIG. 16A and FIG. 16B show a representative 32×32 matrix used for deconvolution of measured PHDs, obtained from nine measured basis vectors that span a size range from 0.722- to 20.0-μm;

FIG. 17 shows the measured PHD vectors (32×1) obtained from the trimodal samples "A," "B" and "C" (same as FIGS. 15A, 15B, 15C, but with 32-channel resolution) and the resulting dPHD vectors obtained by deconvolution using the matrix of FIGS. 16A and 16B of the three measured PHD vectors, using both matrix inversion and successive subtraction;

DETAILED DESCRIPTION OF THE INVENTION

The apparatus and method of the present invention is implemented by a sensor, based on either light extinction or scattering, for counting and sizing particles in a fluid suspension. A quantity of the suspension is caused to flow through the new sensor at a controlled flow rate within a confined, well-defined measurement flow channel. Like its conventional prior art counterpart, the new sensor responds to the passage of individual particles through an "optical sensing zone," or OSZ. Therefore, like its predecessor, it is also classified as a single-particle optical sensing (SPOS) device. However, as will be evident from the description to follow, the characteristics of this new sensor differ markedly from those obtained using the conventional SPOS approach. For simplicity, most of the description to follow will be related to a new light-extinction, or LE-type, sensor. However, with simple modification the new apparatus and method can be used equally effectively to implement a light-scattering, or LS-type, SPOS device, as will be discussed. Each of the new sensors, whether LE- or LS-type, is designed to function effectively at significantly higher concentrations than its conventional SPOS counterpart, and also to provide significantly higher sensitivity.

Achieving a significant increase in the coincidence concentration of an SPOS sensor requires making a similarly significant reduction in the volume, $V_{OSZ}$, of the OSZ. There is a practical limit on the extent to which the depth, b, of the flow channel 10 can be decreased as a means of reducing $V_{OSZ}$, in order to avoid frequent clogging of flow channel 10 by over-size particles. Therefore, a substantial reduction in the cross-sectional area, $A_0$, of the incident light beam that illuminates the fluid-particle mixture in the flow cell and impinges on detector $D_{LE}$ is required. Of course, there is an important additional advantage that results from reducing the illuminated area, $A_0$—a substantial reduction in the minimum detectable particle diameter. A particle of given size that passes through the center of the OSZ will momentarily "block" (i.e., refract, reflect, scatter and absorb) a larger fraction of the total light incident on the flow cell and detector, the smaller the parameter $A_0$.

Figure 3:
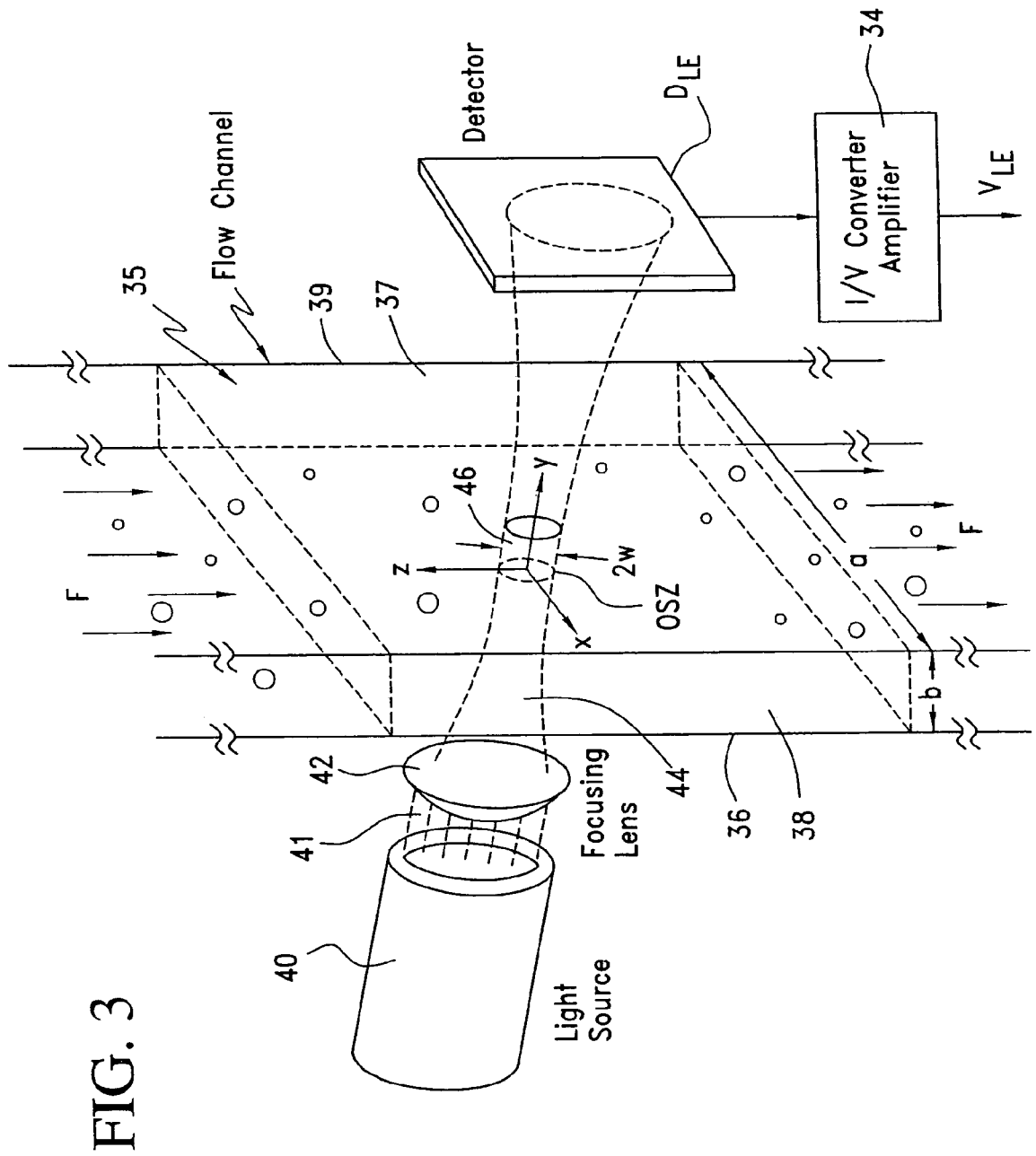
FIG. 3 is a simplified block diagram of the LE-type sensor of the present invention, hereinafter the "new LE-type sensor," using a relatively narrow, focused light beam to illuminate particles flowing in a relatively thin flow channel.

The principal defining characteristic of the new SPOS method is not simply a significant reduction in the size of the illuminated area, $A_0$, resulting in a significant reduction in $V_{OSZ}$ and improvement in sensitivity. Rather, it concerns the nature of the illuminating beam and the resulting OSZ thereby defined. As is shown in FIG. 3, there are two important and novel features inherent in the optical design. First, the incident beam alone (in conjunction with the front and back windows 36 and 37 of the measurement flow channel 35) defines the OSZ. The side walls 38 and 39 that confine the fluid-particle suspension along the x-axis (FIG. 3) are no longer of any consequence with respect to definition of the OSZ. Second, the physical volume associated with the OSZ can no longer be described by a single value; rather, it now depends on the size of the particles being measured.

Figure 1:
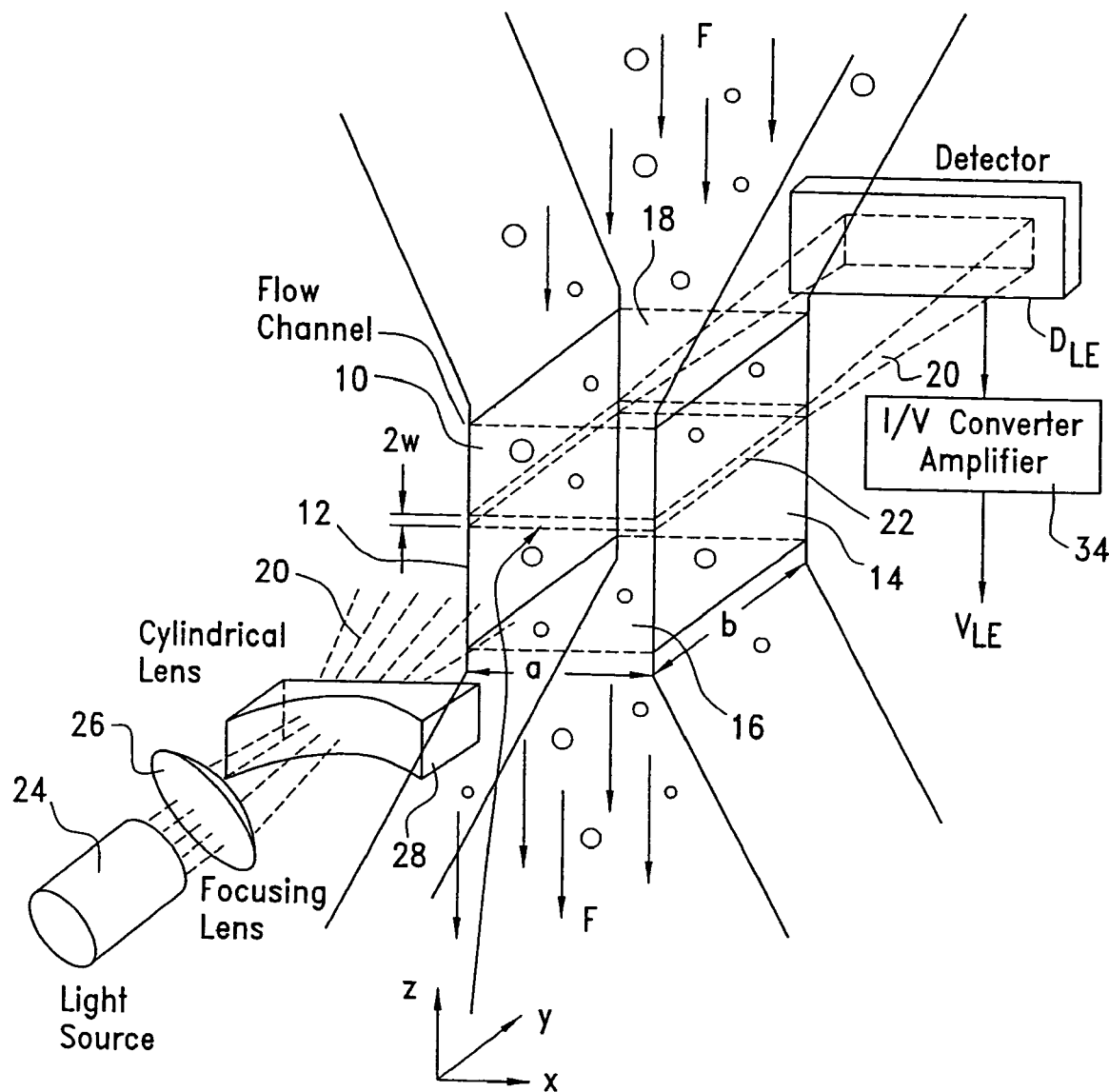
FIG. 1 is a simplified block diagram of the optical scheme typically used in a conventional prior art LE sensor.

The new approach, which is shown schematically in FIG. 3, is to illuminate measurement flow channel 35 with a light beam 41 from a laser light source 40 which is focused by a lens 42 to form a beam 44 of relatively narrow cross section—i.e., smaller than. the typical illuminated width, a, of the flow cell in a conventional LE-type sensor (FIG. 1). The resulting OSZ is therefore defined approximately by a "pencil" beam of light 46, together with the front and back windows of the flow cell, separated by dimension "b." The schematic diagram in FIG. 3 provides a simplified picture of the OSZ defined by focused light beam 46. First, the region of illumination that comprises the OSZ is not sharply defined, as implied by the approximately cylindrical zone indicated in FIG. 3. Rather, the outer boundary of the OSZ is "fuzzy," extending well beyond the zone indicated, as discussed below. Second, the beam passing through the flow channel 10, assuming that it has been focused, is typically is not uniform in width. Rather, in the case of a focused beam, its width varies over the depth of the measurement flow cell 35. The extent to which the beam waist varies over the depth of the channel depends on the depth of field of the focused beam, defined as the distance (y-axis) between the points at which the beam waist grows to $\sqrt{2}$ times its minimum value. Ideally, the depth of field is significantly greater than the channel thickness, b, resulting in a relatively uniform beam width throughout the flow channel.

Consequently, there is a fundamental change in the physical design of the new sensor, quite apart from the radically different intensity profile of the illuminating light. In the conventional design, the physical width of the flow channel 10 and the effective width (x-axis) of the OSZ are one and the same, equal to dimension "a." By contrast, the physical width of the flow channel in the new sensor (also defined as "a") is typically much larger than the nominal width, $2w$, of the incident light beam and therefore has no significant influence on the OSZ. Hence, the spacers (or shims) 38 and 39 that separate the front and back windows 36 and 37, determining the depth, b, of the flow cell (and OSZ), no longer need to be opaque or smooth on an optical scale to avoid scattering by the edges. This is a significant advantage, making fabrication of the flow cell easier and less expensive.

It is usually convenient and effective to employ a "circularized" light beam, in which the incident intensity ideally depends only on the radial distance, r, from the beam axis (coincident with the y-axis, with $x=z=0$, as seen in FIG. 3). Typically, one employs a "gaussian" light beam—i.e. one having a gaussian intensity profile, described in the focal plane (minimum beam waist), at $y=b/2$, by $$I(r)=I_0\exp(-2r^2/w^2) \quad (7)$$

where $r^2=x^2+z^2$ for the assumed circular beam.

Quantity $2w$ is the diameter of an imaginary cylinder containing most of the incident light flux. The intensity on its surface equals $1/e^2$, where e is the base for natural logarithms, or 0.135 times its value, $I_0$, at the center of the beam ($r=0$). Essentially 100% (apart from losses due to reflections at optical interfaces and extinction by particles in the beam) of the light flux contained in the incident beam traverses the fluid-particle mixture in the flow channel and impinges on the distant detector $D_{LE}$. This causes detector $D_{LE}$ to provide a light extinction signal $V_{LE}$ in the form of a downwardly extending pulse, resembling pulse 30 in FIG. 2 at the output of I/V converter amplifier 34.

This behavior is in sharp contrast to the illumination scheme employed in a conventional LE-type sensor. There, the starting light beam is expanded greatly along the lateral (x) axis of the flow cell, so that its width ($1/e^2$ intensity) is much larger than the width, a, of the front window (and OSZ). As a result, there is relatively little variation in the incident intensity along the x-axis (i.e. for $y=z=0$) where the beam enters the flow cell, because the light is captured at the top of the x-expanded gaussian beam. Therefore, a particle passing through the OSZ will experience substantially the same maximum beam intensity (i.e. at $z=0$), regardless of its trajectory. The specific values of x and y defining the trajectory ideally have no influence on the resulting sensor response, i.e. the pulse height.

The contrast between the conventional optical design and the scheme employed in the new sensor could hardly be greater. In the new sensor, by deliberate design, there is a large variation in the incident intensity as a function of position (x-axis) across the width of the flow channel. In the case in which the incident light beam has a symmetric (circular) gaussian profile, the intensity variation is given by Equation 7, with $r=x$. The maximum intensity, $I_0$, is achieved at the center of the beam ($x=0$), where for simplicity $x=0$ represents the midpoint of the channel (with the side walls at $x=\pm a/2$). As noted, the intensity occurring at $x=\pm w$, $z=0$ is reduced substantially, to $0.135\ I_0$. The intensity drops steeply with increasing distance from the beam, falling, for example, to $0.018\ I_0$ at $x=\pm 2w$, $z=0$ and $0.00033\ I_0$ at $x=\pm 4w$, $z=0$.

The consequences for the light-extinction signal thus generated by the passage of particles through the new OSZ are far-reaching. First, as for a conventional LE-type sensor, the pulse height, $\Delta V_{LE}$, generated by passage of a particle through the OSZ in general increases with increasing particle size, all other factors being equal. In general, the larger the particle, the larger the fraction of light "removed" from the incident beam, thus unable to reach the detector $D_{LE}$. However, with the new sensor the fraction of light removed from the beam now depends on the precise trajectory of the particle—specifically, the minimum distance, $|x|$, of the particle to the center of the beam, $x=0$. (To first approximation, the response of the sensor will not vary significantly with changes in the y-axis value of the trajectory, assuming that the beam width is approximately constant over the depth of the flow channel, given an appropriately large depth of field, as discussed above.)

For a particle of given size and composition (hereinafter assumed to be spherical and homogeneous, for simplicity), the maximum "signal," or pulse height, is achieved when the particle passes through the center of the beam, $x=0$. A particle of given effective cross-sectional area, $\Delta A$, blocks the largest amount of incident light at the center of the beam, where the intensity is greatest. Particles of identical size that pass through the flow channel along different trajectories, with different minimum distances, $|x|$, from the beam axis, are exposed to varying, but smaller, maximum levels of illumination. The greater the distance from the beam axis, the lower the integrated intensity incident on a particle and, hence, the less light flux removed from the beam, and the smaller the resulting pulse height. The response therefore consists of a continuous "spectrum" of pulse heights, ranging from a maximum value, for trajectories that pass through the center of the beam, to essentially zero (i.e. indistinguishable from noise fluctuations), for trajectories located very far from the incident beam ($|x|\gg w$). The maximum pulse height depends on the beam waist, $2w$, and the size of the particles, as well as in some cases the refractive indices of the particles and surrounding fluid. (This depends on the extent to which light scattering is significant relative to refraction and reflection in contributing to the overall light extinction signal.) A crucial assumption is that the particle trajectories are distributed randomly (i.e. occur with equal frequency) within the flow channel. This assumption is usually valid, given the typical dimensions of the flow channel and the relatively low flow rates utilized. It is also assumed that the number of particles passing through the sensor is sufficiently large that the statistical fluctuations in the number of particles having trajectories with any given x-axis value (i.e. over any (narrow) range of x values) can be ignored.

The relationship between particle size and pulse height for the new sensor is therefore radically different from that obtained for a sensor of conventional design. In the latter case, particles of a given size (and composition) give rise to pulses of nearly uniform height, irrespective of their trajectories. This behavior is the most important goal of sensor design for the conventional SPOS method. The typically small variations in pulse height that occur, for example, when measuring polystyrene latex "standard" particles of essentially uniform size are caused by variations in the incident beam intensity within the OSZ along the x- and y-axes, for a given z-axis value. These variations ultimately determine the resolution of the sensor. The resulting width of the PSD is therefore mostly a consequence of residual non-uniformity of illumination across the OSZ, rather than an actual range of particle diameters.

By contrast, there is an obvious deterioration in the particle size resolution for the new sensor design. When a single particle passes through the sensor, it gives rise to a light-extinction pulse with a height, $\Delta V_{LE}$ that can vary between a given maximum value and essentially zero. Conversely, given a single detected pulse, it is impossible to determine the size of the particle that has produced it, solely from knowledge of the pulse height. For example, a particle that is relatively small, but which passes directly through the beam axis, yields the maximum pulse height possible for a particle of that size (and composition). Alternatively, a particle that is much larger but which passes relatively far from the beam axis yields a pulse height that could actually be the same, depending on its size and trajectory. Even though the large particle is able to intercept a much larger area of incident illumination than the small one, the average intensity incident on it is smaller than the intensity incident on the small particle. Hence, the resulting pulse height could turn out to be the same as that produced by the small particle. Obviously, there are an infinite number of pairs, $\{d, |x|\}$, of particle diameters and minimum beam-trajectory distances that can give rise to the same pulse height. The particle diameter, d, and the resulting pulse height, $\Delta V_{LE}$, are effectively "decoupled" from each other. This is the problem of "trajectory ambiguity" alluded to above in the Description of Related Art, which for more than twenty years has motivated the search for new light-scattering based schemes for particle size determination using gaussian beams.

The effects of trajectory ambiguity described above would appear to render the new narrow-beam sensor relatively useless for demanding particle-sizing applications. Happily, such a pessimistic assessment is not justified. The resolution of the new LE-type sensor is poor only if one insists on using the new method to obtain the size of a single particle, or a relatively small number of particles. As will be demonstrated, the apparently poor size resolution associated with the new sensor can be restored to a very acceptable level by means of appropriate mathematical deconvolution of the pulse-height data. The resulting dramatic improvement in the effective sensor resolution is possible by virtue of the fact that the new sensor is intended to be exposed to a large, statistically significant number of particles of every relevant diameter, or range of diameters, contained in the sample of interest. This is the circumstance that renders the new sensing method very useful for particle size analysis, in sharp contrast to the situation that holds for "contamination" applications. There, the sensor is exposed to relatively small numbers of particles of any given size, for which statistical significance is often not achieved.

The "raw" response of the new focused-beam sensor, like its conventional SPOS predecessor, consists of the pulse height distribution (PHD)—a histogram of particle "counts" vs pulse height, $\Delta V_{LE}$. The pulse-height scale is typically divided into a relatively large number (e.g. 32, 64 or 128) of "channels," or "bins," each of which encompasses an appropriately narrow range of pulse height voltages, thus defining the voltage resolution of the PH). It is usually convenient to establish channels that are evenly spaced on a logarithmic voltage scale. Measurement of a new pulse causes the number of particle counts stored in the appropriate pulse height channel in the histogram to be incremented by one. Data are ideally collected from the particle suspension of interest for a sufficiently long time that the resulting PHD becomes statistically reliable, and thus smooth and reproducible. This means that the number, $N_I$, of particle counts collected in the I-th pulse-height channel is statistically significant, dominating the fluctuations due to statistical "noise," for all I, e.g. for $1 \leq I \leq 128$, in the case of 128 channels. Assuming Poisson statistics, this means that $N_I >> \sqrt{N_I}$, for all I.

Figure 4:
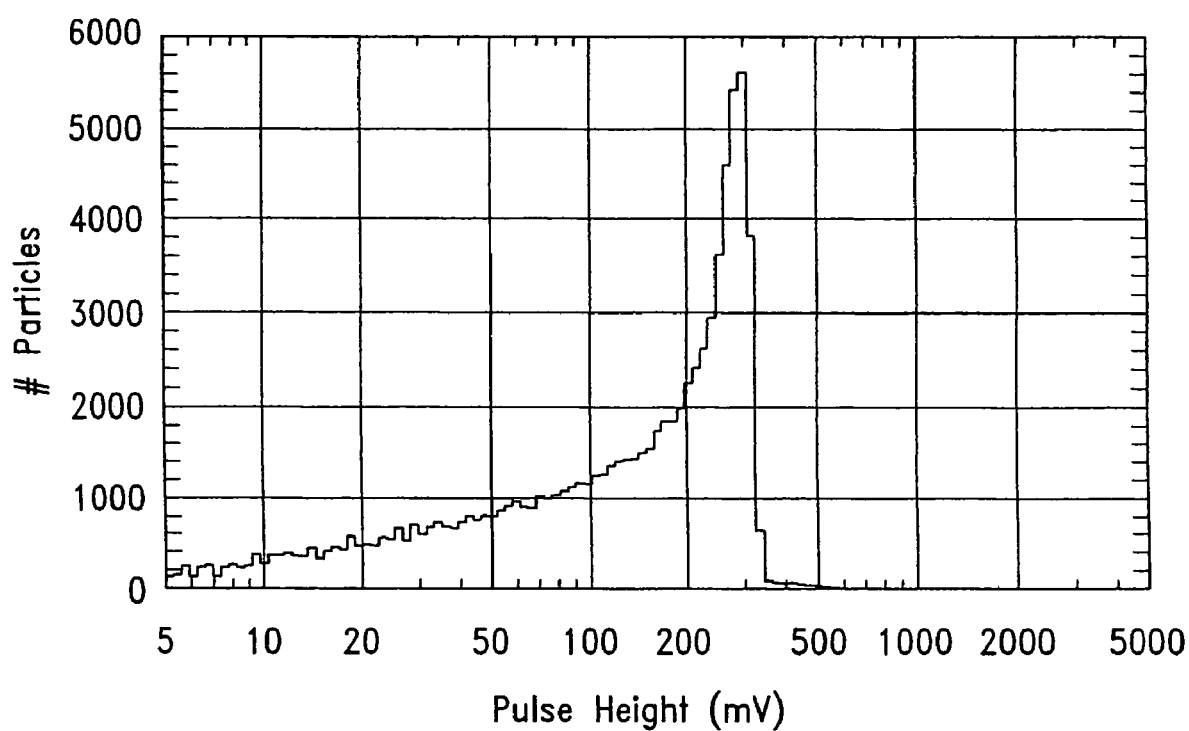
FIG. 4 shows a typical pulse height distribution (PHD) obtained from the LE-type sensor of FIG. 3, using uniform polystyrene latex (standard) particles of diameter 1.588-μm.

A representative example of a PHD produced by the new LE-type sensor is shown in FIG. 4. The sample consisted of a 10,000:1 (by volume) aqueous dilution of a stock suspension of uniform polystyrene latex particles (Duke Scientific, Palo Alto, Calif.) of diameter=1.588 micrometers (μm). The PHD was generated by a total of 83,702 particles during a data collection time of 48 seconds. The flow rate utilized was 20 ml/min, resulting in a total analyzed sample volume of 16 ml and an average pulse rate of 1,744/sec. The concentration of the stock suspension was 1% by weight. Given a particle volume, $V_P$, equal to $2.10 \times 10^{-12}$ cm$^3$, and a density, $\rho$, of 1.05, this is equivalent to a number concentration of $4.54 \times 10^9$ per ml. After dilution, the particle concentration flowing through the sensor was $4.54 \times 10^5$/ml. This value is much higher—indeed, more than 50 times higher—than the concentration levels that are typically recommended for conventional LE-type sensors (i.e. to avoid significant coincidence effects). In fact, this concentration could have been increased substantially (at least 2-fold) without introducing significant distortion in the shape of the PHD due to coincidence effects.

Such high levels of particle concentration are possible only because the new sensor responds to only a small fraction of the total number of particles passing through it. Using the example of FIG. 4, the total number, $N_T$, of particles that passed through the sensor was $N_T \approx 4.54 \times 10^5$/ml$\times$16 ml, or $7.26 \times 10^6$. The number, $N_P$, of particles to which the sensor actually responded, thus yielding the PHD of FIG. 4, was 83,702. Hence, the fraction, $\phi_d$, of particles of diameter d=1.588 μm that actually contributed to the measured PHD, defined by $\phi_d = N_P/N_T$, was $1.15 \times 10^{-2}$, or 0.0115. Fraction $\phi_d$ is referred to as the "sensor efficiency."

The fact that the sensor efficiency is so relatively small is not surprising. In the case of a tightly focused beam, the width, a, of the flow channel is invariably much larger than the nominal width, $2w$, of the focused beam. Therefore, most of the particles passing through the sensor are exposed to negligible levels of light intensity, because their trajectories are located so relatively far from the beam axis—i.e. $|x|>>w$. Consequently, only a small fraction of the total number of particles are able to "block" enough light to give rise to detectable pulses, relative to the prevailing noise level. The great majority of particles pass undetected through the sensor.

While this limitation may appear to be serious, in practice it is of little concern, for two reasons. First, the fraction, $\phi_d$, of particles that produce detectable, measurable pulses will be fixed for a given sensor width, a, even though the value changes with particle diameter, d. Second, the new sensing method is intended for use in determining the particle size distribution (PSD) for samples that, by definition, are highly concentrated to begin with. Even following dilution, if required, the concentration of particles of any given size (i.e. within any (narrow) size range) is, by definition, relatively high. Assuming a suitable flow rate and data collection time, the resulting PHD will possess an acceptable signal/noise ratio, with a low level of statistical fluctuations. Hence, even though only a small fraction of the available particles will contribute to the raw data, the resulting PHD will be representative of the much larger number of particles in the sample that are ignored. Therefore, a reliable and accurate PSD, representative of the entire sample, will be obtained from the "inefficient" new sensor.

It is useful to estimate the width, $2w_d$, of the imaginary, approximately cylindrical volume surrounding the beam axis that represents the effective OSZ for particles of diameter d. By definition, any particle that passes through this imaginary region will give rise to a pulse that can be detected and quantified (i.e. by its pulse height). This width, $2w_d$, is directly related to the sensor efficiency, $\phi_d$, and is defined by $$2w_d = \phi_d \times a \qquad (8)$$

The PHD shown in FIG. 4 was obtained from a sensor having a flow channel width of 2 mm, or 2000 μm. From Equation 8, one therefore obtains $2w_d$=23 μm for the case of 1.588-μm particles. The estimated beam width, $2w$, for this same sensor was between 10 and 11 μm (discussed below). Hence, the effective width of the cylindrical-shaped OSZ, in the case of 1.588-μm particles, is slightly larger than twice the nominal width of the gaussian beam.

Several additional features of the PHD shown in FIG. 4 are noteworthy. First, as a consequence of the fact that the particle trajectories span a large range of |x| values, passage of uniform particles through the sensor indeed results in a PHD containing a wide range of pulse heights. In this case, these range from the threshold of individual pulse detection (dictated by the prevailing r.m.s. noise level), roughly 5 millivolts (mV), to a maximum of approximately 326 mV for the nominal "end" of the distribution. (This excludes a small number of "outlier" pulses, due to agglomerates and over-size primaries that extend to 500 mV). Given the uniformity of the particles, this 65-fold range of pulse heights can only be ascribed to differences in particle trajectory. (To a first approximation, one can neglect variations in the beam width over the depth of the flow channel, as discussed earlier.)

Second, as expected, the PHD is highly asymmetric, skewed greatly in the direction of smaller pulse heights. Clearly, there are many particle trajectories that sample a large range of |x| values (and, hence, beam intensities), but only relatively few that probe the central portion of the gaussian profile, where the intensity is substantially uniform. The PHD exhibits a broad, smooth upswing in the number of particles with increasing pulse height, accelerating to a relatively sharp peak, followed by a dramatic decline to the baseline, representing zero pulse events. This sharp "cut-off" at the upper end of the distribution defines the maximum pulse height, referred to hereafter as $^M\Delta V_{LE}$. In the case of the PHD shown in FIG. 4, this value is approximately 326 mV. The counts collected at this maximum value represent particles that passed through, or very close to, the center of the beam—i.e. trajectories with x≈0—where the fraction of total incident light flux "blocked" by the particles is the largest value possible. The counts collected in smaller pulse height channels represent particles that passed further from the beam axis; the greater parameter |x|, the smaller the resulting pulse heights.

Figure 5:
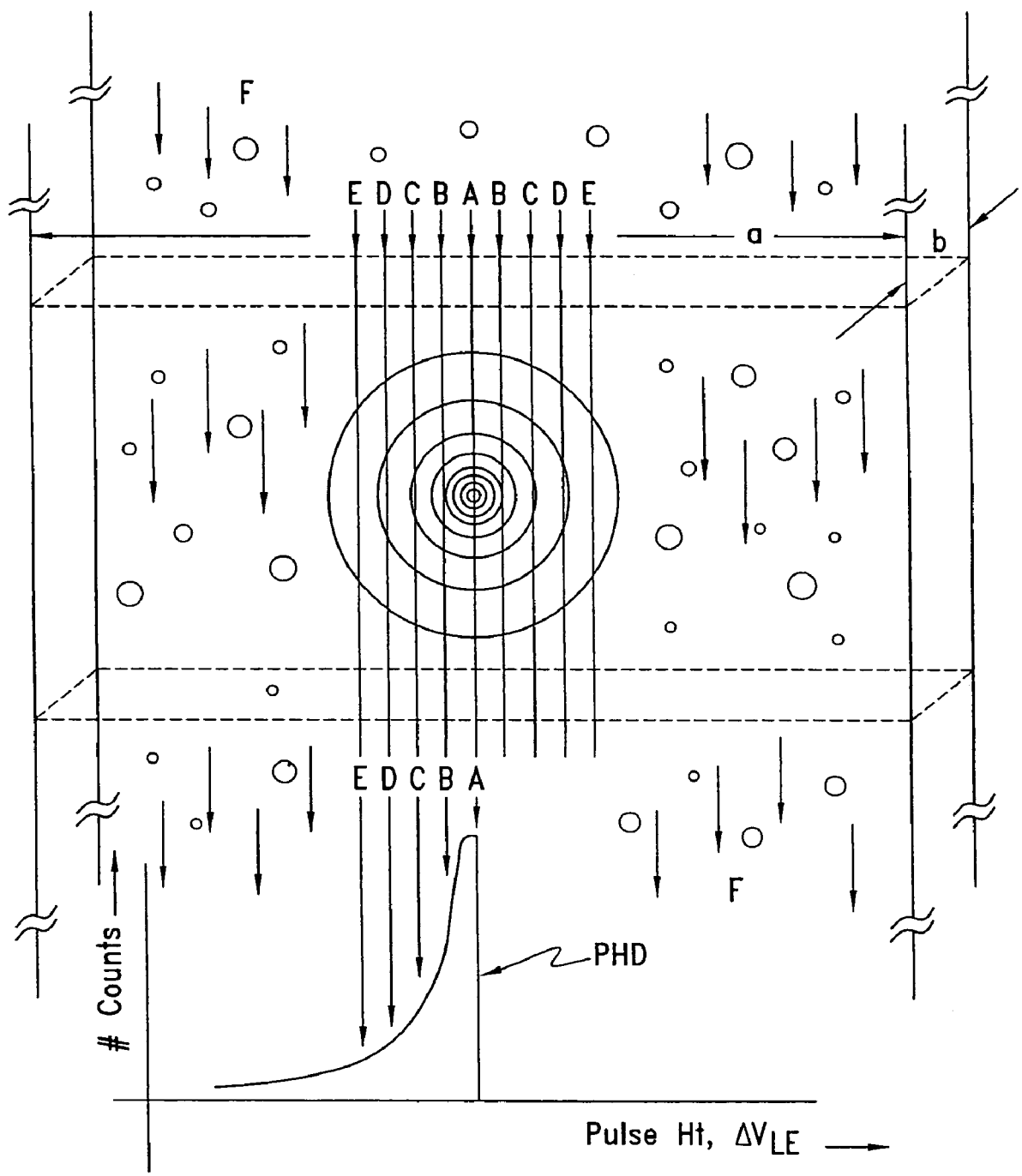
FIG. 5 is a schematic diagram showing the relationship between particle trajectory and the resulting PHD, for an incident light beam with a non-uniform, gaussian intensity profile.

The relationship between the particle trajectory and the resulting pulse height is shown schematically in FIG. 5. Trajectory "A" gives rise to extinction pulses having the maximum pulse height, $^M\Delta V_{LE}$, immediately preceding the upper cut-off of the PHD. Trajectories "B," "C," "D" and "E" located progressively further from the beam axis, give rise to pulses with correspondingly lower pulse heights and progressively lower numbers of particle counts. Eventually, the number of particle counts per channel approaches zero, as the pulse height reaches the detection limit (≈5 mV), at the lower left-hand corner of the PHD plot shown schematically in FIG. 5.

As discussed earlier, the reproducibility of the PHD should depend only on the degree to which the number of counts contained in the various channels are large compared to statistical fluctuations. Therefore, the "reliability" (i.e. the smoothness and reproducibility) of the PHD should depend on the total number of particles counted during a measurement. For a given particle size there will obviously exist a minimum number of pulses that should be counted and analyzed, below which the PHD should be expected to exhibit significant, irreproducible "structure" from one measurement to the next, due to statistical noise. Again, the PHDs produced by the new sensor have meaning only to the extent that relatively large, statistically meaningful numbers of particles of the same size are detected during the data collection period. Only if this is true can one expect to obtain optimal, reproducible PHD results, and correspondingly accurate, representative particle size distribution (PSD) results derived from the latter using the methods discussed below.

In the case of the 1.588-μm latex standard particles used to generate the PHD shown in FIG. 4, a second measurement of a fresh 16-ml volume of the same stock suspension yielded a very similar PHD result, with 83,327 particles detected. The difference in the total number counted lies well within the square root of the average value (289). One can tentatively conclude that the number of particles sampled by the sensor for each measurement was sufficiently large to yield PHDs of acceptable reproducibility (confirmed by overlaying two or more PHDs).

Figure 6:
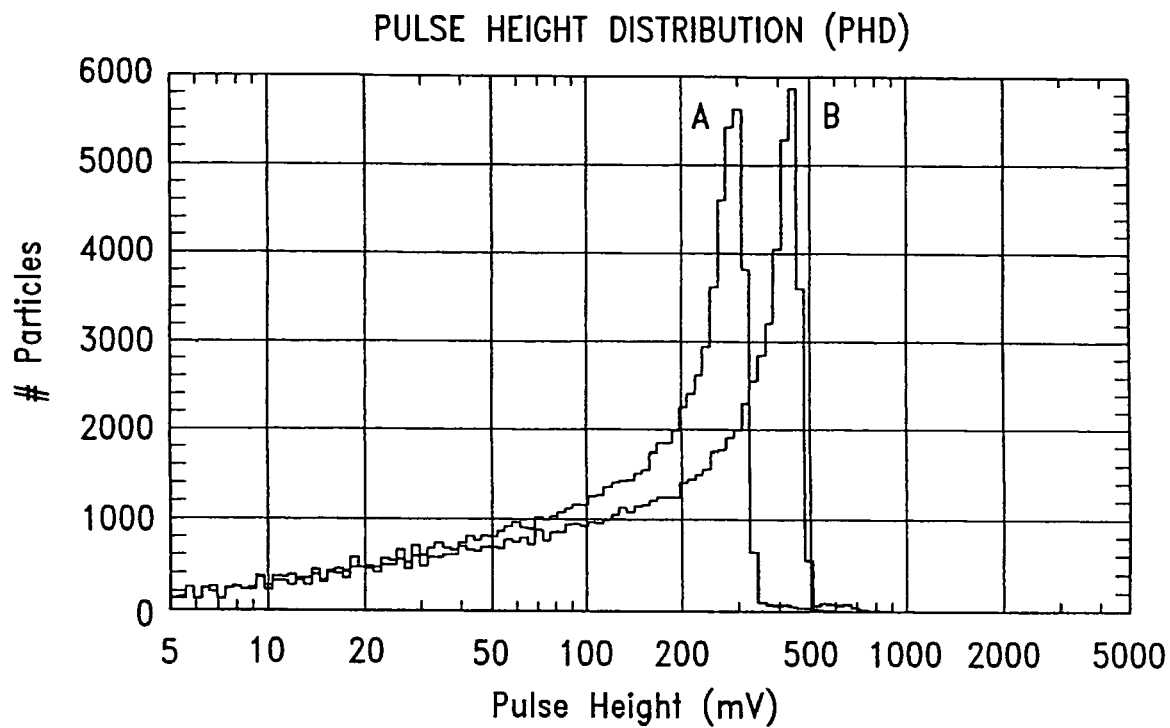
FIG. 6 compares the PHDs obtained for 1.588-μm and 2.013-μm polystyrene latex (standard) particles using the new LE-type sensor.

From the preceding discussion it is clear that exposing the new sensor to larger particles should yield a PHD that is shifted to larger pulse heights. Specifically, the maximum pulse height, $^M\Delta V_{LE}$, corresponding to particle trajectories passing through, or very close to, the beam axis, must increase. This is indeed the case, as shown in FIG. 6, comparing PHD "A," obtained for d=1.588 μm, with PHD "B," obtained for d=2.013 μm. The latter consisted of a 2000:1 dilution (vol) of a stock suspension of polystyrene latex spheres (Duke Scientific) of concentration 0.45% (wt), equivalent to $1.0 \times 10^9$ particles/ml. PHD "B" was generated by a total of 83,481 particles, using the same data collection time and flow rate utilized in FIG. 4 and thus resulted in an average count rate of 1,739/sec.

The shape of PHD "B" (2.013-μm) is clearly very similar to that of PHD "A" (1.588 μm). The only significant difference is the value of the maximum pulse height, $^M\Delta V_{LE}$, which now occurs at 482 mV. The peak of PHD "B" appears to be somewhat sharper (i.e. narrower) than that observed for the smaller particles. However, this assessment is largely a matter of perception, given the fact that the pulse height channels have equal width on a logarithmic voltage scale. Hence, a channel located at a higher pulse height value (e.g. 482 mV) will contain a wider voltage range than a channel located lower on the scale (e.g. 326 mV).

To a first approximation, the PHD for d=2.013 μm can be derived from the PHD for d=1.588 μm simply by "stretching" the latter in linear fashion along the x-axis to higher pulse-height values, so that the maximum cut-off "edges" of the two PHD curves coincide. This action is accomplished by applying a multiplicative factor to the pulse height values associated with each channel of PHD "A." This factor is equal to the maximum pulse height, $^M\Delta V_{LE}$, for PHD "B" divided by the corresponding value for PHD "A"—i.e. 482/326=1.48.

Figure 7:
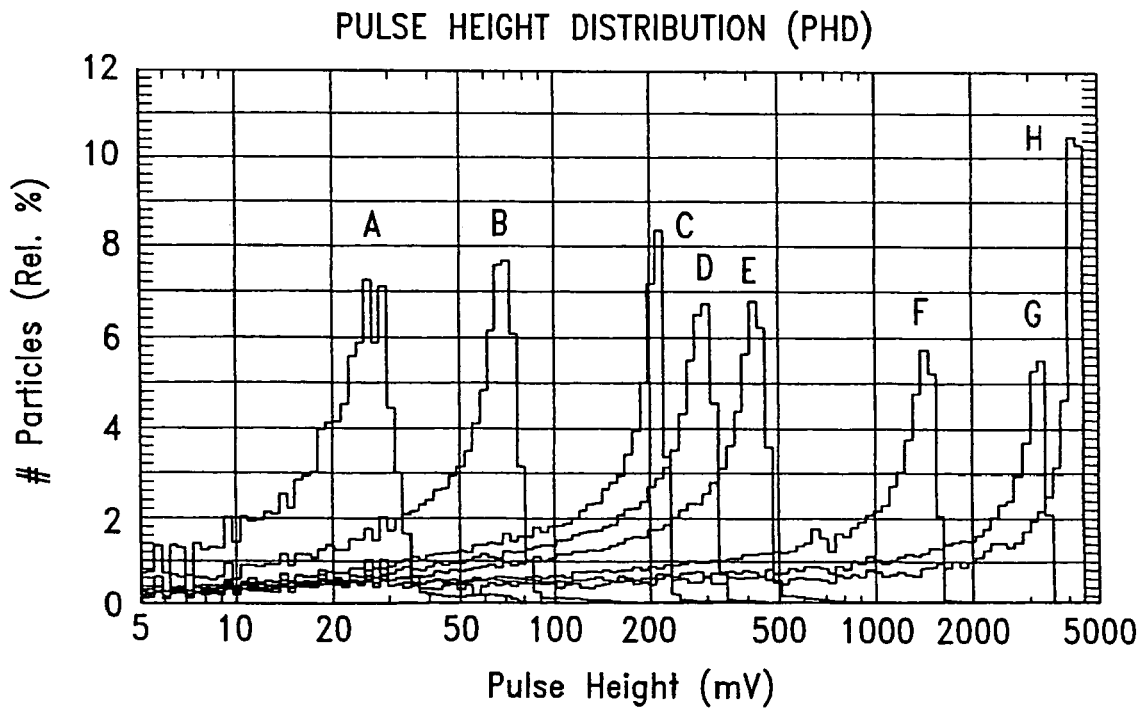
FIG. 7 compares the PHDs obtained using the new LE-type sensor for uniform polystyrene latex (standard) particles of eight different sizes: 0.806-μm, 0.993-μm, 1.361-μm, 1.588-μm, 2.013-μm, 5.03-μm, 10.15-μm and 20.0-μm.

It is instructive to compare the PHDs obtained for a series of uniform particle size populations, encompassing a wide range of particle diameters. Representative results for the individual PHDs obtained for statistically significant numbers of polystyrene latex standard particles ranging in diameter from 0.806 to 20.00 μm are shown in FIG. 7 and summarized in Table I. (Note: PHDs of reduced, but acceptable, signal/noise ratio can be obtained for particles as small as approximately 0.6 μm using the same sensor and optical parameters.) Each of the PHDs shown in FIG. 7 was obtained by measuring 16-ml of appropriately diluted stock suspension, using a flow rate of 20 ml/min, as before. The maximum pulse heights, $^M\Delta V_{LE}$, are expressed as absolute (mV) values and also as percentages of 5 volts, or 5000 mV (the "baseline" voltage, $V_0$). This is the maximum possible pulse height, representing 100% extinction of the incident light flux. Each PHD in FIG. 7 is plotted as a relative-number distribution—i.e. the number of counts in each channel divided by the total number of counts collected for the sample in question.

As discussed above, any given PHD (e.g. "C") in FIG. 7 can be approximated by taking the PHD for the nearest smaller size (i.e. "B") and shifting it to larger pulse-height values using an appropriate multiplicative factor, $^M\Delta V_{LE}$ ("C")/$^M\Delta V_{LE}$("B"). This is possible because of the self-similarity of the PHDs. This procedure is very useful, as it can be used to compute, rather than measure, a reasonably accurate PHD for any arbitrary particle size lying between sizes for which PHDs have already been measured. This operation is an important ingredient in the mathematical procedure used to "deconvolute" measured PHDs, as will be discussed below.

Figure 8A:
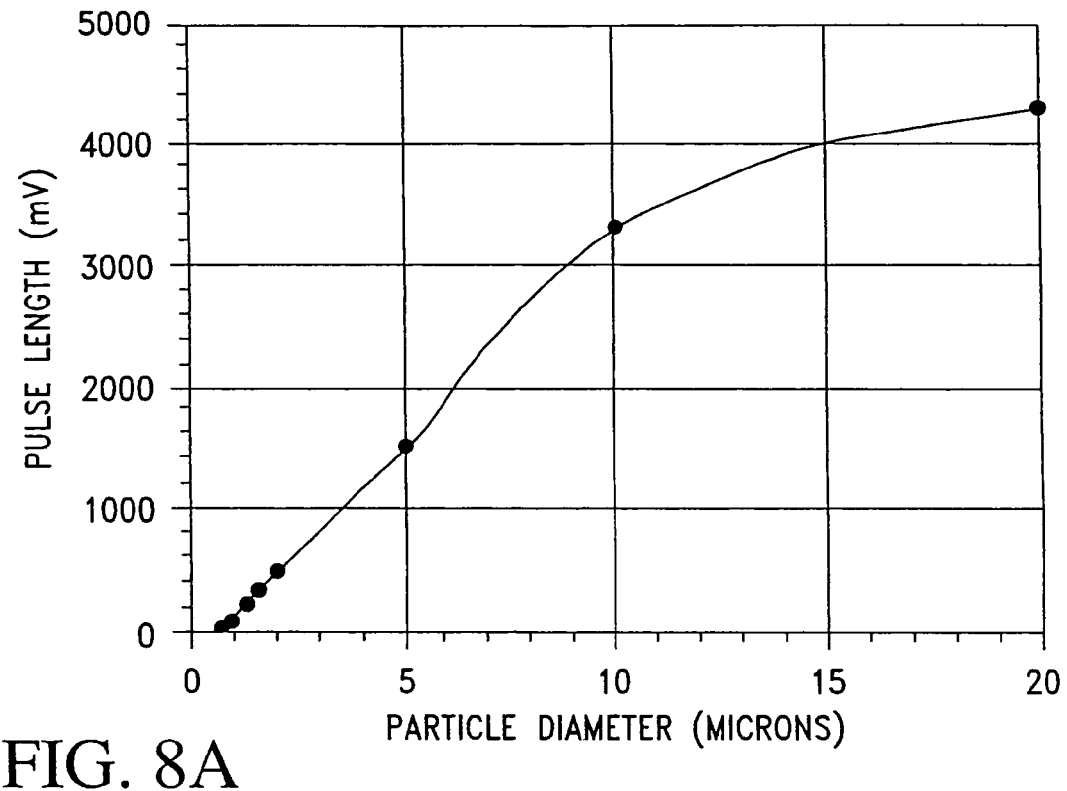
FIG. 8A shows the maximum measured pulse height versus particle diameter for the eight polystyrene latex (standard) particle suspensions displayed in FIG. 7.

It is clear from FIG. 7 (and Table I) that the PHD produced by the new sensing method for uniform-size particles is able to detect relatively small changes in particle diameter. The maximum pulse height, $^M\Delta V_{LE}$, increases significantly with increasing particle size over a relatively wide (i.e. >25-fold) size range, as shown in FIG. 8A. Indeed, one can make the seemingly contradictory argument that the size "resolution" of the new sensing method is, in fact, relatively high, notwithstanding the fact that the PHD produced by particles of a given size is broad and, by definition, lacking in resolution. This point of view will become evident below in connection with the procedures used to "invert," or deconvolute, the PHD data obtained from a mixture of particles of different sizes, in order to obtain the final object of interest, the PSD. For the time being, it is sufficient to point out that the results of FIG. 7 demonstrate that a relatively small change in the particle size yields a significant, measurable difference in the voltage associated with $^M\Delta V_{LE}$. As will be seen below, this characteristic of the signal response is a necessary (although not sufficient) condition, permitting the deconvolution procedure to be effective in extracting a PSD of relatively high resolution from the measured PHD.

Figure 8B:
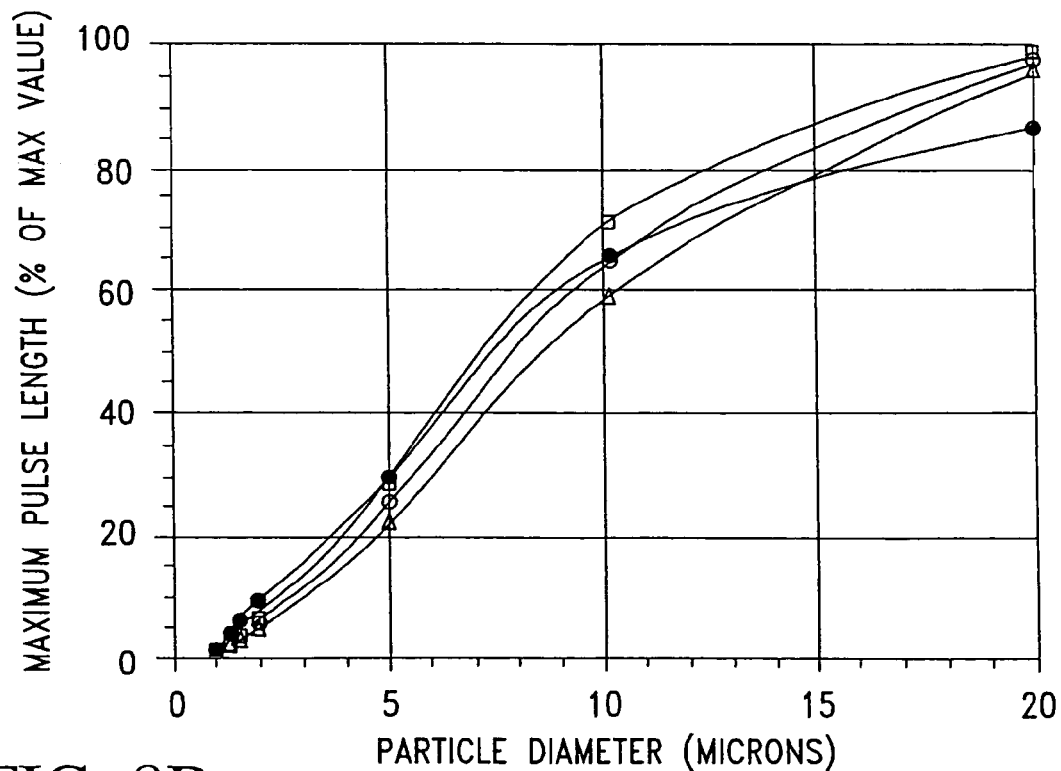
FIG. 8B compares theoretical predictions (perfect extinction, gaussian beam) with experimental results (FIG. 8A, solid circles) for the maximum pulse height (expressed as a percentage of 100% extinction) versus particle diameter, theoretical curves being shown for beam widths ($1/e^2$) of 10-μm (open squares), 11-μm (open circles) and 12-μm (open triangles)

It is instructive to compare the measured light-blocking ratios—i.e. $^M\Delta V_{LE}$ expressed as a percentage of the maximum saturation value, $V_0$, of 5 Volts—with the values predicted by a naive light-blockage model. This assumes that a particle effectively removes 100% of the light incident on it, over a circular disk of area $\pi d^2/4$, regardless of its size, ignoring the contribution to the LE signal made by light scattering, which dominates at sufficiently small sizes. This comparison is shown in FIG. 8B, with three sets of model calculations, assuming gaussian beam widths of 10-μm (open squares), 11-μm (open circles) and 12-μm (open triangles). (These values are consistent with an independent measurement of the beam waist using a moving-slit beam profiler: 12±2 μm.)

As can be seen in FIG. 8B, the measured values of $^M\Delta V_{LE}$ (solid circles), expressed as percentages of the maximum value possible (5 Volts), for d=5.03- and 10.15-μm are in closest agreement with assumed beam widths of 10-μm (open squares) and 11-μm (open circles). An average value of 10.5-μm therefore represents the best estimate. At the upper end of this 5-10 μm size range, simple light refraction should dominate the light extinction phenomenon. Below 5-μm, the agreement is not as good, deteriorating progressively as the particle size decreases. The theoretical values in this region should indeed be lower than the measured ones, because the naive model employed ignores the effects of light scattering. The smaller the particle, the greater the relative contribution of scattering to the overall LE signal and hence the greater the extent of the discrepancy between theory and measurement, as observed.

Given an effective beam width of approximately 10.5-μm, the value found for $^M\Delta V_{LE}$ should approach "saturation" for particles significantly larger than this size. Specifically, there is a diminishing fraction of total light flux in the beam remaining to be blocked by a 20-μm particle that has not already been extinguished by a 10-μm particle passing through the center of the beam. Hence, the slope of $^M\Delta V_{LE}$ vs d, whether measured or calculated, "rolls over" with increasing d, asymptotically approaching 100% for d values larger than about 10-μm. At the small-diameter end of the scale, the slope of $^M\Delta V_{LE}$ vs d decreases with decreasing d, owing to the diminishing contribution of scattering to the LE signal. Therefore, the shape of the curve of the light-blocking ratio over the entire size scale resembles a sigmoid. Unfortunately, the agreement between the measured and calculated light-blocking ratios at d=20 μm is not nearly as good as that obtained for 5.03 and 10.15-μm. The calculated ratios for beam widths of 10- and 11-μm are 99 and 98%, respectively, while the measured ratio is "only" 90%. The likely source of this discrepancy is an imperfect beam intensity profile, deviating significantly from the ideal gaussian shape assumed by the model. The existence of imperfect optical elements, incomplete beam circularization and possible misalignment can result in an asymmetric pattern of lower intensity light regions surrounding the high intensity region of the beam. Light rays corresponding to these non-ideal regions can reach the detector even if most of the rays associated with the main beam are effectively blocked by a large particle. Hence, passage of a 20-μm particle through the beam axis results in extinction of less than 100% of the incident light.

It is important to appreciate the dependence of the sensor efficiency, $\phi_d$, on the particle diameter, d. The larger the particle, the larger the fraction of incident light flux that it is able to intercept and "block." Hence, a large particle can be detected further from the beam axis than a smaller particle, which may vanish, even though it follows the same trajectory as the larger particle, or even one closer to the beam axis. Therefore, it should be evident that the fraction of particles that are detected and contribute to the PHD, defined as $\phi_d$, increases with increasing particle size (excluding the effects of non-monotonic variations of the scattering intensity with particle size, described by Mie scattering theory).

Figure 9:
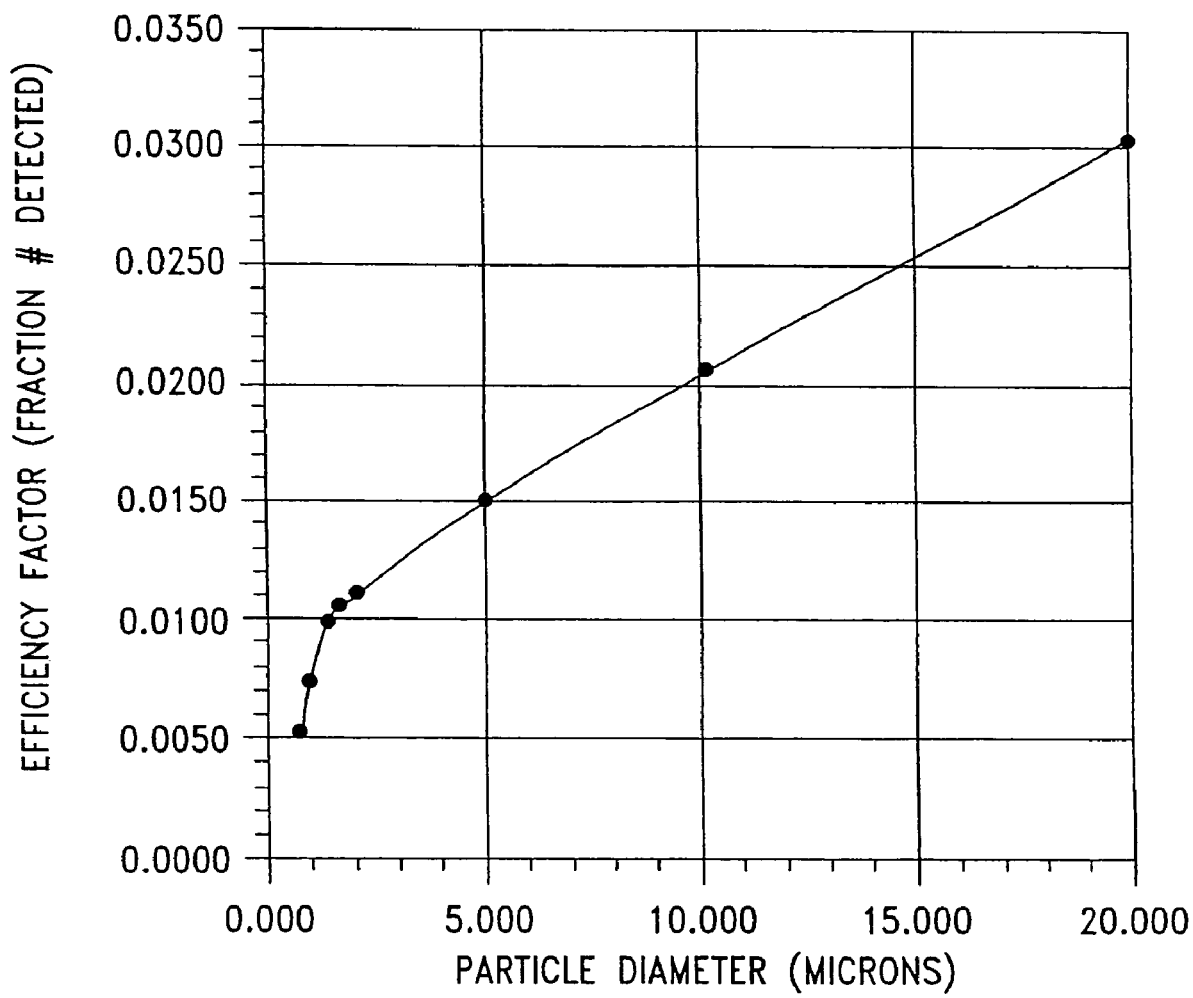
FIG. 9 shows the dependence of the measured sensor efficiency, $\phi_d$, as a function of particle diameter, d, over the range 0.806- to 20.0-μm.

FIG. 9 shows representative values of $\phi_d$ vs d obtained for polystyrene latex particles in the size range of 0.806- to 20.0-μm, based on the results shown in FIG. 7 and Table I. In order to calculate the various $\phi_d$ values, it was necessary to determine independently the total number of particles that passed through the sensor during measurement of the respective PHDs. These values were determined by measuring a known volume of each suspension, diluted by a suitable (much larger) factor, using a conventional sensor (based on a combination of LE and LS methods), having approximately 100% counting efficiency. The value of $\phi_d$ for each diameter, d, was obtained by dividing the number of particles counted during a PHD measurement by the total number of particles present in the volume of suspension that flowed through the sensor.

As shown in FIG. 9, the value of $\phi_d$ decreases monotonically with decreasing particle diameter, from 0.030 for d=20.0-μm to 0.0053 for d=0.0806-μm, representing a nearly 6-fold decrease. The effective width of the OSZ shrinks with decreasing particle diameter, as expected. The efficiency of the new sensor "rolls over" and declines precipitously toward zero with increasing slope when the particle size falls below about 1.5-μm. This feature simply confirms the inability of the LE method, even with a beam width as small as 10-μm, to function effectively when the particle size is sufficiently small. This is the point at which it becomes useful to employ the LS method (discussed below). However, it is also clear from FIG. 7 that the PHD results possess good signal/noise ratios for particle diameters as small as 0.8-μm (or smaller.

Because $w_d$ is proportional to $\phi_d$, it is clear that the width of the effective OSZ increases with the particle diameter in the same way that $\phi_d$ increases with d, as shown in FIG. 9. As discussed above, the influence of the light beam extends further across the flow cell along the x-axis the larger the particle in question. This can be considered to be a "nonlinear" response of the new sensor, in which its efficiency in general increases with particle diameter. This behavior will be seen to have important implications for the procedure of obtaining the desired PSD by deconvolution of the PHD, especially for samples containing a broad range of particle sizes.

From Equation 8 it is clear that decreasing the width of the flow channel can increase the sensor efficiency for all diameters. This would allow a larger (albeit still small) fraction of the particles to pass through the region of influence of the light beam—i.e. the effective OSZ. Hence, in principle the sensor efficiency for particles of all sizes can be improved simply by decreasing dimension "a." However, in practice there are two reasons why it may not be useful or advisable to carry out such an "improvement."

First, a reduction in dimension "a" implies a corresponding reduction in the cross-sectional area of the flow channel, $A_F=a \times b$. However, there is a practical limit on how small this area can be without presenting excessive impedance to the flow of the sample suspension. Also, reduction in this dimension can give rise to errors in the measured pulse heights, owing to the high resulting velocity of the particles. For a given flow rate, F, the velocity of the particles passing through the OSZ varies inversely with dimension "a" (Equation 4). If the velocity is too high, the resulting signal pulses will become correspondingly narrower in time, potentially leading to errors (i.e. a reduction) in the measured pulse heights associated with the bandwidth of the amplifier means. One could avoid this problem by reducing the flow rate. However, this action would reduce the statistical accuracy of the resulting measured PHD—i.e. proportionately fewer particles of each relevant size would be detected during a given period of time.

Alternatively, one might consider increasing the depth, b, of the flow channel as a means of compensating for a decrease in the width, a, in order to keep quantity $A_F$ substantially constant and thereby restore the particle velocity to an acceptable value. However, this action would produce two negative consequences. First, the volume of the effective OSZ for each particle size would increase in proportion to the increase in "b" (assuming no change in the effective width of the OSZ). The coincidence concentration would decrease by the same factor as the increase in "b," thus negating the advantage of the new sensor in being able to accommodate relatively concentrated suspensions. Second, a significant increase in "b" would result in reduced resolution of the PHD and the resulting PSD, owing to greater variation in the width of the beam (assuming that it is focused) and effective OSZ over the depth of the flow channel. Broadening of the ideally sharp "cut-off" of the PHD at the maximum pulse height, $^M\Delta V_{LE}$, would result in reduced resolution of the PSD obtained by deconvolution of the PHD.

Therefore, it is not realistic to increase greatly the sensor efficiency by one or more of the means reviewed above. Fortunately, this "limitation" in performance is, in practice, not the shortcoming that it appears to be. In fact, in at least one important respect, it is a virtue. First, as discussed above, the new sensor is intended to be exposed to relatively concentrated samples. The small fraction (e.g. 0.005 to 0.03, from FIG. 9) of particles detected still translates to large absolute numbers of particles of each size that contribute to the PHD. Second, and more important, the relatively low sensor efficiency provides a significant advantage for applications requiring predilution of the starting sample suspension. The coincidence concentration values for the new sensor are larger than the corresponding value achieved by a conventional LE-type sensor by roughly a factor of $1/\phi_d$—i.e. approximately 30 to 200 times greater, based on the values shown in FIG. 9. (This comparison assumes that the beam width, $2w$, and flow channel dimensions, a and b, are the same for the traditional LE-type sensor.) Therefore, a concentrated suspension needs to be diluted much less—i.e. a factor $1\phi_d$ less—than what is required by a conventional sensor. Consequently, the diluent fluid (e.g. water, organic solvent, etc.) can be correspondingly "dirtier" (with respect to contaminant particles) than the diluent fluid normally used. In practice, this is an important advantage.

Figure 10:
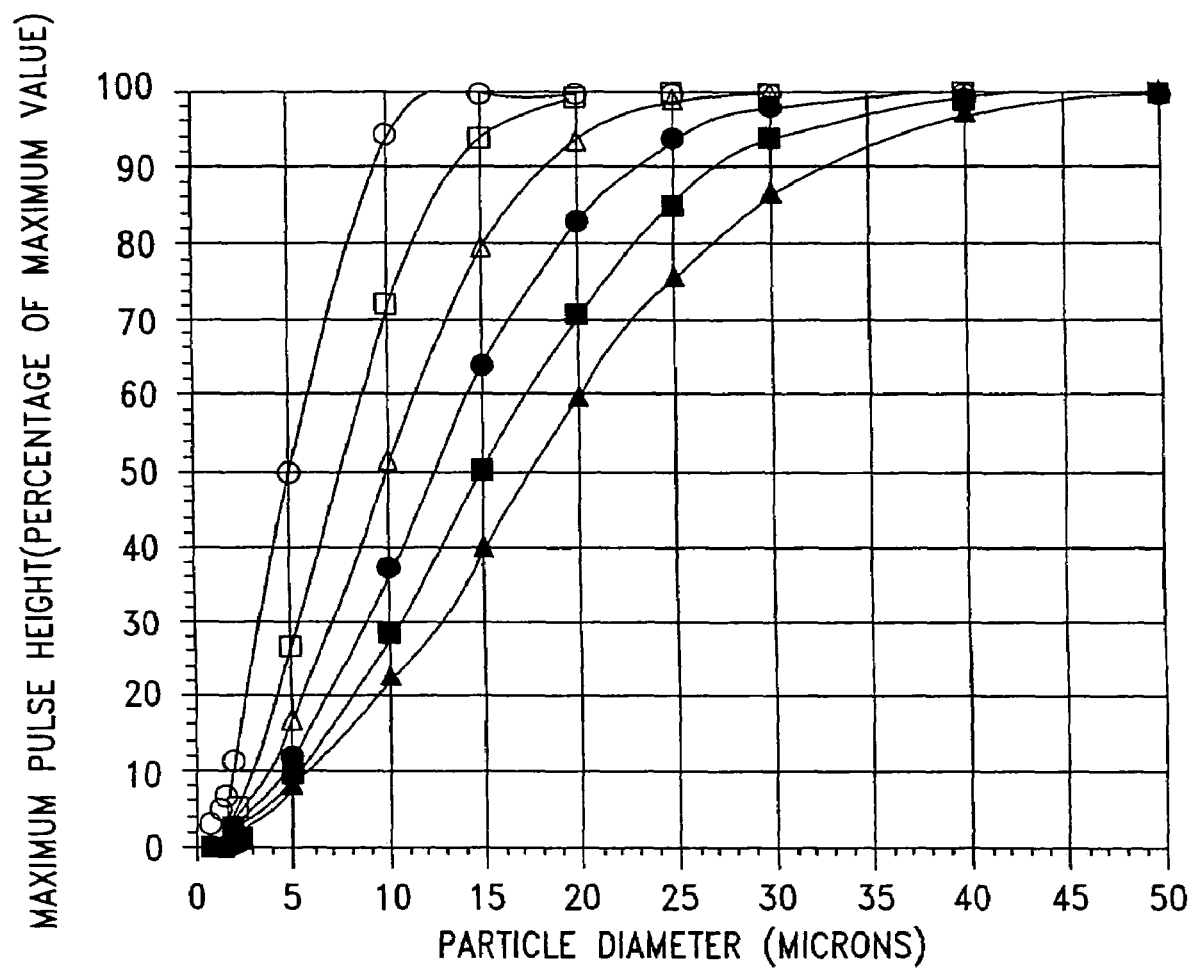
FIG. 10 shows the theoretical predictions (perfect extinction, gaussian beam) for the maximum pulse height (expressed as a percentage of 100% extinction) versus particle diameter for various beam widths: 6-μm (open circles), 9-μm (open squares), 12-μm (open triangles), 15-μm (closed circles), 18-μm (closed squares) and 21-μm (closed triangles)

From the previous discussion and the results shown in FIGS. 8A and B, it is evident that the new sensor has diminishing resolution for particle diameters significantly larger than the width of the beam. Here, the term "resolution" refers to the change in $^M\Delta V_{LE}$ for a given (unit) change in particle diameter—i.e. the slope of $^M\Delta V_{LE}$ vs d. At the small end of the size scale, this slope, and hence the resolution, decreases with decreasing d. The threshold for detection of the smallest particles is determined by the smallest pulse height, $\Delta V_{LE}$ that can be measured, given the prevailing noise fluctuations. It should be appreciated that the range of particle diameters over which the new sensing method yields results of acceptable resolution depends on the choice of beam width, all other variables being equal. If the beam width is increased significantly, the region of maximum slope of $^M\Delta V_{LE}$ vs d—i.e. the point of inflection of the curve—will shift to larger particle sizes; the larger the beam width, the larger the shift. The sensor can then be effectively employed to obtain PSDs with acceptable resolution for larger particles. In summary, the PHD response obtained using the new sensing method can be "scaled" to larger particle diameters, based on the choice of beam width. The influence of the beam width on the calculated sigmoidal curves of $^M\Delta V_{LE}$ vs d (assuming 100% light extinction) is shown in FIG. 10. The beam widths utilized include 6-μm (open circles), 9-μm (open squares), 12-μm (open triangles), 15-μm (closed circles), 18-μum (closed squares) and 21-μm (closed triangles). The range of acceptable resolution, corresponding to maximum pulse heights in the range of 10 to 90% of saturation, in the last case has shifted to 5-30 μm.

Conversely, if the beam size is reduced significantly, the point of maximum slope of $^M\Delta V_{LE}$ vs d will shift to lower diameters. However, it should be appreciated that there is not a correspondingly significant reduction in the minimum size of particles that can be detected. In theory, the value of $^M\Delta V_{LE}$ for a given (small) particle diameter will increase with decreasing beam width. In practice, however, there are limitations on the improvement in performance that can be achieved by a new LE-type sensor at the low end of the particle size scale. First, there is a limit, imposed by diffraction theory, on how small a beam can be achieved. At this size—in practice, 3-5 μm—the depth of field of a focused beam will be very narrow, requiring the use of a prohibitively thin flow channel in order to obtain the minimal acceptable variation in beam width (and thus OSZ width) over the depth of the channel. Given realistic values for the channel depth (i.e. b>100 μm), to avoid frequent clogging, a significant variation in the beam width over the depth of the channel is unavoidable. This will negatively impact the sharpness of the maximum pulse height cut-off and the resolution of the resulting PSD.

Second, at the small end of the particle size scale the light scattering mechanism will dominate the LE signal. Despite the diminished width of the focused beam, the absolute fraction of the incident light flux effectively removed from the beam will be very small and will decrease with the particle diameter. In theory, the presence of an arbitrarily high background signal level, $V_0$, should not affect the ability of the detector and associated electronic system to detect a pulse of very small height, superimposed on $V_0$. In practice, however, there is a lower limit on the value of $\Delta V_{LE}$ that can be measured, because of fluctuations in $V_{LE}$, due to a variety of "noise" sources associated with the light source, detector, signal-conditioning means and power supply. Contaminant particles in the sample suspension also contribute to fluctuations in the measured signal. When the pulse height falls below a certain value, the pulse effectively disappears—i.e. it is indistinguishable from the fluctuations in $V_{LE}$ caused by these noise sources.

Figure 11:
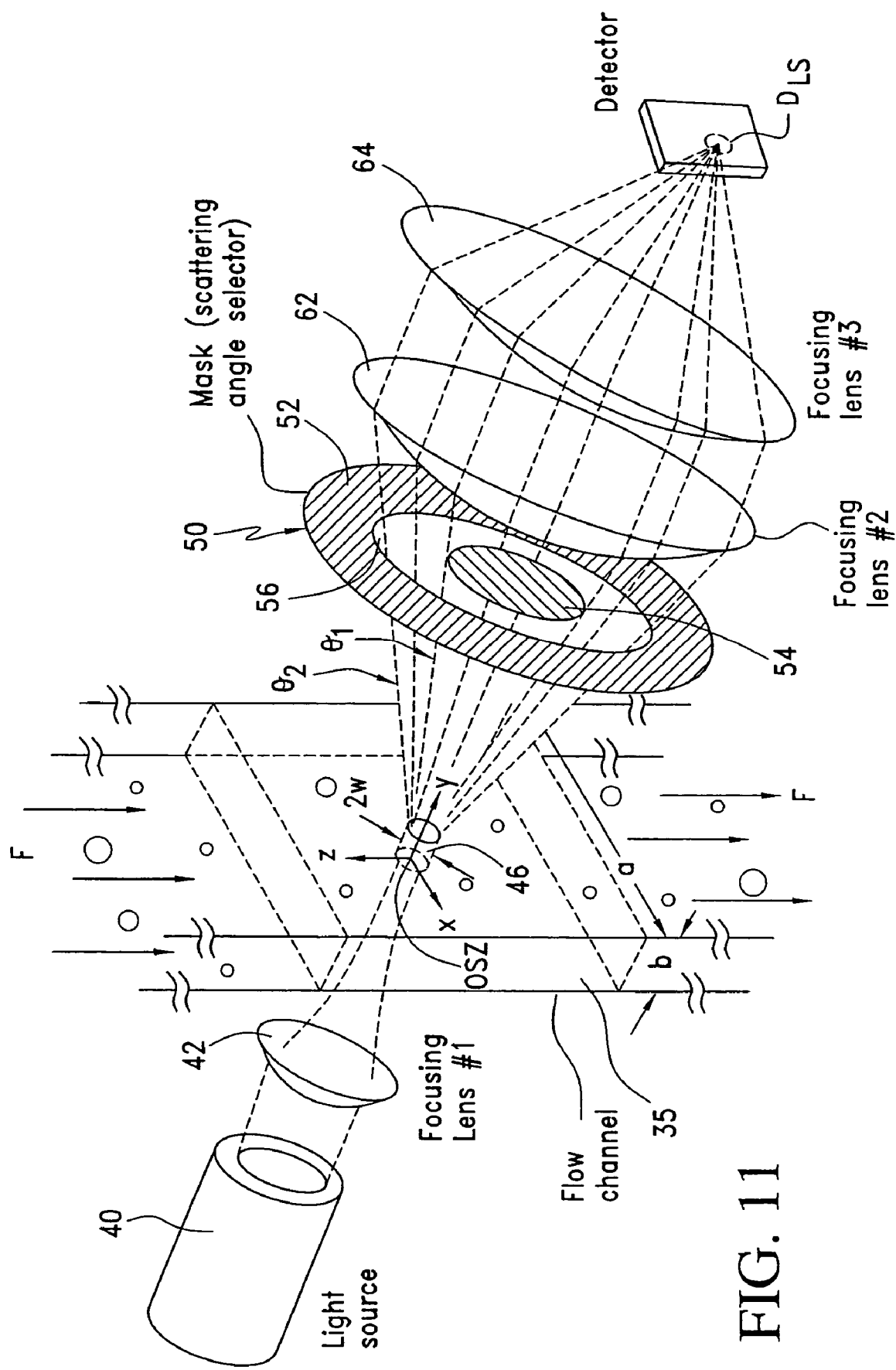
FIG. 11 is a simplified block diagram of the LS-type sensor of this invention, hereinafter the "new LS-type sensor," using a relatively narrow, focused light beam to illuminate particles flowing in a relatively thin flow channel.

Consequently, increasing the sensitivity, using the new method of illuminating particles in a confined space with a narrow focused light beam, requires changing the mode of detection from light extinction to light scattering (LS). The signal that results when a particle passes through the OSZ will then depend on the magnitude and angular distribution of the scattered light intensity produced by the particle over a selected range of scattering angles. The useful signal pulse will no longer be burdened by a high background light level associated with the incident light beam, as is the case for the LE method. The optical scheme that is typically used to implement the new LS measurement is simple, shown schematically in FIG. 11. In many essential respects—i.e., including the light source 40, focusing optics 42 and thin measurement flow channel 35—the apparatus is the same as that used for the new LE-type sensor (FIG. 3). In particular, one typically utilizes a narrow focused light beam 46 with a gaussian intensity profile that passes through the thin dimension, b, of the flow channel—essentially the same scheme as that utilized for the new LE-type sensor. The only way in which it typically might differ is that the width of the beam, $2w$, might be chosen to be smaller than that used for the new LE-type sensor, in order to achieve a higher sensitivity.

The main design difference that distinguishes the new LS-type sensor from its LE counterpart is the addition of a light collection means—typically one or more lenses—in order to gather scattered light rays originating from individual particles passing through the OSZ, created by the incident light beam. The lens system is designed to collect scattered light over a particular, optimal range of angles, typically encompassing relatively small angles of scattering. In the scheme shown in FIG. 11, a mask 50 has been placed in front of the first collection lens. Mask 50 comprises an outer opaque ring 52 and an inner opaque area 54, which form a transparent ring 56. Mask 50 allows only light rays with scattering angles, θ, located within an imaginary annular cone defined by angles $\theta_1$ and $\theta_2$ (i.e. $\theta_1 \theta \leq \theta_2$) to impinge on the first collection lens 62. Typically, this lens is centered on the axis of the incident beam, at an appropriate distance (i.e. its focal length) from the center of the flow channel, causing a portion of the diverging scattered light rays from the OSZ to be captured by the lens and become approximately collimated. A second lens 64 can then be used to focus the resulting parallel scattered rays onto a suitable (small-area) detector DLs. The resulting signal is "conditioned" by one or more electronic circuits, typically including the functions of current-to-voltage conversion and amplification.

Figure 2:
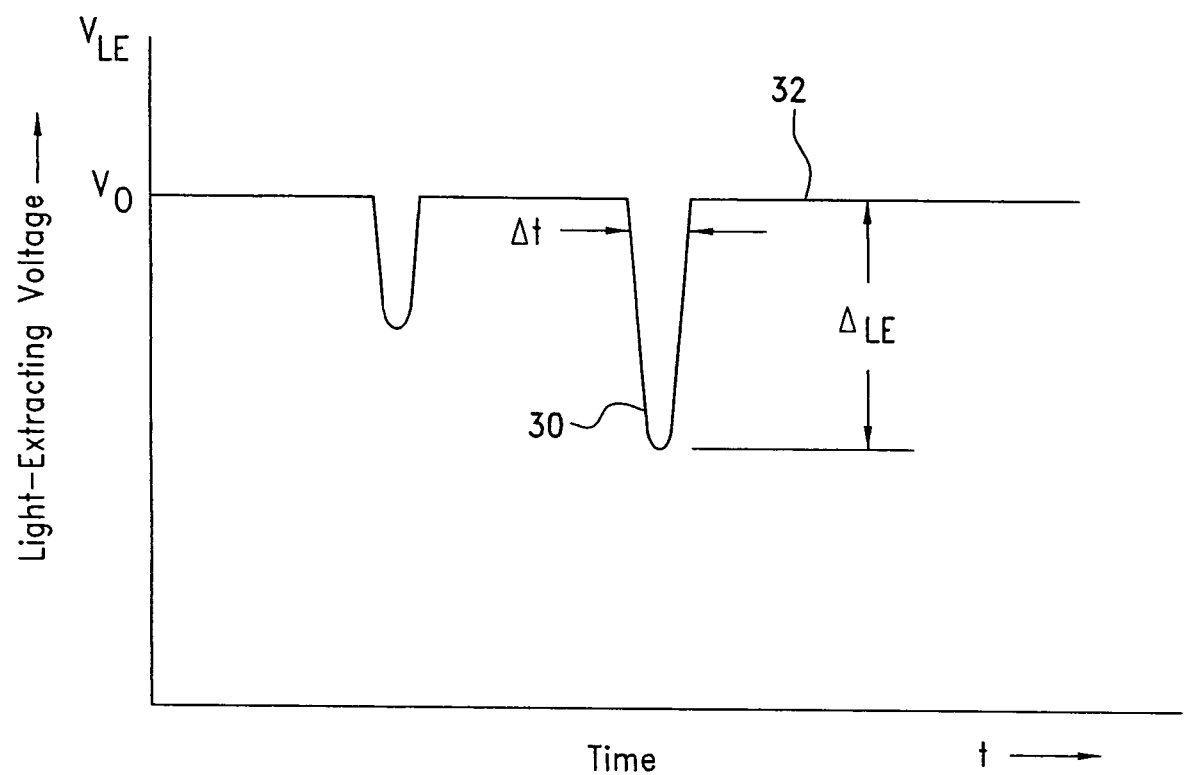
FIG. 2 is a simplified representation of the time-dependent output signal voltage generated by the conventional LE sensor of FIG. 1.

As alluded to above, there is a crucial difference between the signal, $V_{LS}$, created by this optical scheme and the signal, $V_{LE}$, shown in FIG. 2, produced by the LE-type sensor. Unlike the latter, the LS-type sensor, by design, prevents the incident light beam emerging from the back window of the flow cell from reaching the detector, $D_{LS}$. Instead, the incident beam is either "trapped" by means of a suitable small opaque beam "stop" (e.g., the inner opaque area 54) or deflected by a small mirror away from the lens that is used to collect the scattered light rays originating from the OSZ. Consequently, the relatively large "baseline" level, $V_0$, necessarily present in the overall signal, $V_{LE}$, produced by the LE-type sensor is now absent from the LS signal, $V_{LS}$. Ideally, the new "baseline" signal level is zero—i.e. there should be no scattered light generated from sources within the OSZ in the absence of a particle. In practice, of course, there will be some amount of background light caused by light scattered from the surfaces of the front and/or back windows of the flow channel, due to imperfections on, or contaminants attached to, the latter surfaces. In addition, there may be fluctuating background light due to scattering from small contaminant particles suspended in the diluent fluid. Also, for some samples there may be fluctuations in background light produced by a "sea" of ultrafine particles which comprise a major fraction of the overall particle population, but which are too small to be detected individually.

Figure 12:
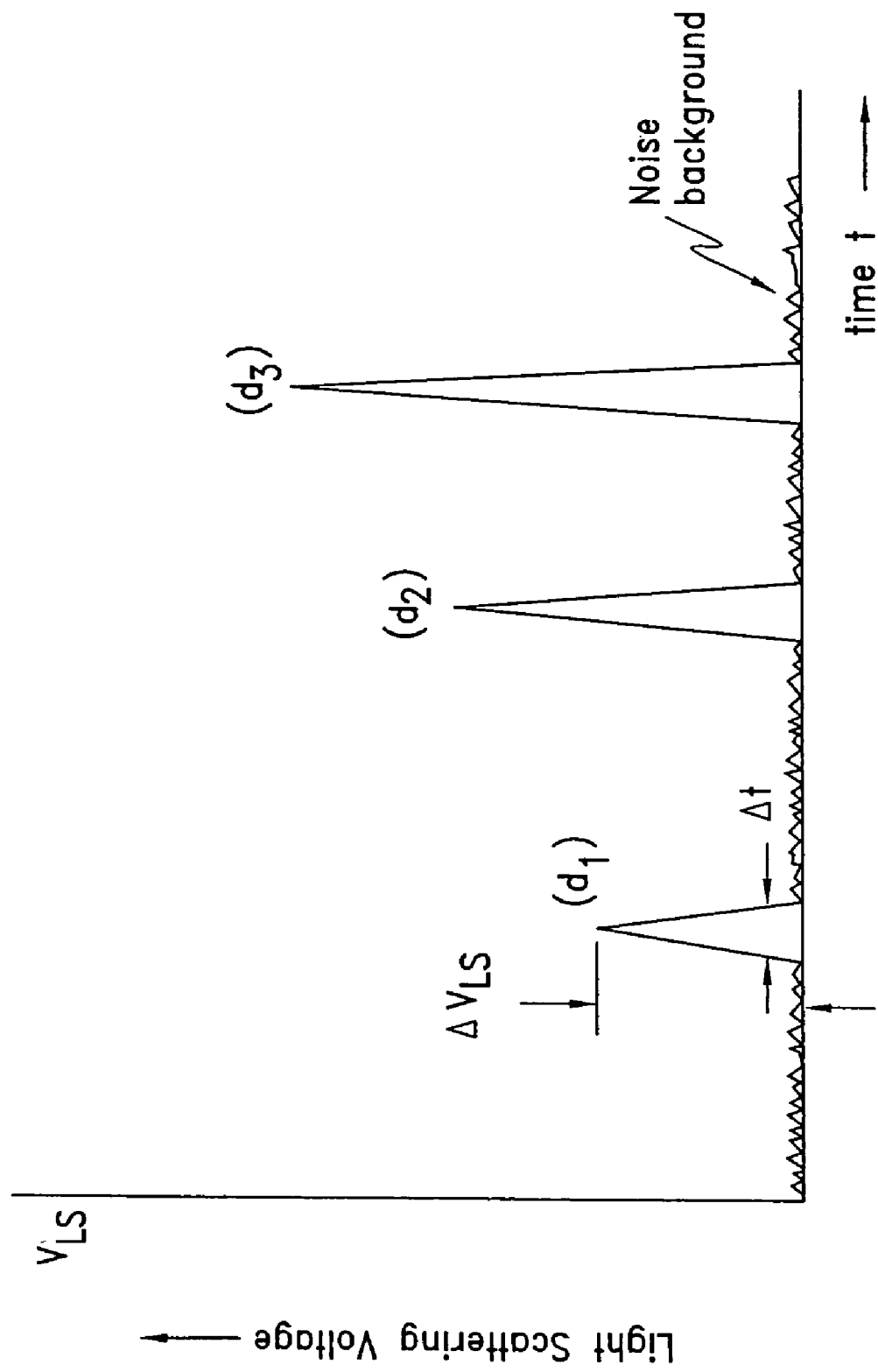
FIG. 12 is a simplified representation of the time-dependent output signal voltage generated by the new LS-type sensor.

When a particle of sufficient size passes through the OSZ, defined by the incident gaussian light beam and front and back windows of flow channel 35, a momentary pulse occurs in the output signal produced by the detector, $D_{LS}$, and associated signal-conditioning circuit. In general, one might naively expect that the larger the particle, the greater the amount of light scattered by it, assuming the same trajectory, and therefore the greater the height of the signal pulse. If this is the case, the output signal, $V_{LS}$, will resemble that shown schematically in FIG. 12 for particles of increasing diameter, $d_1 < d_2 < d_3$, having the same value of |x|. In practice, the actual pulse height depends not only on the size of the particle, but also its composition—specifically, its index of refraction (and that of the surrounding fluid) and absorbance, if any, at the incident wavelength. The pulse height also depends on the wavelength of the beam and the orientation of the particle as it passes through the OSZ, if it is not spherical and homogeneous. Finally, for particles comparable in size to, or larger than, the wavelength, the scattering intensity varies significantly with the scattering angle. Consequently, in this case the pulse height depends on the range of angles over which the scattered light is collected and measured.

The relationship between the scattered light "radiation pattern" (i.e. intensity vs angle) and all of these variables is described by classical Mie scattering theory, which takes into account the mutual interference of the scattered light waves within the particle. In general, the larger the particle, the more complex (i.e. non-isotropic) the angular dependence of the scattered intensity resulting from intra-particle interference. In order to optimize the response and performance of the LS-type sensor, one must confine the collection of scattered light to a range of angles, $\theta$, for which the net integrated response, $\Delta V_{LE}$, increases monotonically with the diameter, d, of particles of a given composition (i.e. refractive index) over the largest possible, or expected, size range. This requirement can usually be satisfied by choosing a range of relatively small angles, $\theta_1 < \theta < \theta_2$, close to the forward direction. In this way, one avoids "reversals" in the integrated scattering intensity with increasing particle size due to variations of the intensity with changes in angle, especially significant at larger angles as a consequence of Mie intra-particle interference.

There are two properties of the signal, $V_{LS}$, produced by the new LS-type sensor that are qualitatively different from the properties of the signal, $V_{LE}$, produced by the corresponding LE-type sensor. First, the signal pulse caused by passage of a particle through the OSZ and the "overall" signal, $V_{LS}$, are essentially the same in the case of the LS-type sensor. The relatively high background signal level that accompanies the pulse of interest in the LE-type sensor is absent: (The same situation clearly holds for a conventional LS-type sensor. This consists of the scheme shown in FIG. 1 with a similar addition of one or more lenses and a detector means for collecting and measuring the scattered light originating from the OSZ over a range of angles, excluding the incident light beam.) Therefore, in the case of relatively small particles that give rise to pulses of low magnitude, the signal/noise ratio achieved in practice using the LS method should be significantly better than that realized using the LE method. This advantage becomes more important the smaller the particle and the weaker the resulting pulse, as the latter approaches the prevailing noise fluctuations. Another way of appreciating the inherent advantage of the LS method over its LE counterpart is to realize that the former is based on "detection at null." That is, quantitative detection of a pulse ideally is carried out in the presence of zero background signal. From a signal/noise perspective, this is in sharp contrast to the situation that obtains for the LE method, which requires high "common-mode rejection." The "common-mode" signal, $V_0$, is always present in the raw signal, $V_{LE}$, and must be subtracted, or otherwise suppressed, in order to extract the (often small) signal pulse of interest.

There is a second important and distinguishing property of the LS signal, $V_{LS}$. The signal/noise ratio associated with the measurement of $\Delta V_{LS}$ can in principle be improved by increasing the power of the incident light beam, so as to increase the light intensity incident on a particle at all points within the OSZ. Therefore, in principle one can reduce the lower size detection limit for the new LS sensor by increasing the power of the light source, as for a conventional LS sensor. Eventually, a lowest size limit will be reached, based on noise fluctuations associated with the suspending fluid and/or the light source and detection system. Of course, as discussed above, the lower particle size limit can also be improved for the new LS-type sensor by reducing the width, $2w$, of the incident beam, assuming no change in the power of the latter. This action will obviously increase the maximum intensity incident on the particles that pass through the beam axis (x=0), and therefore the height of the largest resulting pulse for a particle of given size, as well. However, this method of improving the sensitivity eventually reaches a point of diminishing return, due to limitations imposed by diffraction theory (establishing a minimum beam width) and excessive variation of the focused beam width over the depth, b, of the flow cell due to excessively-long depth of field.

By contrast, an increase in the power of the light source has relatively little effect on the lowest particle size that can be measured using the LE method. For example, a doubling of the power of the light source will result in a doubling of the baseline signal level (FIG. 2), to $2V_0$. The height of the pulse, $\Delta V_{LE}$, produced by a particle of the same size and trajectory will also be doubled, assuming no change in the beam width. However, the root-mean-square magnitude of the noise fluctuations associated with the relatively high baseline signal level will typically also be approximately doubled, because these fluctuations are usually associated with the light source and therefore scale with the output power. Hence, one expects little or no improvement in the signal/noise level for the LE-type sensor. Consequently, there should be little or no reduction in the lower size detection limit achievable by the LE method as a consequence of increasing the power of the light source. An improvement will be realized only if the signal/noise ratio associated with the light source improves with increased power.

When uniform size particles flow through the new LS-type sensor, depending on their trajectories they are individually exposed to different values of maximum incident intensity, given by Equation 7, with r=x, z=0. (For simplicity, it can be assumed that the particles are much smaller than the beam width, so that every point in a given particle is exposed to the same intensity at any given time.) Therefore, as with the new LE-type sensor, the height, $\Delta V_{LS}$, of the resulting pulse generated by a particle of given size depends on the distance, |x|, of closest approach (z=0) to the axis of the incident beam. The smaller the distance |x|, the larger the value of $\Delta V_{LS}$. Hence, like its new LE counterpart, the new LS-type sensor generates a distribution of widely varying pulse heights, $\Delta V_{LS}$, when a suspension of uniform particles passes through it at an appropriate flow rate. The shape of the resulting PHD bears a strong qualitative resemblance to the highly asymmetric shape of the PHDs obtained using the new LE method, exemplified in FIGS. 4, 6 and 7. That is, the number of pulse counts (y-axis) is relatively small at the smallest measurable pulse height just above the noise fluctuations) and rises with increasing pulse height, $\Delta V_{LS}$. The pulse count value culminates in a peak value at a maximum pulse height, referred to as $^M\Delta V_{LS}$, corresponding to particle trajectories for which |x|≈0. Above $\Delta A V_{LS}$ the number of pulse counts ideally falls to zero, assuming that the particle concentration is below the coincidence concentration (discussed earlier) for particles of that size, so that at most one particle effectively occupies the OSZ at any given time. Of course, a PHD obtained using the new LS method usually pertains to particles that are smaller—often significantly so—than those used to generate a typical PHD using the new LE method.

As noted above, the shape of the PHD—number of pulse counts vs $\Delta V_{LS}$—generated for uniform particles using the new LS method is qualitatively similar to the shape of the PHD obtained for uniform (typically larger) particles using the new LE method. Both kinds of PHDs share the distinguishing characteristic of a sharp "cut-off" following their respective peak number of pulse counts, coinciding with their maximum pulse height values, $^M\Delta V_{LS}$ and $^M\Delta V_{LE}$. However, it should be appreciated that there are quantitative differences in the shapes of the two kinds of d=1, notwithstanding their qualitative similarities, even for the same particle size—e.g. d=1 μm. The "front end" design of the new LS-type sensor—i.e. the focused light beam and relatively thin flow cell—is essentially the same as that utilized for the new LE-type sensor. Therefore, what distinguishes one type of sensor from the other concerns the means and manner of light detection and the type and magnitude of the response pulses generated by each method, even in the case of particles of the same size. For the new LS method, the response is due only to light scattering, and its magnitude, $\Delta V_{LS}$, is proportional to the intensity of the light incident on the particle, all other relevant variables being the same.

By contrast, for the new LE method the magnitude of the response, $\Delta V_{LE}$, is a more complex function of the intensity incident on the particle. First, the response is due to a combination of physical effects—refraction (and reflection) plus light scattering. However, the scattering phenomenon asserts itself in an "inverse" sense. That is, a small fraction of the incident light flux is removed from the beam before it reaches the detector. Second, over the typical size range for which the new LE method is applicable, there is a substantial variation in the incident intensity across the particle. Therefore, it should not be surprising that the fractional change of pulse height due to a given change in |x|, dependent on both particle size and trajectory, is generally different for the two methods. Similarly, the fractional change in pulse height with particle diameter, dependent on both particle size and trajectory, is also generally different for the two methods. Rigorous application of the physical principles (Mie theory) underlying refraction, reflection and scattering for particles of various sizes, combined with gaussian beam optics, would be required in order to obtain reliable theoretical estimates of the detailed shapes of the PHDs generated by the two methods.

From the discussion above, it should be evident that the behavior of the new LS-type PHDs with respect to changing particle size approximates that obtained for the new LE-type PHDs, exemplified by FIG. 7. Notwithstanding the differences in the detailed shapes of the new LS-type PHDs—number of pulses vs $\Delta V_{LS}$—compared to new LE-type PHDs, the two types of PHDs share a common characteristic. There is a progressive shift to higher pulse-height values of one PHD to the next, corresponding to larger particle diameter. In particular, and most importantly, the maximum pulse-height values, $^M\Delta V_{LS}$, increase progressively with increasing particle size. Of course, this behavior assumes that the new LS-type sensor has been properly designed, with an appropriate range of detected scattering angles, precisely in order to ensure a monotonic response of $^M\Delta V_{LS}$ with d. There are two competing effects. On the one hand, the larger the range of angles over which scattered light is collected, the larger the resulting pulse height, $\Delta V_{LS}$, and hence the greater the signal/noise ratio for particles of a given size, resulting in higher sensitivity—i.e. a lower particle size detection limit. On the other hand, the smaller both the range of scattering angles collected and the actual angles themselves, the smaller (and more benign) the effects of intra-particle Mie interference. Consequently, it is less likely that "reversals" will occur in the detected scattering intensity—i.e. non-monotonic behavior of $^M\Delta V_{LS}$ vs d over the desired size range.

As previously discussed for new LE-type PHDs, a new LS-type PHD for a given particle diameter, $d=d_2$, can be constructed with reasonable accuracy from a PHD measured for a smaller size, $d=d_1$, by "stretching" the latter to higher values of $\Delta V_{LS}$, using an appropriate scale factor. (Usually it is desirable to use a logarithmic pulse-height scale—number of pulses vs log $\Delta V_{LS}$.) This scale factor is given by the ratio of the final and initial maximum cut-off pulse height values, $^M\Delta V_{LS}(d_2)/^M\Delta V_{LS}(d_1)$. In practice, as with the new LE method, one can measure a set of new LS-type PHDs using a set of suspensions of uniform particles that encompass the desired size range with appropriate diameter spacing. The PHD corresponding to any size between two measured sizes can then be calculated by interpolating between the two adjacent measured PHDs using this linear stretching operation with an appropriate scale factor.

Finally, in addition to the similarity/difference in the shapes of the PHDs generated by the two new methods, there is another property of the response of the new LS-type sensor that is qualitatively similar to, but quantitatively different from, the corresponding property of the new LE-type sensor. This is the width of the effective OSZ, $2w_d$, and the corresponding sensor efficiency, $\phi_d$, related to $2w_d$ and the flow channel width, a, by Equation 8. As for the new LE-type sensor, parameter $\phi_d$ accounts for the fact that only a small fraction of the total number of particles passing through the sensor during data collection are detected and therefore contribute to the PHD. The same concept involving an imaginary, approximately cylindrical OSZ described above in connection with the new LE-type sensor is equally valid for the new LS-type sensor. For particles of a given diameter, the integrated scattered light intensity collected over a fixed, selected range of scattering angles decreases with decreasing light intensity incident on the particle. Therefore, the larger the distance, |x|, of closest approach (i.e. z=0) of the particle trajectory to the axis of the incident beam, the smaller the magnitude of the response, $\Delta V_{LS}$. At some largest value of |x|, the pulse height will fall sufficiently that the pulse will effectively be indistinguishable from the prevailing noise fluctuations in the overall signal, $V_{LS}$, thereby rendering the particle undetectable. This value of |x| thus defines the radius, $w_d$, of the effective (approximately cylindrical) OSZ for particles of the given diameter, d. The sensor efficiency for this size is then easily determined using Equation 8.

It should therefore be evident that the larger the particle diameter, d, the greater the distance of closest approach, |x|, of the particle to the incident beam axis while still permitting its detection. Consequently, the larger the particle, the larger the width, $2w_d$, of the effective OSZ and, hence, the greater the sensor efficiency, $\phi_d$, for particles of this larger size. This monotonic relationship between $\phi_d$ (or $2w_d$) and d presumes correct design of the new LS-type sensor, such that $\Delta V_{LS}$ increases monotonically with d for particles of a given composition over the size range of interest. Therefore, $\phi_d$ for the new LS-type sensor will increase with d, as is the case of the new LE-type sensor. However, one should not expect that the increase in $\phi_d$ with d will obey the same relationship that was found for the new LE method, summarized in FIG. 9. Qualitatively, one may expect that the behavior of $\phi_d$ vs d will be similar for both the new LS and LE methods. Quantitatively, however, the details of this behavior should be expected to differ for the two methods, due to fundamental differences between the physical properties underlying scattering and refraction/reflection (minus a small scattering contribution).

There is an additional, important difference in the behavior of the new LS response compared to its new LE counterpart, with respect to sensor efficiency. As already discussed, the sensitivity of the new LS-type sensor can be improved—i.e. the lower particle size limit reduced —by increasing the power of the incident light beam, assuming that all other design parameters are unchanged. Related to this improvement is an enhancement in the sensor efficiency, $\phi_d$. This is evident, given the fact that the pulse height, $\Delta VLS$, obtained for a given particle size and trajectory distance, |x|, will increase in proportion to the increase in the light intensity incident on the particle. Hence, the trajectory can be further from the beam axis than it could otherwise be while still permitting detection of the particle. Therefore, the width, $2w_d$, of the effective OSZ and the corresponding efficiency, $\phi_d$, for particles of the same diameter, d, will increase (in some nonlinear functional fashion) with increasing power of the incident beam. The resulting curve describing $\phi_d$ vs d (the counterpart of the plot obtained for the new LE-type sensor, shown in FIG. 9) will shift in some fashion to a set of higher $\phi_d$ values for each value of d.

In summary, with respect to the power of the incident beam, the behavior of the new LS-type sensor differs both qualitatively and quantitatively from the behavior of the new LE-type sensor, in at least two important respects. First, the lower size detection threshold for the new LS-type sensor in general increases with increasing incident beam power. This behavior typically does not hold for the new LE-type sensor, unless the signal/noise ratio associated with the light source also increases with the power of the beam (or, using a different, "quieter" light source and/or detector and associated signal-conditioning circuit). Second, the sensor efficiency, $\phi_d$, associated with the new LS-type sensor in general also increases with increasing incident beam power. This behavior typically is not obtained for the new LE-type sensor, unless there is an improvement in the signal/noise ratio associated with the increased power of the light source.

Finally, the PHD generated by the new LS-type sensor for particles of a given size and composition will shift proportionately to higher pulse-height values if the power of the incident beam is increased. This aspect of the response generated by the new LS-type sensor therefore implies that the set of PHDs generated by a set of samples containing uniform particles of different size has quantitative significance only with reference to a particular incident beam power. If the power is increased, the PHDs will shift correspondingly to higher pulse-height values. Interestingly, this behavior is similar to that expected and observed for the new LE-type sensor, albeit for a different reason. If the power of the incident beam is increased by a given percentage, both the "baseline" voltage, $V_0$, and the pulse height, $\Delta V_{LE}$, will increase by the same percentage. Consequently, the PHDs shown in FIG. 7 for a particular set of particle diameters will shift upward in pulse height value by the same percentage.

We will now consider the crucial task of converting the "raw" data—the PHD—obtained from a sample of suspended particles into the object ultimately desired—the particle size distribution, or PSD. It is useful to compare this task conceptually with the operation required in the case of a conventional LE- or LS-type sensor. There, the height of the pulse due to passage of a particle through the OSZ is nearly independent of its trajectory, because the intensity of the incident beam is designed to be approximately constant across the flow channel (i.e. along the x-axis) for a given z-axis value (e.g. z=0). Consequently, particles of a given size ideally give rise to pulses of substantially the same height, and the resulting PHD is therefore, in effect, equivalent to the final desired PSD. There is a one-to-one correspondence between a given, measured pulse height, $\Delta V_{LE}$ (or $\Delta V_{LS}$), and the particle diameter, d. If particles of a larger or smaller size pass through the sensor, the resulting pulse heights are larger or smaller, respectively. A "calibration curve," consisting of pulse height vs particle diameter, is all that is needed to obtain, by simple interpolation, the PSD from the PHD. Obtaining the raw PHD data using the conventional SPOS method is equivalent to determining the final, desired PSD.

By contrast, as discussed earlier, the response of the new LE- (or LS-) type sensor is much more "convoluted." Even in the simplest case of particles of a single size, the resulting PHD consists of a broad spectrum of pulse heights, from the smallest values just above the prevailing noise fluctuations, to the maximum value, $^M\Delta V_{LE}$ (or $^M\Delta V_{LS}$), associated with that size. Therefore, in the typical case of particles of widely varying size, the resulting PHD consists of an even wider assortment of pulse heights. No longer is there a simple correspondence between pulse height and particle size. It is therefore no longer a simple, straightforward procedure to transform the set of particle counts vs pulse-height values contained in the PHD into the desired size distribution—particle counts vs particle diameter.

Conversion of the PHD to the desired PSD requires three distinct procedures. First, the raw PHD must be inverted, or deconvoluted, using a specialized mathematical algorithm. Its purpose is to convert the "wide-spectrum" PHD produced by the new LE- (or LS-) type sensor into a "sharp", idealized PHD, equivalent, in effect, to what would have been obtained using a conventional LE- (or LS-) type sensor. Such an idealized, deconvoluted PHD—hereinafter referred to as the dPHD—has the property that all pulses of a given height, $\Delta V_{LE}$ (or $\Delta V_{LS}$), belong exclusively to particles of a given size (assuming, always, particles of a given composition). The dPHD is equivalent to what would have been obtained if all of the particles contributing to the original PHD had passed through the center (axis) of the incident beam.

A second straightforward procedure is then carried out. A preliminary, or "raw", PSD is obtained from the dPHD by simple interpolation of the calibration curve that applies to the specific new LE- (or LS-) type sensor utilized—e.g. the curve shown in FIG. 8A. This procedure permits a one-to-one translation of each deconvoluted pulse height value in the dPHD into a unique particle diameter associated with this value, thus yielding the raw PSD. A third procedure is then needed to convert the raw PSD thus obtained into a final PSD that is quantitatively accurate. The number of particle counts in each diameter channel of the raw PSD is the number of this size that actually contributed to the measured PHD. As discussed above, this is typically only a small fraction of the total number of particles of the same size (i.e. within the size range defined by the diameter channel) residing in the volume of sample suspension that passed through the sensor during data collection. This fraction, $\phi_d$, of particles actually detected by the new LE- (or LS-) type sensor varies significantly with the particle diameter, d, as shown in FIG. 9. Therefore, in the third and final procedure, the number of particles contained in each diameter channel of the raw PSD must be multiplied by the value of $1/\phi_1$ that applies for that channel. This operation yields the final, desired PSD, describing the number of particles of each size estimated to reside in the quantity of sample suspension that passed through the sensor during data acquisition. Values of $1/\phi_d$ for each value of diameter, d, can be obtained from the sensor efficiency curve, $\phi_d$ vs d, by interpolation.

There are two independent algorithms presented herein for deconvoluting a measured PHD, to obtain the dPHD, hereinafter referred to as "matrix inversion" and "successive subtraction." Implementation of either procedure is based on the property that the response of the new LE- (or LS-) type sensor—like its conventional SPOS counterpart—is additive. Because the particles passing through the sensor give rise to signal pulses one at a time, the resulting PHD can be considered to be composed of a linear combination, or weighted sum, of individual PHDs corresponding to uniform particles of various sizes, referred to as "basis vectors." (This term is well known in linear algebra.) Each of these basis vectors represents the response of the system to a statistically significant number of particles of a single, given size. Examples include the PHD shown in FIG. 4, obtained for d=1.588-µm, and the eight PHDs shown in FIG. 7.

The measured PHD can be referred to as PHD($\Delta V$), where $\Delta V$ denotes the pulse height, $\Delta V_{LE}$ or $\Delta V_{LS}$, depending on the type of new sensor employed. It is considered to be constructed from a linear combination of N basis vectors, referred to as $PHD_I(\Delta V)$, where I=1, 2 . . . , N. $PHD_1(\Delta V)$ is the vector for $d=d_1$; $PHD_2(\Delta V)$ is the vector for $d=d_2$; . . . and $PHD_N(\Delta V)$ is the vector for $d=d_N$. Therefore, $PHD(\Delta V)$ can be written as $$PHD(\Delta V) = c_1 PHD_1(\Delta V) + c_2 PHD_2(\Delta V) + \ldots + c_N PHD_N(\Delta V) \quad (9)$$

The weighting coefficients, $c_1, c_2, c_N$, constitute the desired solution to Equation 9. These coefficients represent the values in each of the dPHD channels.

The eight measured PHDs shown in FIG. 7 constitute basis vectors that can be used for the deconvolution of any measured PHD. However, clearly there are too few of these vectors to permit computation of a dPHD of acceptable pulse height resolution, and therefore a PSD of correspondingly acceptable size resolution. Typically, one must use a much larger number of basis vectors, much more closely spaced (in pulse height), in order to achieve reasonable resolution in the final PSD. The prospect of obtaining a relatively large number of basis vectors (e.g. 32, 64 or 128) by measuring a similarly large number of samples of uniform particles, appropriately spaced, is impractical (if not impossible, given the lack of a sufficient variety of commercially available particle size standards).

However, according to the invention, the required large number of basis vectors can be obtained by one or more straightforward procedures, starting with a relatively small number of vectors generated experimentally (like the eight shown in FIG. 7). As discussed earlier, a PHD having a desired maximum pulse height value, $^M\Delta V_{LE}$ (or $^M\Delta V_{LS}$), can be obtained from an existing (e.g. experimentally determined) PHD, having a smaller maximum pulse height value, by "stretching" the latter along the pulse height axis. The pulse-height value for each channel of the existing PHD is multiplied by a factor equal to the ratio of the "target" value of $^M\Delta V_{LE}$ (or $^M\Delta V_{LS}$) to the lower value. Conversely, a PHD having a higher maximum pulse height value than the "target" value can be "compressed" downward as desired, using for the multiplicative factor the ratio (smaller than unity) of the lower to the higher maximum pulse-height values. In principle, therefore, an arbitrarily large number of basis vectors can be obtained from a small starting set of (measured) basis vectors, using these stretching or compressing operations. Instead of determining the small number of basis vectors experimentally, they may also be computed from a simple theoretical model. The remaining column basis vectors can then be computed by interpolation and/or extrapolation from these "computed" basis vectors. It is also possible to compute all of the required basis vectors from the theoretical model.

Figure 13A:
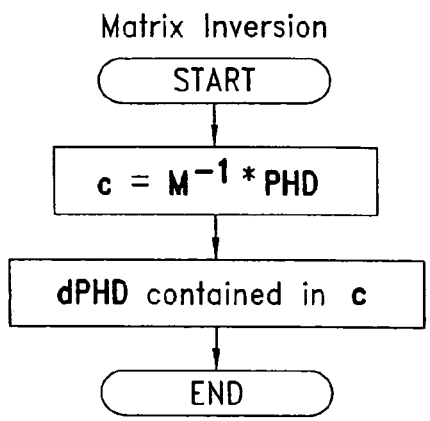
FIG. 13A and FIG. 13B contain flow diagrams for two mathematical algorithms (matrix inversion and successive subtraction, respectively) that can be used to deconvolute the measured PHD data.

Two algorithms have been utilized to solve Equation 9. The conventional, well-known method, called matrix inversion, is summarized schematically by the flow diagram shown in FIG. 13A. There are two starting quantities, PHD and M. Quantity PHD, written in bold type, is a 1×N column vector, containing the "source" data. The first (i.e. top) column value is the number of particles in the first channel of the measured PHD. The second column value is the number of particles in the second channel of the measured PHD, and so forth. Finally, the Nth (i.e. bottom) column value is the number of particles in the Nth (last) channel of the measured PHD. Parameter N, equal to the number of pulse-height channels (and corresponding particle-diameter channels of the raw PSD), is chosen according to the desired resolution of the PSD. Typical values are 32, 64 and 128. Quantity M is a square (N×N) matrix containing the N basis vectors, each of which is a separate 1×N column vector. Hence, the first column of M contains $PHD_1(\Delta V)$; the second column contains $PHD_2(\Delta V)$; . . . and the Nth column contains $PHD_N(\Delta V)$ The solution of Equation 9 is well known from linear algebra, $$c = M^{-1} * PHD \quad (10)$$

where $M^{-1}$ is a matrix which is the inverse of matrix M. Multiplication of $M^{-1}$ by the source vector, PHD, yields the desired result, the 1×N column vector, c, constituting the desired dPHD vector. The individual contents (values) for each of the N channels must be multiplied by an appropriate factor, so that the sum of the contents, $c_1+c_2+ \ldots +c_N$, is the same as the total number of particles that contributed to the measured PHD in the first place, thus ensuring conservation of the total number of particles.

A second method, called successive subtraction, has been developed for solving Equation 9. This represents a novel and powerful technique for deconvoluting the measured PHD. In the case of the new LE- (or LS-) type sensor, the successive subtraction method provides a particularly effective and useful procedure for deconvoluting the PHD. As discussed above, what is so unusual about the response of the LE- (or LS-) type sensor is the shape of the PHD obtained for uniform-size particles. Specifically, it is highly asymmetric, possessing a sharp cut-off and, hence, a well-defined maximum pulse height value, $^M\Delta V_{LE}$ (or $M\Delta V_{LS}$). From the point of view of the deconvolution process, this is an important and useful property. The channel of the PHD that has the largest pulse height value (assuming that it contains a statistically significant number of particle counts) identifies the largest particle size that can be present in the PSD (apart from over-size outliers). This is the diameter, $d_I$, of the basis vector having a maximum pulse height value that coincides with the maximum pulse height found in the measured PHD.

The successive subtraction algorithm is conceptually simple. The contribution of the maximum-size basis vector, $PHD_I(\Delta V)$, with an appropriate weighting, or scaling, factor (reflecting the number of particles of that size that contributed to the original PSD) is subtracted from the starting PHD. This leaves an "intermediate" PHD vector that has a smaller total number of particle counts and a smaller remaining maximum pulse height value. This operation is then repeated successively using the remaining basis vectors corresponding to smaller-size particles, until the entire starting PHD effectively "disappears," or is substantially "consumed," leaving virtually no remaining particle counts or channels to be accounted for.

Figure 13B:
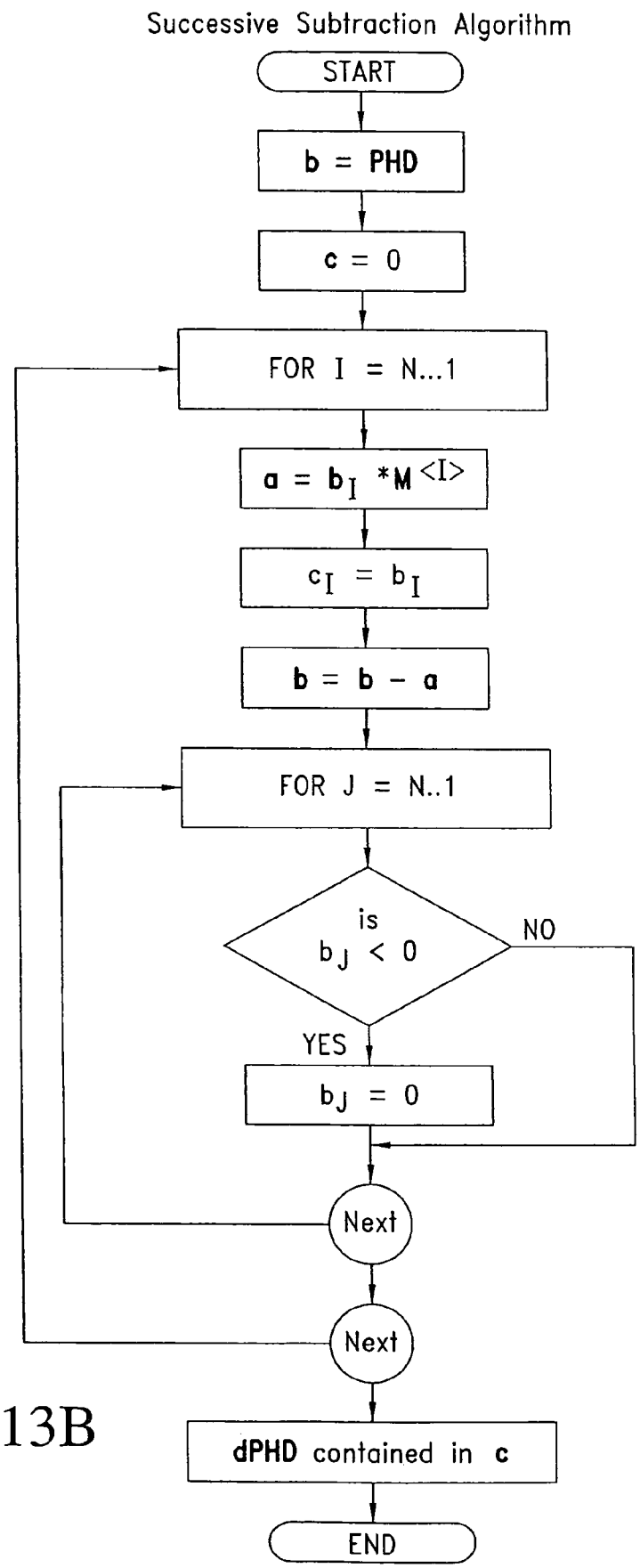

The successive subtraction algorithm is described schematically by the flow diagram shown in FIG. 13B. The starting measured PHD column vector is duplicated as an intermediate column vector, b. In addition, column vector c, that ultimately will become the solution (dPHD), is initialized to zero (i.e. a 1×N column vector of all zeros). As before, the N ×N square matrix M contains the N basis vectors that have been selected to perform the deconvolution. Two calculation "loops" are then utilized: I=N, N−1, . . . 1 and, within the I-loop, J=N, N−1, . . . , 1. In the larger I-loop, starting with I=N, the Ith column of matrix M is multiplied by the Ith element of vector b. This becomes a new 1×N column vector, called a. The Ith element in vector c is then set equal to the Ith element of vector b, and vector a is subtracted from vector b.

Next, the calculation enters the secondary J-loop. Starting with J=N, a decision is made based on the value of the Jth element in vector b. If it is less than zero, the Jth element is set equal to zero. In either case, the J-loop cycles back to the beginning, and this query is repeated for J=N−1, continuing in the same fashion all the way to J=1. After the J-loop is completed, the computation returns to the beginning of the I-loop. The operations within the I-loop are then repeated for I=N−1. These include calculation of vector a, equating of the Ith element of vector c with the Ith element of vector b, and subtraction of vector a from vector b. After all cycles of the I-loop have been completed, one obtains vector c—the desired dPHD.

Figure 14:
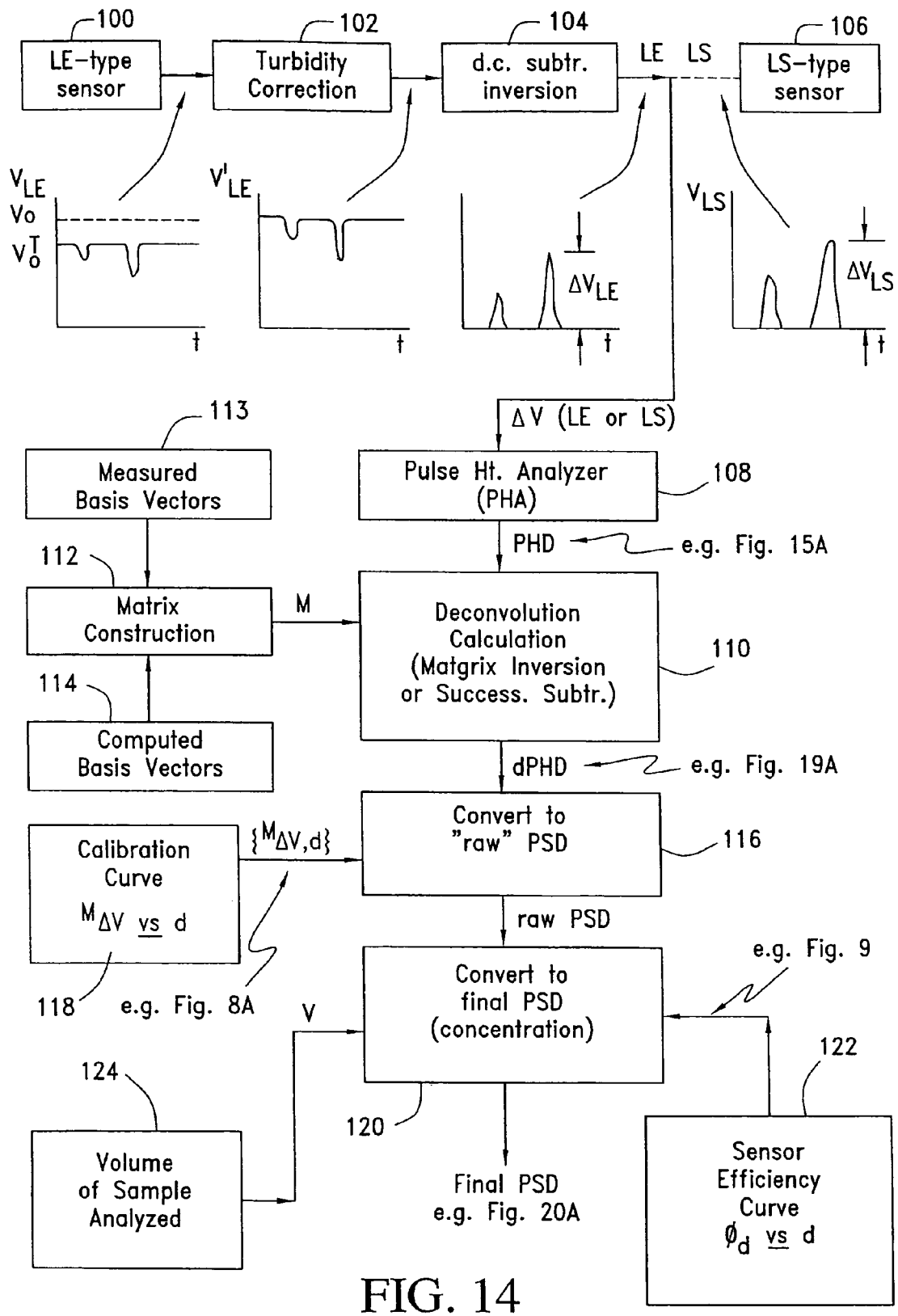
FIG. 14 is a flow chart summarizing the operation and structure of the new LE- and LS-type sensors, including the measurement and computational steps needed to obtain the PSD.
Figure 15A:
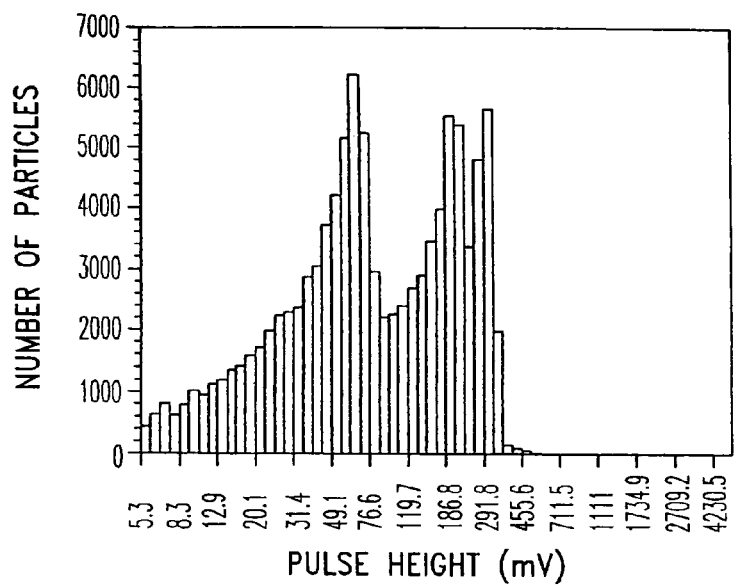
FIG. 15A shows the measured PHD (64-channel resolution) obtained from sample "A" (latex trimodal, 0.993-, 1.361- and 1.588-μm) using the new LE-type sensor.

FIG. 14 contains a schematic diagram that summarizes the operational structure of the LE- (or LS-) type sensors and methods of the invention, including all measurement and computational steps needed to obtain the final desired PSD. A sensor 100 of the LE-type incorporating the principles of the present invention as described with respect to the sensor of FIG. 3 responds to a relatively concentrated particle suspension to produce output $V_{LE}$. It will be observed that output $V_{LE}$ has a voltage baseline level $V_0^T$ that is lower than baseline voltage $V_0$ in the absence of turbidity. This reduction in the voltage is caused by turbidity introduced by a relatively concentrated suspension being fed through sensor 100. Turbidity correction is introduced at 102, resulting in an overall signal $V^1_{LE}$, raising the baseline voltage level to $V_0$. The d.c. component of the signal is effectively removed from $\Delta V_{LE}^1$ by subtraction (or a.c. coupling) in 104, and the signal is also inverted at 104 to produce pulse height signal $\Delta V_{LE}$. Alternatively, a sensor 106 of the LS-type that also incorporates the principles of the present invention may provide a pulse height signal $\Delta V_{LS}$. A pulse height analyzer 108 organizes the pulse height signal $\Delta V$ ($\Delta V_{LE}$ or $\Delta V_{LS}$) into a pulse height distribution PHD, as shown in FIG. 15A. A deconvolution calculation using matrix inversion or successive subtraction is performed at 110 to produce a deconvoluted PHD, dPHD. The deconvolution calculation requires a matrix M that is constructed at 112 with column basis vectors that correspond to particular particle diameters. These, as explained below, will either be measured at 113 by sending particles of known size through the sensor (either LE or LS) or computed at 114.

Figure 19A:
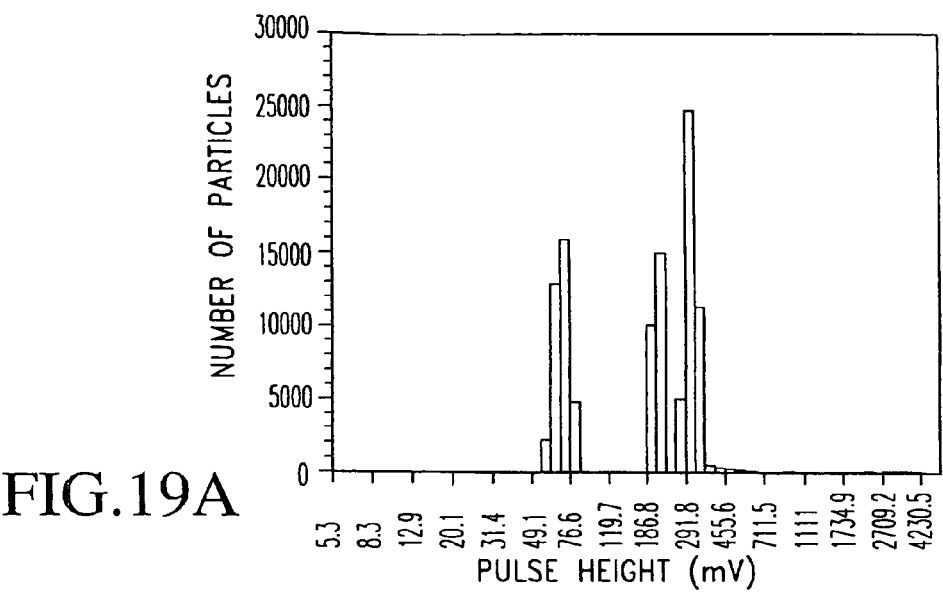
FIG. 19A shows the computed dPHD (64-channels) obtained from the measured PHD for sample "A" (latex trimodal, FIG. 15A), using the successive subtraction algorithm.
Figure 19B:
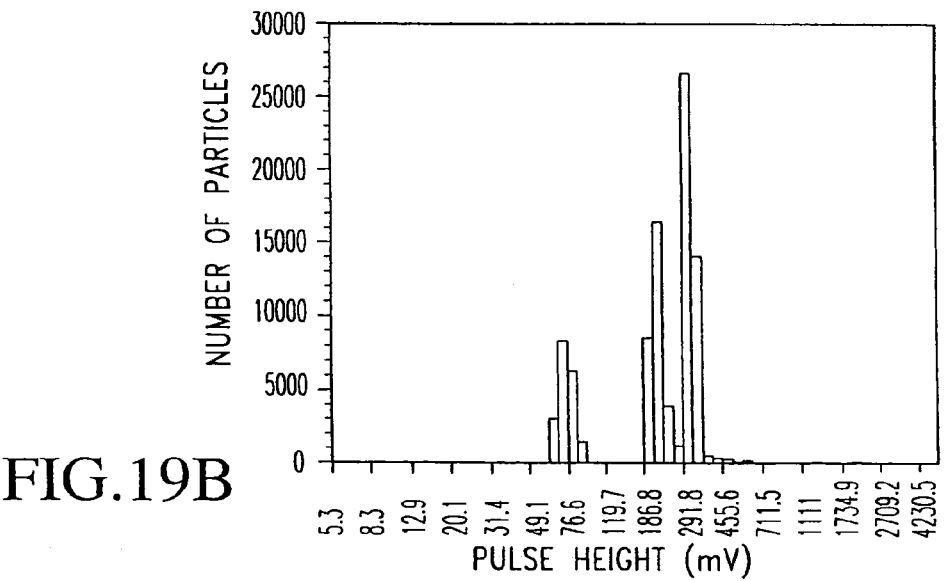
FIG. 19B shows the computed dPHD obtained from the measured PHD for sample "B" (latex trimodal, FIG. 15B), using the successive subtraction algorithm.
Figure 19C:
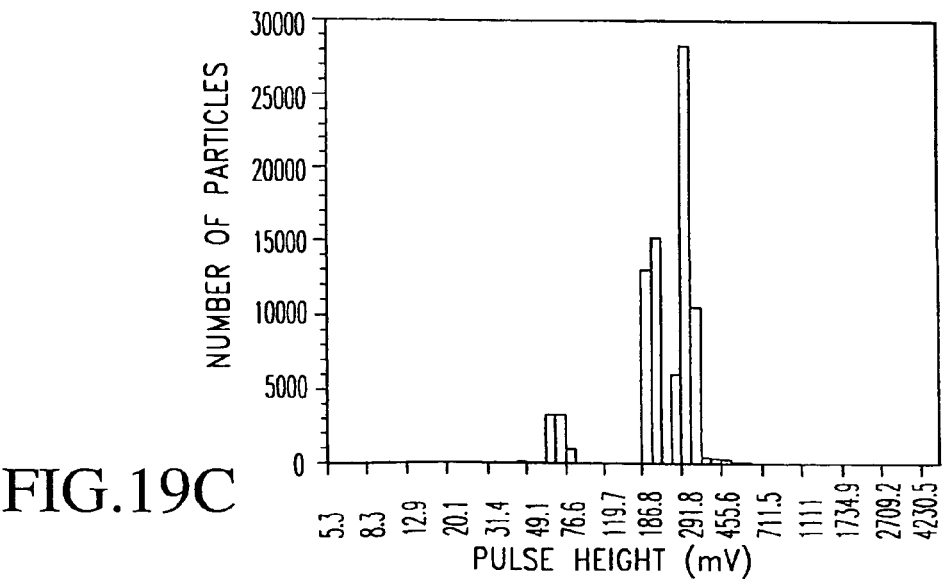
FIG. 19C shows the computed dPHD obtained from the measured PHD for sample "C" (latex trimodal, FIG. 15C), using the successive subtraction algorithm.

The dPHD, as shown in FIG. 19A, is converted to "raw" PSD (particle size distribution) at 116 through the use of calibration curve 118 which plots the relationship between pulse height $^M\Delta V$ against particle diameter as shown in FIG. 8A. The raw PSD is then converted at 120 to the final PSD result. The raw PSD is normalized by multiplying by 1/Φd from sensor efficiency curve 122, as shown in FIG. 9, and adjusted by a volume factor from an analysis of sample volume at 124.

In order to obtain PSD results having the highest possible reproducibility and resolution, it is necessary to optimize the quality—specifically, signal/noise ratio and reproducibility—of the measured PHDs from which the PSDs are obtained by deconvolution. Therefore, as has already been pointed out, a statistically significant number of particles of each relevant size (i.e., each small range of relevant sizes) must pass through the OSZ of the new sensor and be detected. However, there is another, equally critical factor that influences the quality of the PHD (and subsequent PSD) results. This involves the spatial distribution of particle trajectories with respect to the illuminating beam, as discussed below.

It is useful to review the PHD obtained for uniform (1.588-μm) polystyrene latex spheres, shown in FIG. 4. Clearly, this PHD possesses a high dynamic range—i.e., a high ratio of the particle counts obtained for (approximately) the highest pulse-height channel (≈5600) to the number measured for the lowest channel (≈100). This high ratio is a consequence of the fact that the flow of fluid and particles through the flow channel of the new sensor has been designed so as to yield a substantially uniform distribution of particle trajectories across the width (x-axis) of the channel. All distances, |x|, of closest approach of the trajectories to the axis of the light beam are sampled with approximately equal probability. In particular, therefore, particles will pass through the central portion of the beam (i.e., with trajectories close to A in FIG. 5), giving rise to the largest number of counts at substantially the maximum pulse-height value. Particles will also pass with equal probability through all lesser intensity regions, yielding successively fewer counts at successively smaller pulse-height values.

If the flow of particles is distorted in such a way as to cause non-uniform sampling of |x| values, then the shape of the resulting PHD obtained for uniform particles will be different fro that shown in FIG. 4. Specifically, in an inferior apparatus (e.g., having poor fluidics design), the trajectories might be clustered in such a way as to cause the particles to avoid the central, high intensity region of the beam. In this case, the high-count peak portion of the PHD will effectively be truncated, resulting in a much lower ratio of maximum to minimum counts.

If there is significant spatial non-uniformity in the distribution of particle trajectories, then this non-ideal distribution must be maintained for all PHD measurements. The basis vectors, whether measured or computed, must relate to the same non-uniform distribution of trajectories as that which occurs during measurement of an unknown sample. Otherwise, there will be significant distortion of the dPHD and corresponding PSD. In practice, it may be difficult, if not impossible, to maintain a particular, non-uniform spatial distribution of particle trajectories over an extended period of time, given the number of variables that come into play. Hence, in practice it is necessary to design the flow channel and associated fluidics system, as well as the illumination/detection optics, in such a way as to produce a spatial distribution of trajectories that is substantially uniform.

It is instructive to test the effectiveness of the deconvolution procedure for converting the measured PHD to the raw PSD, using a sample that has a simple, known size distribution. FIGS. 15A, B, C show the PHDs obtained using the new LE-type sensor for a series of three mixtures of uniform polystyrene latex "standard" particles (Duke Scientific, Palo Alto, Calif.), each containing three sizes: 0.993-μm, 1.361-μm and 1.588-μm. Each of the PHDs was obtained by passing 16-ml of the particle suspension through the sensor at a flow rate F=20 ml/min, resulting in a data collection time of 48 sec. These PHDs were constructed using 64 channels, evenly spaced on a logarithmic scale of $\Delta V_{LE}$, from 5 mV to 5000 mV. The choices of 64 channels and 16-ml sample volume resulted in acceptably low statistical fluctuations in the number of collected particle counts in each channel, yielding stable, reproducible DPHD results following deconvolution and very good size resolution in the resulting PSD, as seen below.

Figure 15B:
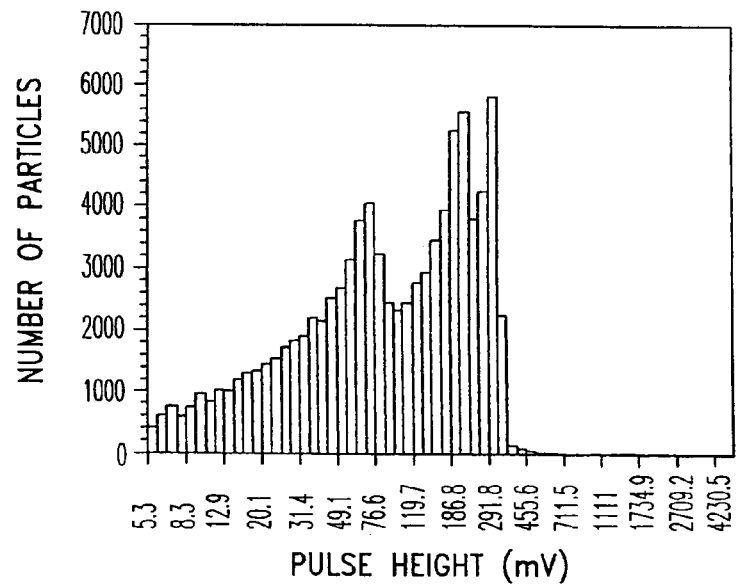
FIG. 15B shows the measured PHD obtained from sample "B" (same as Sample "A," but only 50% of the 0.993-μm latex) using the new LE-type sensor.
Figure 15C:
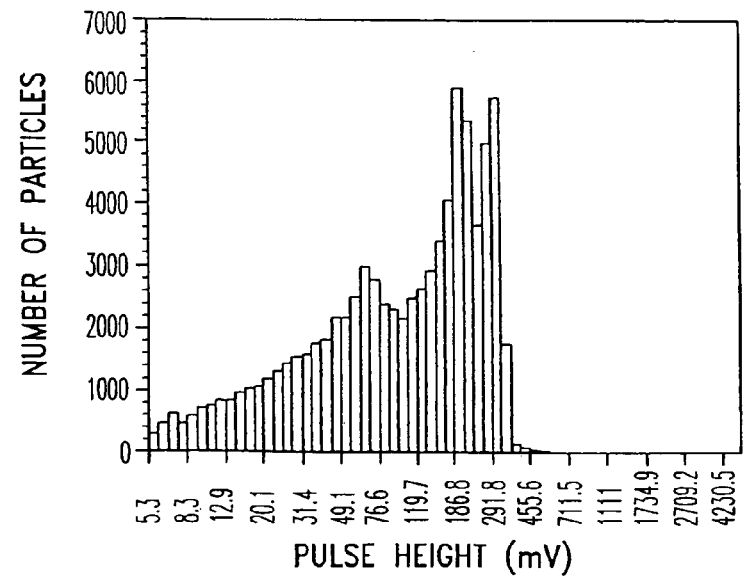
FIG. 15C shows the measured PHD obtained from sample "C" same as Sample "A," but only 25% of the 0.993-μm latex) using the new LE-type sensor.

The sample used in FIG. 15A consisted of 0.5-ml of prediluted 0.993-μm latex stock, plus 1-ml of prediluted 1.361-μm latex stock, plus 2-ml of prediluted 1.588-μm latex stock. In all cases the original latex stock suspensions consisted of 1% (w/w) solids (density p=1.05), and the predilution factor was 1000:1. The sample used in FIG. 15B was the same as that used for 15A, except only one-half the amount of 0.993-μm latex stock was used (0.25-ml, instead of 0.5-ml). The sample used in FIG. 15C was the same as that used for 15B, except the amount of 0.993-μm latex stock was again reduced by a factor of two (0.125-ml, instead of 0.25-ml). The total number of particle counts contained in the three PHDs was 102,911 (A), 90,709 (B) and 81,827 (C).

There are important qualitative features of the PHDs shown in FIGS. 15A, B, C that are immediately evident. First, as expected, there is a wide range of $\Delta V_{LE}$ values present in each PHD, with the characteristic "left-decaying" shape (i.e. falling from high to low $\Delta V_{LE}$ values) seen previously for uniform-size particles (e.g. in FIGS. 4, 6 and 7). Notwithstanding the wide range of pulse heights obtained, the trimodal nature of the underlying PSDs is clearly evident for each of the three samples. Second, there is the characteristic, abrupt "cut-off" in each PHD that defines its upper end—i.e. the maximum pulse height value, $^M\Delta V_{LE}$, for the entire distribution, as seen in the PHDs obtained for uniform-size particles. For all three samples the value of $M\Delta V_{LE}$ (i.e. at the midpoint of the highest channel) is 326 mV. (This ignores the existence of small numbers of particle counts at larger pulse heights, due to over-size particles and possibly coincidences, as discussed previously.)

The effectiveness of the deconvolution procedures described above can be verified by applying them to the measured PHDs shown in FIGS. 15A, B, C. It is instructive to compare the dPHD results obtained from the two proposed deconvolution algorithms using the same data. First, it is useful to show an example of the matrix that can be used to deconvolve the measured PHD vectors using either technique. For convenience in displaying the numerous entries contained in the matrix and vectors, it is useful to employ a reduced channel resolution of 32, rather than the value of 64 adopted for the PHDs shown in FIGS. 15A, B, C. An appropriate 32×32 matrix is therefore shown in FIGS. 16A and 16B, in which all entries have been rounded to three decimal places for ease of display.

Each of the rows of the matrix corresponds to successive pulse height channels with increasing row numbers indicating increasing pulse height signals. As discussed above, each column of the matrix represents a basis vector corresponding to a particular size. Nine of these vectors were obtained experimentally, by measuring the PHDs for a series of uniform polystyrene latex particles, as discussed earlier. Each measured basis vector was assigned to that column of the matrix for which the maximum count value lies on the diagonal—i.e. where the row and column numbers are the same. In the 32×32 representation shown in FIGS. 16A and 16B, the measured basis vectors (associated with the diameters indicated) occupy columns #6 (0.722-μm), #8 (0.806-μm), #12 (0.993-μm), #17 (1.361-μm), #19 (1.588-μm), #20 (2.013-μm), #26 (5.03-μm), #29 (10.15-μm) and #31 (20-μm). The entries for each column basis vector have been renormalized, so that the peak value equals unity in each case. The remaining 23 empty columns in the matrix are then filled up with "theoretical" basis vectors, where each entry is obtained by linear interpolation or extrapolation of the corresponding entries in nearby measured vectors, equivalent to the "stretching" operation discussed earlier.

The source data column vectors representing the measured, 32-channel PHDs for the three different samples are shown in FIG. 17. (The contents of adjacent pairs of channels in the PHDs shown in FIGS. 15A, B, C were added together to obtain the necessary 32-channel values.) The results obtained by deconvolution of the PHDs, using the method of matrix inversion (FIG. 13A), are also shown in FIG. 17 for the three respective samples. Each of the resulting dPHDs clearly confirms (even in this tabular format) the trimodal nature of each distribution, showing relatively "clean" separation of the three latex size standards (given the limitations on resolution imposed by the use of 32 channels). The "smearing" of pulse heights across a wide spectrum seen in the original PHDs due to the dependence of sensor response on particle trajectory has been successfully "removed" by the straightforward matrix inversion procedure, with no assumptions made concerning the shape of the underlying PSD.

Several details are noteworthy. First, DPHD results of relatively high quality—i.e. containing few (and only low-amplitude) spurious "noise" contributions, as shown in FIG. 17, can be consistently obtained using the new SPOS method by "cleaning up" the matrix used to invert the measured PHD data. This consists of setting equal to zero the secondary entries (most of which typically are relatively small to begin with) that lie below the unit elements on the diagonal. These terms correspond to counts for pulse height values greater than the maximum count pulse height value in the column. Second, each of the dPHDs generated by the matrix inversion algorithm typically contains several negative values for various channels (bins). These non-physical values are arbitrarily set equal to zero, for obvious reasons. The entries in the remaining channels are then renormalized, so that the total number of particles equals the total number of counts originally collected in the corresponding measured PHD. Third, the pulse height values associated with the three main peaks (i.e. the channels having the three largest number of particles) observed for the dPHDs in FIG. 17 are the same for all three samples—65 mV (Row 12), 198 mV (Row 17) and 309 mV (Row 19). Interpolation of the calibration curve of FIG. 8A yields the corresponding particle diameters—0.94 μm, 1.31 μm and 1.55 μm. These values should be considered to be in good agreement with the known sizes, given the limited resolution associated with the 32 channels chosen for the matrix inversion calculation. Finally, the expected progressive, factor-of-two decrease in the number of 0.993-μm particles (Row 12) in going from sample A to B to C is indeed observed, at least approximately (discussed below).

Next, it is useful to compare these results with the dPHDs obtained from the same starting PHD data using the novel method of successive subtraction, with the same 32-channel resolution. The matrix and measured PHD column vectors are the same as those used for matrix inversion. The resulting dPHDs obtained using the successive subtraction algorithm are also shown in FIG. 17. Clearly, there is very good agreement, from channel to channel (i.e. row to row in the dPHD column vectors), between the values generated by the two different deconvolution procedures. Specifically, there is substantial agreement for the channels associated with the three expected latex peaks, encompassing rows 11-3 and 16-22. The only deviations concern the occasional spurious entries of low amplitude, most prevalent in lower pulse-height channels (i.e. rows # 1-10). They occur because of inadequacies in the inversion algorithms, given inevitable statistical noise in the underlying PHD data. More of these contributions appear to be generated by the matrix inversion method than by the successive subtraction algorithm. This should not be surprising, given the additional "information" possessed by the latter method and the fact that the dPHD thus produced evolves systematically, from largest to smallest pulse-height channels. In any case, apart from the small noise contributions noted above, one can conclude that the dPHD results produced by the two deconvolution procedures are: 1) very good, concerning both absolute accuracy (i.e. particle diameters corresponding to pulse-height values) and resolution; and 2) substantially the same.

These conclusions are reinforced by the dPHD results obtained from the same PHD data using higher, 64-channel resolution. The starting PHDs now consist of 64×1 column vectors, corresponding to the 64-channel data shown in FIGS. 15A, B, C. The matrix is a 64×64 array, having four times the number of entries as the matrix shown in FIGS. 16A and 16B.

Again, nine measured basis vectors were used as a starting point for constructing the 64×64 matrix. The new 64×1 (column) vectors were obtained from the same measured PHDs that produced the 32×1 basis vectors used in the preceding analysis. The new vectors occupy columns #11 (0.722-μm), #15 (0.806-μm), #24 (0.993-μm), #34 (1.361-μm), #37 (1.588-μm), #41 (2.013-μm), #51 (5.03-μm), #58 (10.15-μm) and #61 (20.0-μm).

Figure 18A:
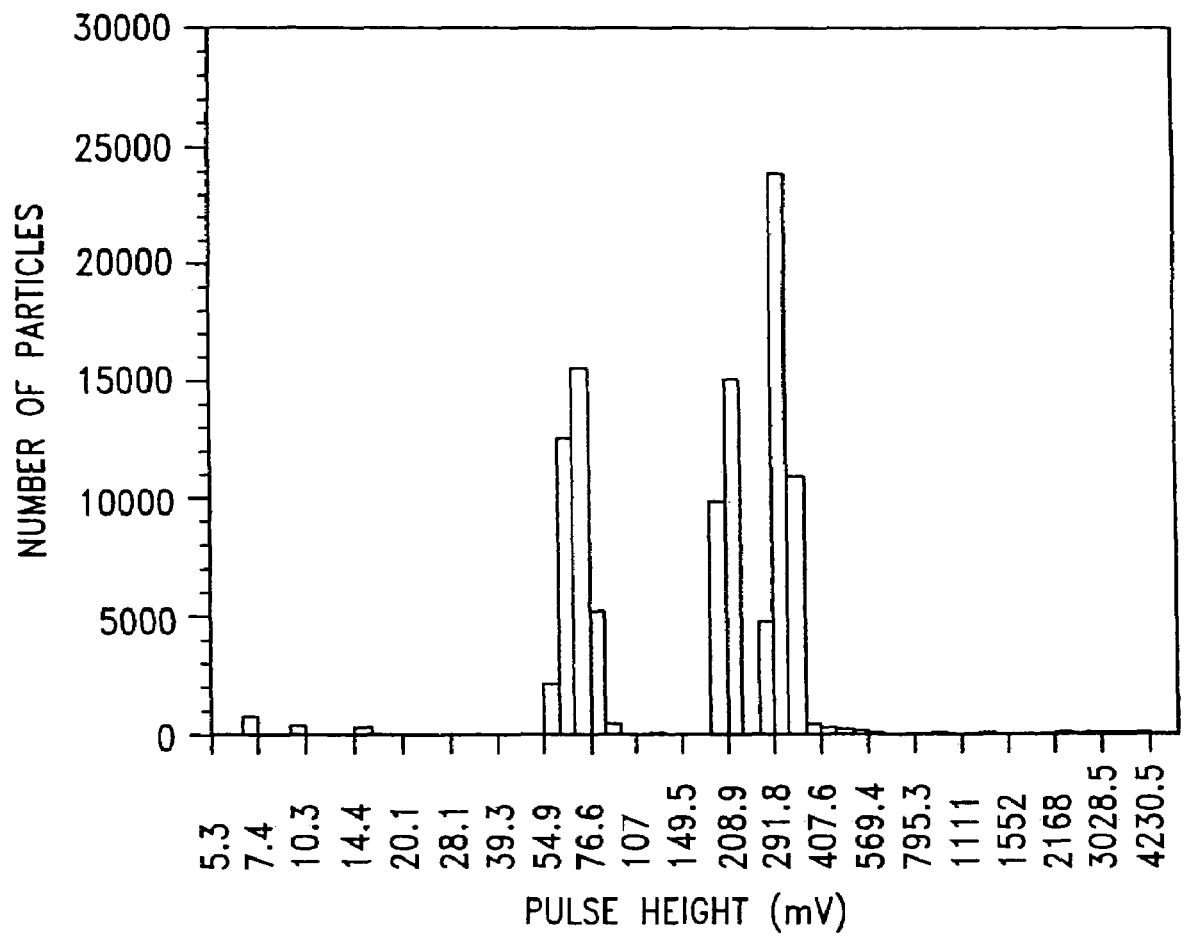
FIG. 18A shows the computed dPHD (64-channels) obtained from the measured PHD for sample "A" (latex trimodal, FIG. 15A), using the matrix inversion algorithm.
Figure 18B:
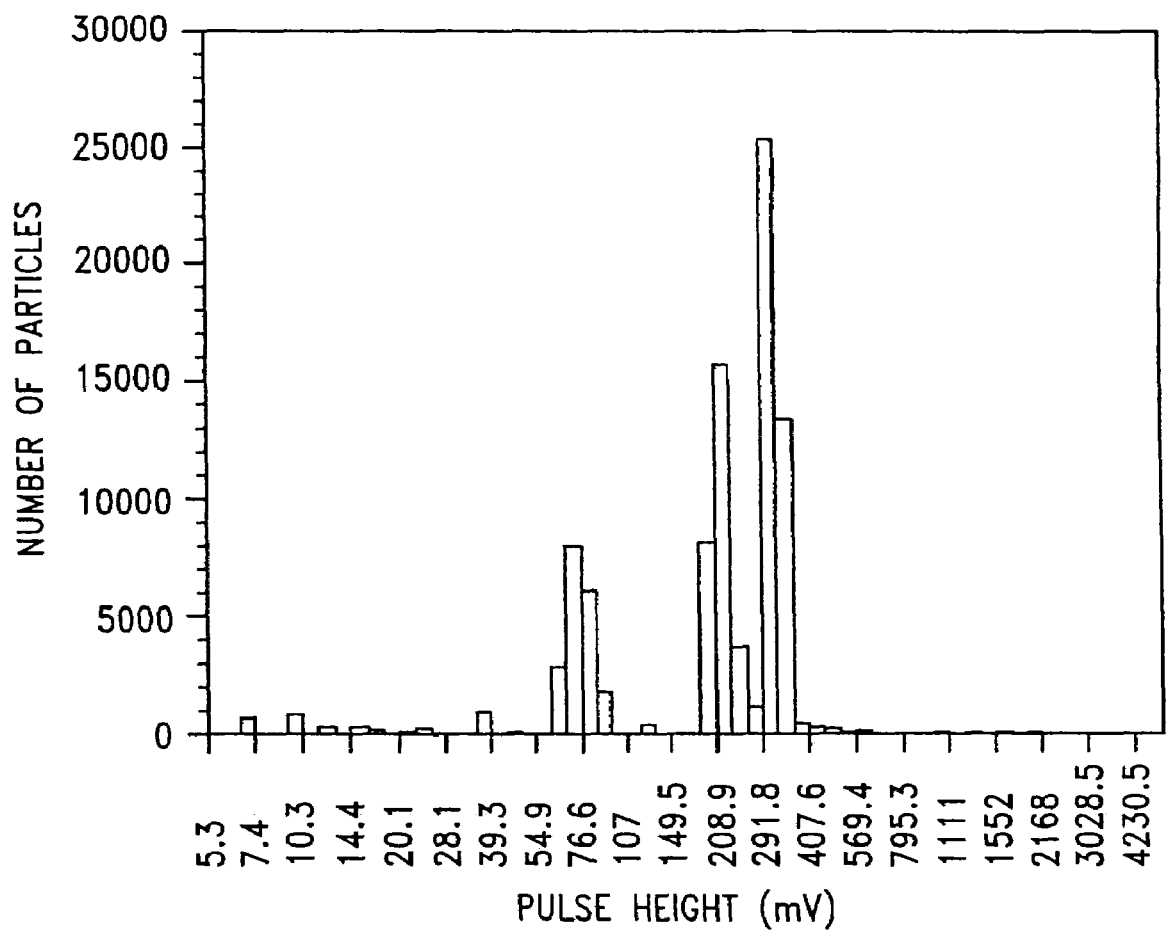
FIG. 18B shows the computed dPHD obtained from the measured PHD for sample "B" (latex trimodal, FIG. 15B), using the matrix inversion algorithm.
Figure 18C:
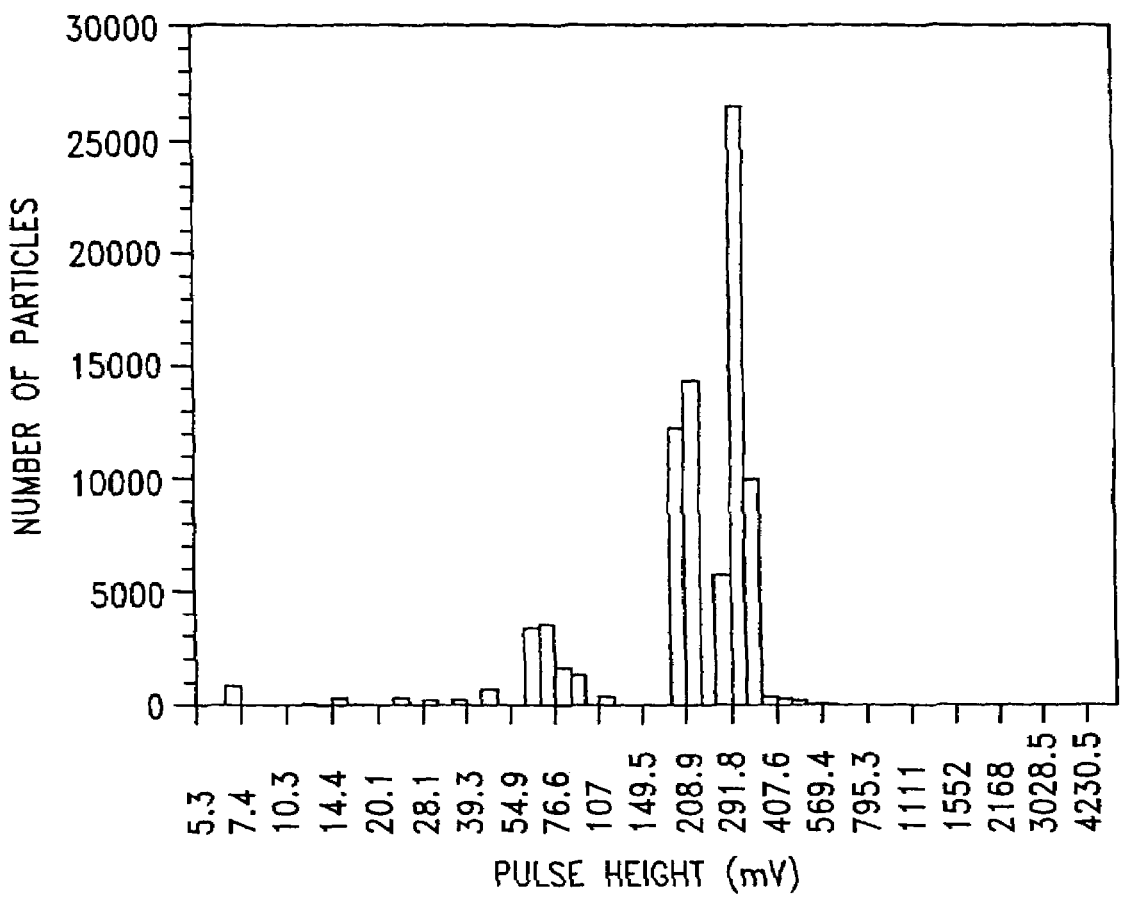
FIG. 18C shows the computed dPHD obtained from the measured PHD for sample "C" (latex trimodal, FIG. 15C), using the matrix inversion algorithm.

The resulting 64-channel dPHDs obtained by matrix inversion are shown in FIGS. 18A, B, C. The corresponding results obtained by successive subtraction are shown in FIGS. 19A, B, C. Again, the agreement between the two sets of results is excellent, comparable to the agreement observed using 32-channel resolution, summarized in FIG. 17. As before, the three peaks are cleanly separated, but with the advantage of having twice the pulse-height resolution. There remain some minor "noise" contributions observed in the lower pulse-height region of the matrix inversion results (FIGS. 18A, B, C), whereas there are almost no artifacts observed for the 64-channel successive subtraction results (FIGS. 19A, B, C). Hence, one can again conclude that the dPHD results obtained using the successive subtraction algorithm are marginally better than those obtained by simple matrix inversion.

Figure 20A:
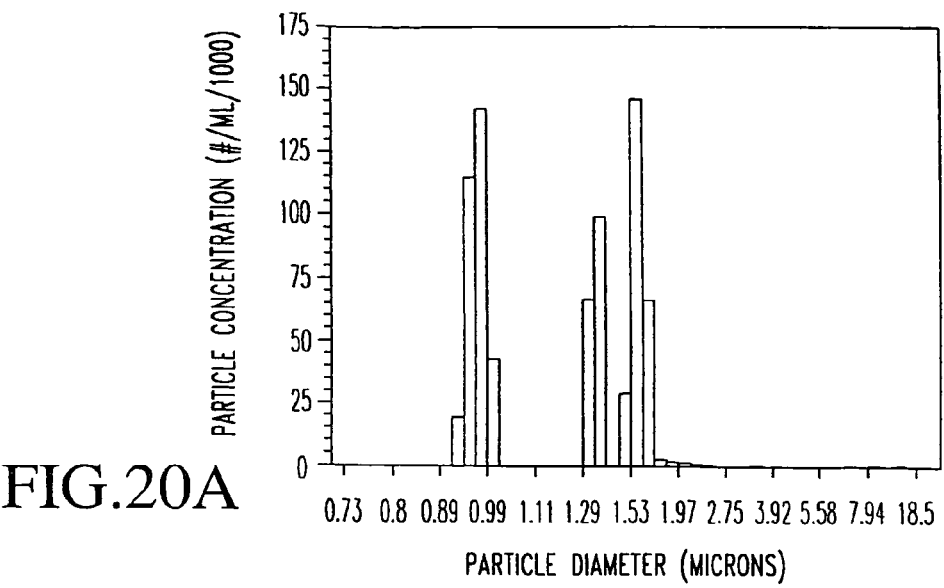
FIG. 20A shows the PSD (concentration) obtained for sample "A" from the computed dPHD (FIG. 19A), using the calibration curve (FIG. 8A) and sensor efficiency (FIG. 9)
Figure 20B:
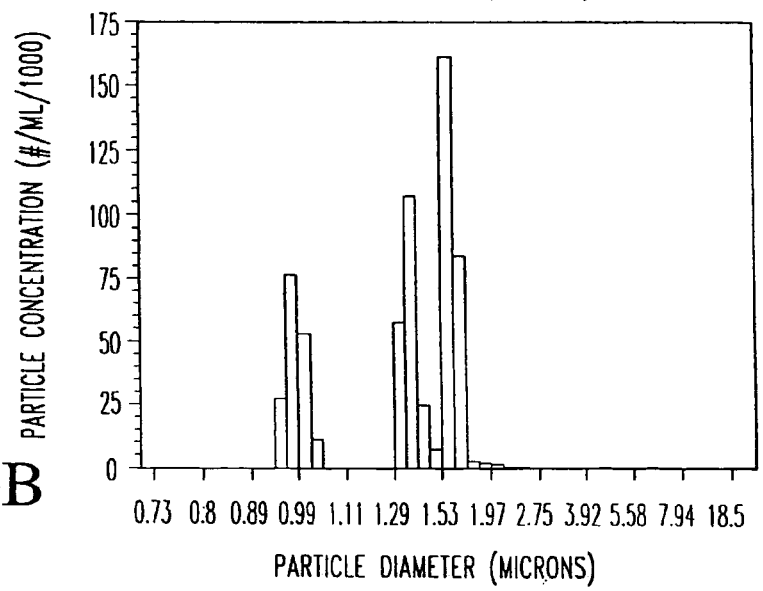
FIG. 20B shows the PSD (concentration) obtained for sample "B" from the computed dPHD (FIG. 19B), using the calibration curve (FIG. 8A) and sensor efficiency (FIG. 9)
Figure 20C:
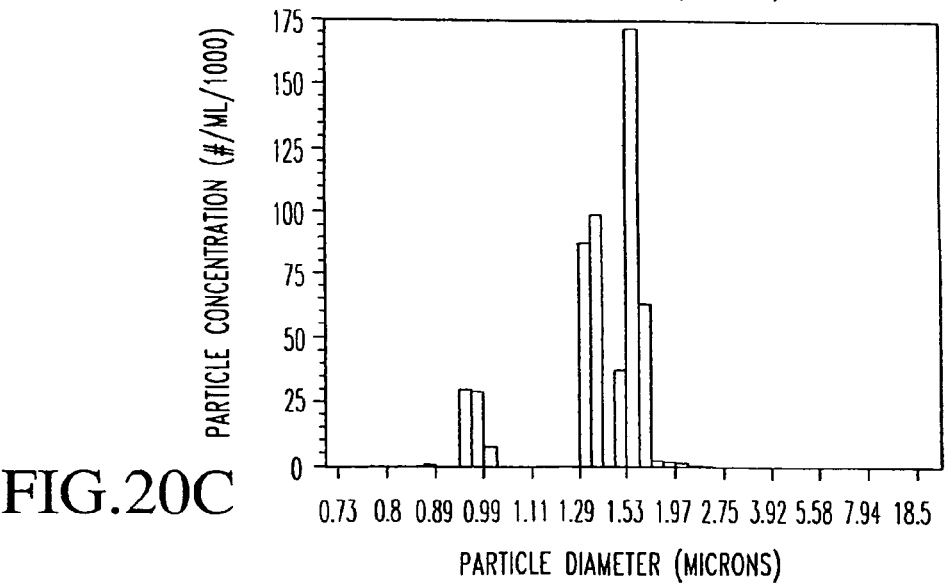
FIG. 20C shows the PSD (concentration) obtained for sample "C" from the computed dPHD (FIG. 19C), using the calibration curve (FIG. 8A) and sensor efficiency (FIG. 9)

Only two, straightforward computational procedures remain in order to convert the dPHD results (from either deconvolution algorithm) into the desired final PSD results. First, the DPHD must be transformed into a "raw" PSD, using the standard calibration curve that applies for the sensor utilized—i.e. the plot shown in FIG. 8A. Second, the resulting raw PSD must be renormalized, taking into account the relatively low sensor efficiency, $\phi_d$, for all particle sizes measured. The number of particles contained in each channel of the raw PSD must therefore be multiplied by the factor $1/\phi_d$ that pertains to the diameter, d, for that channel, where $\phi_d$ is obtained from FIG. 9 by interpolation. The resulting renormalized values represent the number of particles of each size estimated to have been in the volume of sample suspension that passed through the sensor during data collection. Dividing these numbers by the sample volume (16-ml for the trimodal latex samples discussed above) yields the concentration of particles of each size estimated to be in the sample suspension. The resulting "concentration" PSDs, corresponding to the dPHDs obtained by successive subtraction (FIGS. 19A, B and C) and expressed as the number of particles per ml of sample suspension (divided by 1000), are shown in FIGS. 20A, B, C.

It is instructive to compare the particle concentrations found in each population peak in the three PSDs obtained using the new LE-type sensor with estimates obtained independently. The concentrations of the individual stock latex suspensions used to prepare samples A, B and C were measured using a conventional (combined LE+LS) SPOS instrument with 100% counting efficiency. Much higher dilution factors were required in order to avoid distortions in the measured PSDs caused by coincidence effects. These comparisons are summarized in Table II. The contributions of the individual histogram bars belonging to each of the three "peaks" in the concentration PSDs of FIGS. 20A, B, C were added together to obtain the concentrations shown for each latex standard size.

Clearly, the agreements are very good, considering the limitations inherent in any deconvolution procedure that would be employed, including the two methods discussed herein. Of course, neither the resolution nor the absolute accuracy of the PSDs obtained using the new LE-type sensor can be expected to be quite as good as what would be obtained using a conventional sensor. Nevertheless, the quality of the results obtained using the new LE-type sensor should be considered excellent, given the radically different optical design utilized and the relatively sophisticated deconvolution methods required. Finally, it is important to acknowledge that the PSD results shown in FIGS. 20A, B, C are greatly superior to the typical results that would be produced by any "ensemble" technique, in which particles of all sizes contribute simultaneously to the measured signal. The latter must then be inverted, using an appropriate algorithm, to obtain an estimated PSD, usually having relatively limited resolution and accuracy. Such ensemble techniques include ultrasonic attenuation as a function of frequency and, notably, "laser diffraction," based on a combination of classical Mie scattering and Fraunhofer diffraction.

Next, it is instructive to examine the response of the new LE-type sensor for a sample suspension containing a continuous ("smooth"), relatively broad distribution of particle diameters. Specifically, it is useful to focus on a colloidal suspension that is "mostly submicron," in which the great majority of particles, even on a volume-weighted basis, are smaller than one micron (1 μm). There are many applications of both commercial and research significance that involve the use of such colloidal suspensions. Examples include: 1) aqueous "slurries" of ultrafine inorganic particles—usually oxides, such as silica, alumina and cerium oxide—used for CMP processing of silicon wafer surfaces during fabrication of semiconductor integrated circuits; 2) homogenized oil-in-water emulsions designed for intravenous injection, used for parenteral nutrition, drug delivery (e.g. anesthesia) and as contrast agents for ultrasound imaging; 3) inks, dyes and pigments, used for both ink-jet and conventional printing; 4) homogenized artificial drink emulsions, consisting of edible oil droplets, containing flavor and coloring agents, coated with an emulsifier and suspended in water; 5) aqueous paper coating dispersions, typically containing calcium carbonate, kaolin clay, titanium dioxide or organic polymers, such as latex; 6) polymer suspensions, used in paints, coatings and adhesives.

For these and other applications it is often very useful to be able to determine the number and size distribution of the largest particles in the sample suspension—i.e. those that comprise the outermost "tail" of the PSD, e.g. larger than 1 μm. Knowledge of the volume, or mass, fraction of the particles in the PSD tail (i.e. percentage of the total particle volume, or mass) often provides a clear indication of the quality and/or stability of the emulsion, suspension or dispersion in question. If the material is colloidally unstable, the volume fraction of particles occupying the PSD tail will "grow" over time, as the system moves toward irreversible agglomeration and/or phase separation. Characterization of the entire PSD, typically requiring an "ensemble" technique, such as laser diffraction or dynamic light scattering, by nature usually lacks the sensitivity needed to detect small changes in the PSD associated with the early stages of particle/droplet agglomeration. Instead, the SPOS technique is able to detect quantitatively very small changes in the PSD associated with various stages of instability, because it responds only to the relatively large particles that comprise the outermost tail of the PSD. This tail may constitute only a very small fraction (typically <0.1%) of the particles that populate the overall PSD, even on a volume-weighted basis. However, this small fraction of the PSD frequently provides a unique "window" on the stability of the overall suspension.

The same can be said regarding the power of the SPOS technique to reveal the quality of a suspension or dispersion. SPOS methods have proven to be very useful, if not essential, for determining the quality of many particle-based products, even when long-term stability is not in question. The quality of such products or intermediate process materials is often correlated strongly with the percentage of particles that populate the outlier region of the PSD tail. Their presence must often be minimized, or excluded altogether, in order to ensure product quality and performance. The number- or volume-weighted PSD obtained for the tail can therefore be used to optimize the parameters that control the particle manufacturing process. Examples of the latter include homogenization and Microfluidization™ (Microfluidics Corp., Newton, Mass.) for preparation of oil/water emulsions, where the pressure, temperature, orifice size, stoichiometry of constituents, the number of passes and other variables influence the PSD. Other examples include emulsion polymerization (using batch, semi-batch or continuous reactors) for production of polymers, and milling and grinding of powders. The superiority of the conventional LE-type SPOS method compared to laser diffraction for determining the stability and quality of injectable fat emulsions is described by D. F. Driscoll et al, in Int'l J. Pharm., vol. 219, pp. 21-37 (2001).

The new LE-type sensing method offers two potentially significant advantages over its conventional counterpart. First, much less dilution of the starting concentrated suspension is required. This feature is often very important—i.e. for systems that may become colloidally unstable, and therefore susceptible to agglomeration, due to the extensive dilution usually required by conventional LE or LS sensors in order to avoid particle coincidences. An important example includes CMP slurries, stabilized by electrical charges on the particle surfaces, maintained by the relatively high or low pH of the surrounding fluid. Significant (e.g. 100- or 1000-fold) dilution of these slurries can change the pH sufficiently to significantly decrease the electrical potential on the particles, allowing Van der Waals attractive forces between neighboring particles to overcome electrostatic repulsions, thus promoting agglomeration.

Second, the new LE-type SPOS method can usually achieve an acceptable low size threshold (e.g. <0.7 μm) without needing to resort to a separate LS measurement—i.e. using light extinction alone. The resulting LE-type signal is relatively insensitive to deterioration of the inner surfaces of the flow channel due to absorbance (coating) of particles or chemically induced damage (e.g. etching) caused by the suspending fluid. While these effects can significantly degrade the performance of an LS-type sensor, due to strong scattering at the fluid-surface interfaces, they usually have relatively little effect on the quality of the LE signal, except in extreme cases. Therefore, the requirements for maintenance (cleaning) of the flow cell can be expected to be relatively modest over extended times for most important applications.

Figure 21A:
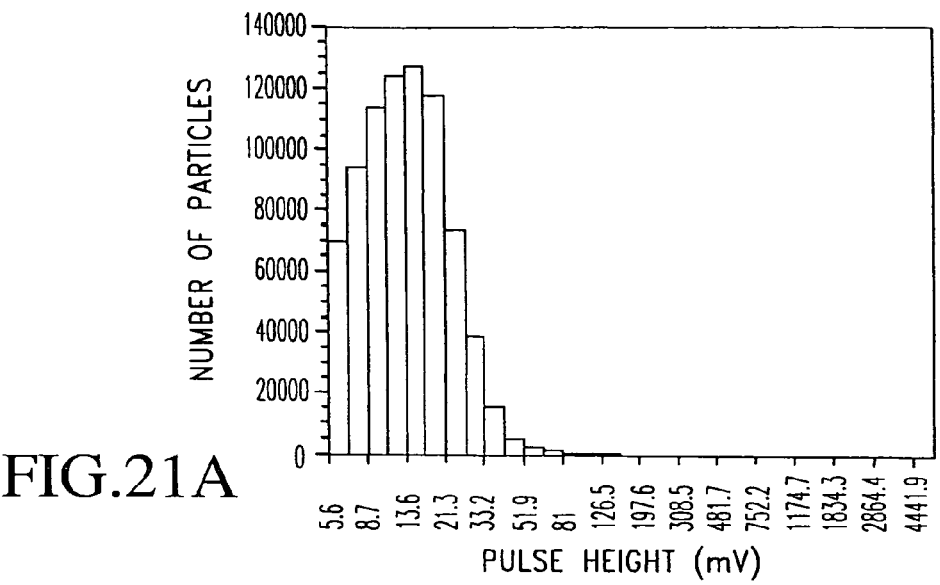
FIG. 21A shows the measured PHD (32-channels) obtained for a sample of fat emulsion (0.05% by volume)
Figure 21B:
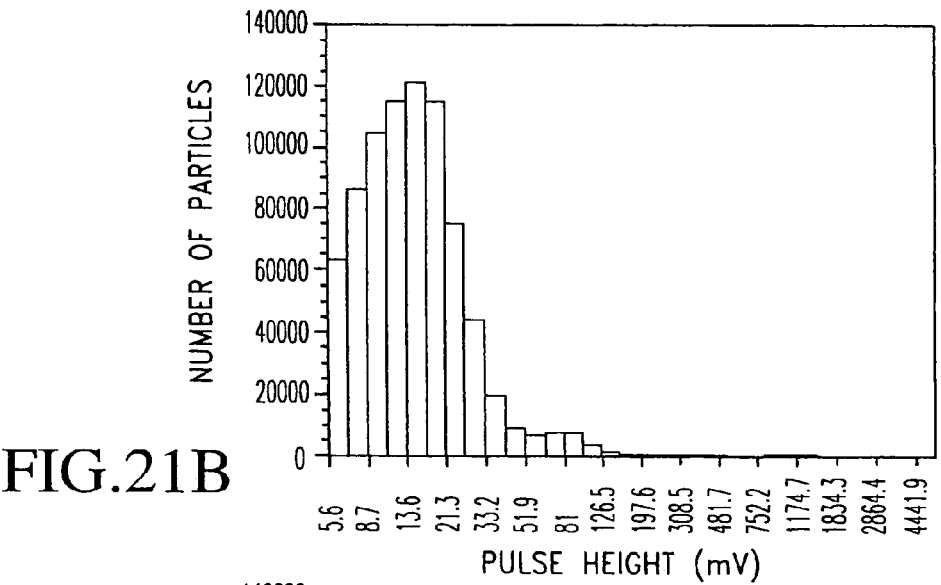
FIG. 21B shows the measured PHD obtained for the same sample as used in FIG. 21A, but with an added, low-concentration "spike" of 0.993-μm latex particles ($3.25 \times 10^5$/ml)
Figure 21C:
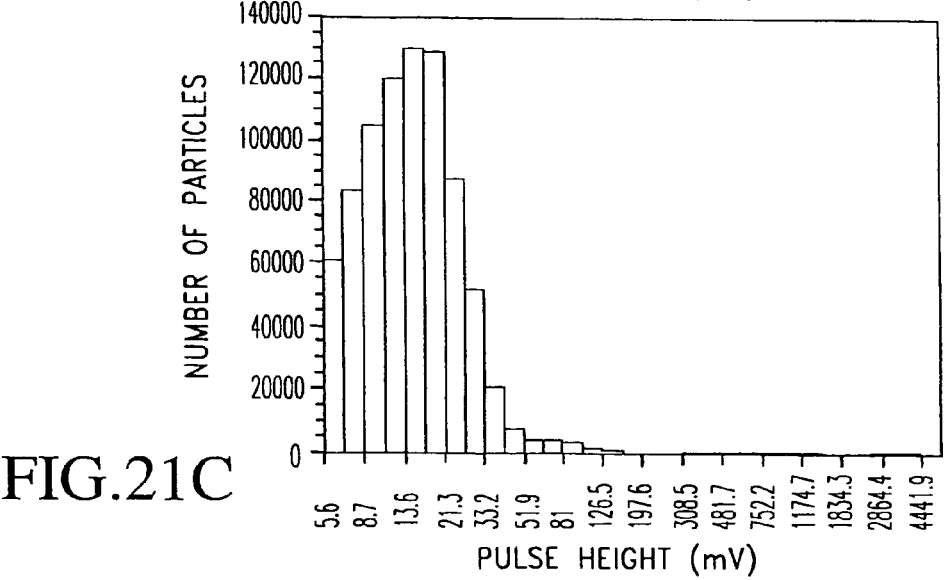
FIG. 21C shows the measured PHD obtained for the same sample as used in FIG. 21B, but with only 25% of the added "spike" of 0.993-μm latex particles ($8.13 \times 10^4$/ml)

With these considerations in mind, it is useful to review some typical results that can be achieved by the new LE-type sensor for a typical, relatively concentrated colloidal suspension. FIGS. 21A, B, C to 23A, B, C summarize the results obtained for three samples containing injectable (oil-in-water) fat emulsion, used for parenteral nutrition. Each sample contained a fat droplet concentration of approximately 0.05% (by volume), obtained from a 400:1 dilution of the "stock" lipid emulsion (Liposyn III, 20% (w/v), Abbott Laboratories, N. Chicago, Ill.). This is equivalent to a droplet volume fraction of $5 \times 10^4$ ml per ml of final suspension. Sample "A" contained only fat droplets, while "B" and "C" contained added amounts of uniform 0.993-μm polystyrene latex particles—$3.25 \times 10^5$ particles/ml for "B" and $8.13 \times 10^4$ particles/ml for "C." Expressed in terms of volume fraction, the added latex "spikes" are equivalent to $1.67 \times 10^{-7}$ ml per ml of suspension for "B" and $4.17 \times 10^{-8}$ ml per ml of suspension for "C." Compared to the volume fraction of fat droplets, the added latex spike concentrations are equivalent to 334 ppm (parts per million) and 84 ppm, respectively.

FIGS. 21A, B, C show the measured PHDs obtained for the three respective samples, using 32 pulse height channels, evenly spaced on a logarithmic scale. In each case data were collected from a sample volume of 16 ml, at a flow rate of 20 ml/min, over a 48-sec period. For pulse heights above approximately 14 mV, the PHD for sample A shows a smoothly decreasing number of detected particles with increasing pulse height. This is not surprising, given the fact (confirmed below) that the underlying PSD should have a similarly decaying population with increasing droplet size for droplets larger than the mean size of the distribution, approximately 0.2 μm. The fact that the PHDs decrease below 14 mV is a consequence of the fact that particles with maximum pulse heights, $^M\Delta V_{LE}$, smaller than this value are too small to be detected individually (i.e. below approximately 0.7 μm) for the sensor utilized. The sensor efficiency falls off precipitously below this level. The PHD for sample B clearly shows the perturbation due to the added latex spike. The same is true for the PHD generated by sample C, with a considerably smaller effect due to the 4× reduction in added latex particles.

Figure 22A:
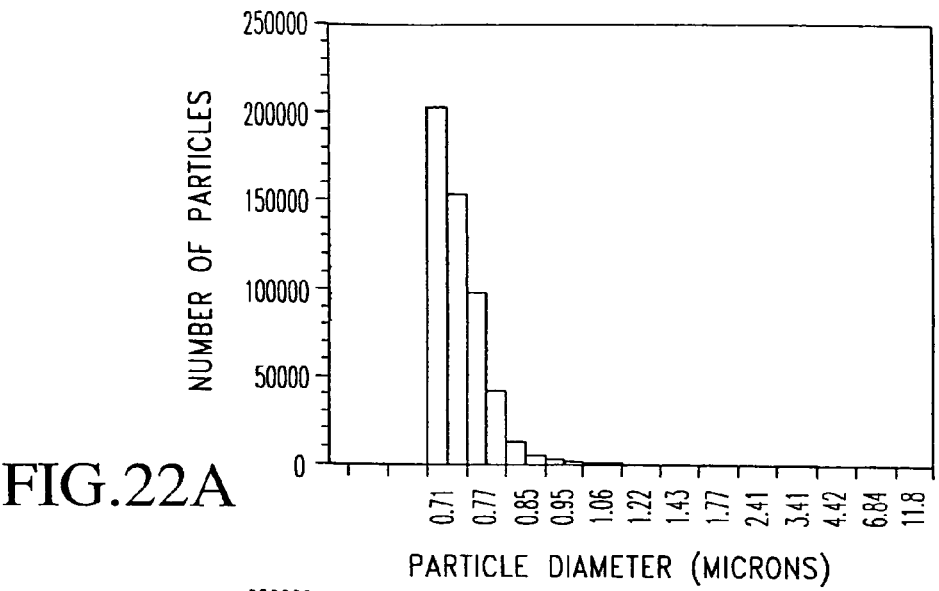
FIG. 22A shows the computed dPHD (valid pulse-ht region) obtained by deconvolution (successive subtraction) of the PHD in FIG. 21A.
Figure 22B:
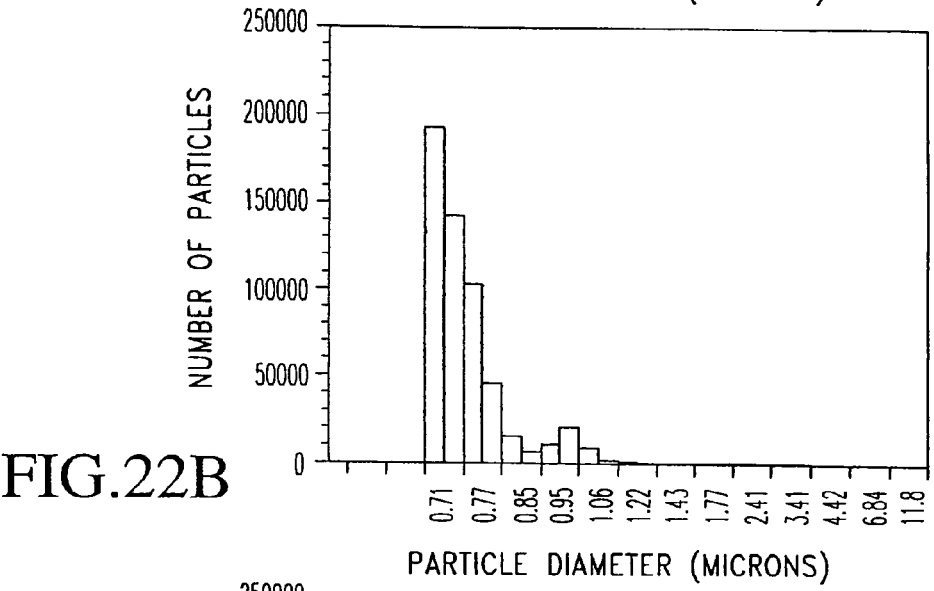
FIG. 22B shows the computed dPHD (valid pulse-ht region) obtained by deconvolution (successive subtraction) of the PHD in FIG. 21B.
Figure 22C:
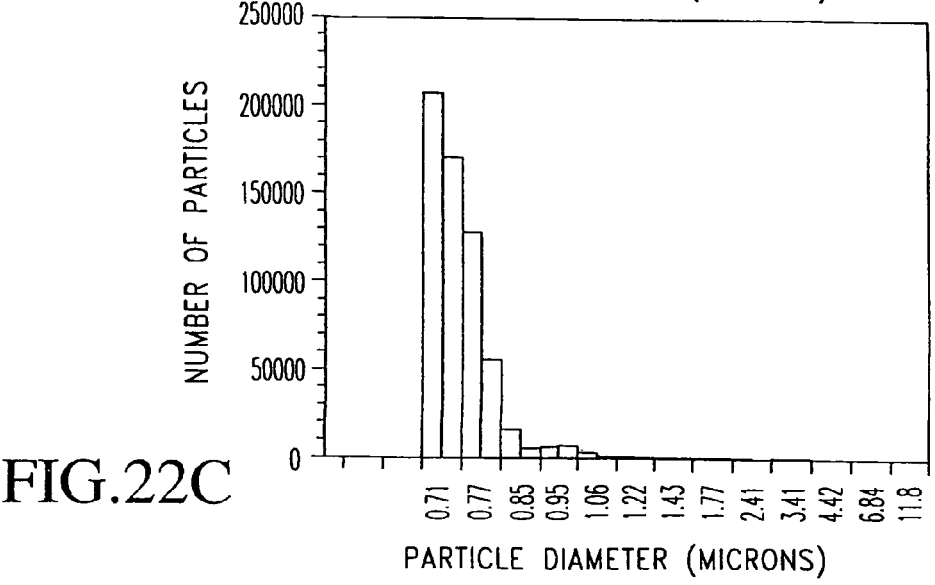
FIG. 22C shows the computed dPHD (valid pulse-ht region) obtained by deconvolution (successive subtraction) of the PHD in FIG. 21C.

FIGS. 22A, B, C show the dPHDs obtained by deconvolution of the PHDs of FIGS. 21A, B, C, respectively, using the successive subtraction algorithm. The dPHDs exhibit the expected decaying behavior, mimicking the expected underlying size distribution of fat droplets. The added latex spike is now more clearly recognizable in FIG. 22B and, to a lesser extent, in FIG. 22C. The dPHDs are shown only for $^M\Delta V_{LE} \geq 21.3$ mV, because below this value the distribution is distorted and unreliable due to failing detection and resolution, as well as particle coincidence. These effects give rise to the "rollover" in the measured PHDs seen in FIGS. 21A, B, C, alluded to above.

Figure 23A:
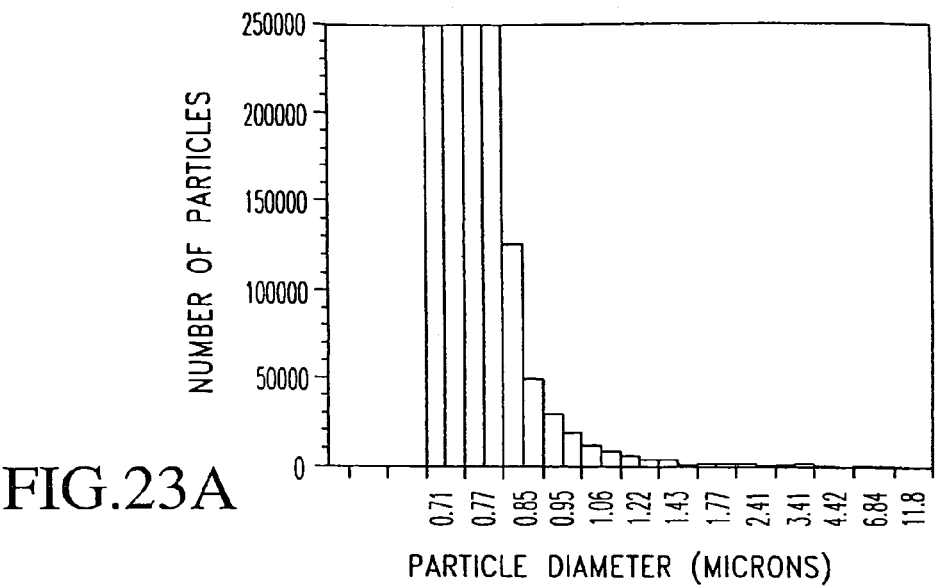
FIG. 23A shows the PSD (concentration, expanded scale) obtained from the computed dPHD (FIG. 22A), using the calibration curve (FIG. 8A) and sensor efficiency (FIG. 9)
Figure 23B:
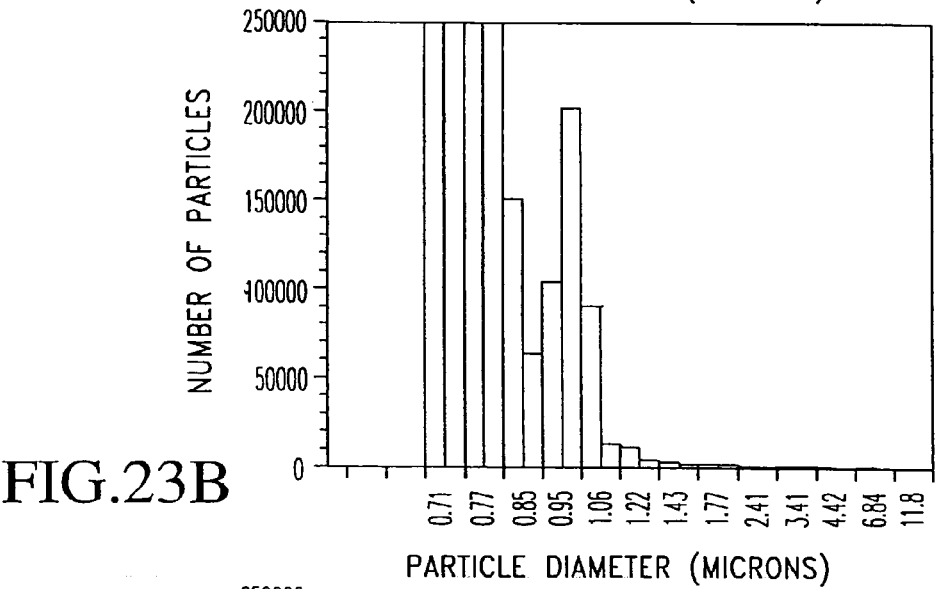
FIG. 23B shows the PSD (concentration, expanded scale) obtained from the computed dPHD (FIG. 22B), using the calibration curve (FIG. 8A) and sensor efficiency (FIG. 9)
Figure 23C:
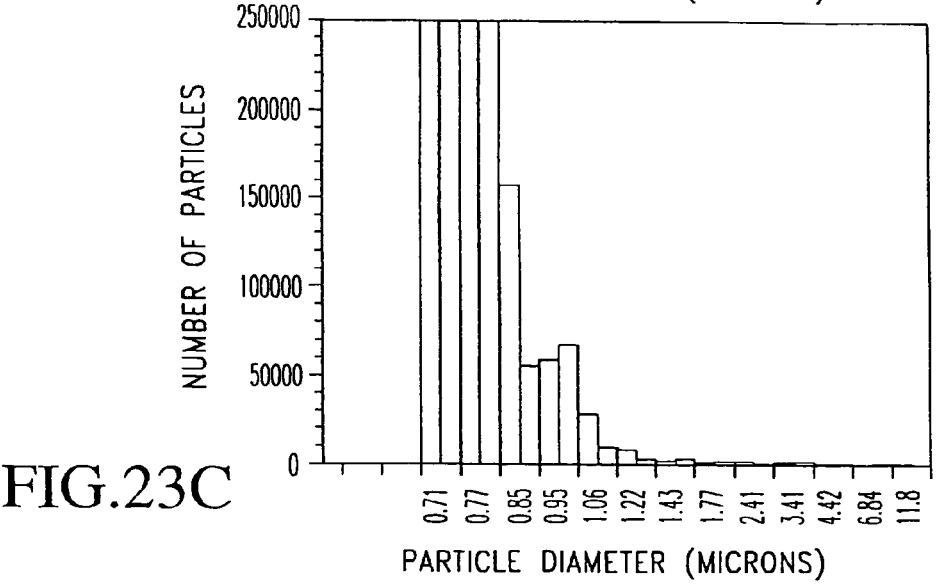
FIG. 23C shows the PSD (concentration, expanded scale) obtained from the computed dPHD (FIG. 22C), using the calibration curve (FIG. 8A) and sensor efficiency (FIG. 9)

The resulting PSDs for the three samples, expressed in terms of particle concentration in the original suspensions, are shown in FIGS. 23A, B, C. They were obtained from the corresponding dPHDs of FIGS. 22A, B, C using the calibration curve in FIG. 8A and the sensor efficiency curve in FIG. 9, as discussed earlier. The vertical concentration axis has been greatly expanded, to provide a clearer view of the details of the distributions. The influence of the added latex spikes is clearly seen in FIGS. 23B and C.

It is instructive to compare quantitatively the measured vs expected effects of each latex spike. The known concentration of added latex was approximately $2.33 \times 10^5$ particles/ml for sample B and $5.83 \times 10^4$/ml for C. The corresponding measured values are estimated by subtracting the PSD obtained for sample A from the PSDs found for samples B and C, respectively. Most of the contributions to the PSDs due to the added latex can be accounted for by considering the four histogram bars from 0.90 to 1.06 microns, inclusive. The resulting enhanced particle concentration for sample B is $3.01 \times 10^5$/ml, compared to the actual added value of $3.25 \times 10^5$/ml. The corresponding values for sample C are $8.85 \times 10^4$/ml (measured) vs $8.13`10^4$/ml (known). Both sets of values should be considered to be in very good agreement, given the relatively small concentrations of added latex particles and the inherently demanding nature of the deconvolution procedure and related calculations required to obtain the final PSDs.

The histogram plots discussed above are representative of the results that can be obtained routinely using the new LE method for the large-particle tail of the PSD for a wide variety of colloidal suspensions and dispersions. Often it is necessary, or simply convenient, to dilute the starting concentrated sample as little as possible, for the reasons mentioned earlier. Hence, in many cases the suspension passing through the flow cell is relatively highly concentrated, and therefore necessarily very turbid. Therefore, the intensity of the light transmitted through the turbid sample, over the thickness, b, of the flow channel is significantly reduced, relative to what it would be for a relatively transparent sample.

There are two consequences for the resulting LE signal, $V_{LE}$. First, the "baseline" d.c. level, $V_0$, in the absence of a particle (in the OSZ) sufficiently large to create a detectable pulse, will decrease. The new baseline voltage level, called $V^T_0$, is ideally related to the level in the absence of turbidity, $V_0$, by Beer's Law, $$V^T_0 = V_0 \exp(-\alpha x) \quad (11)$$

where x is the distance through which the light beam traverses the sample (i.e. x=b), and $\alpha$ is the coefficient of absorbance, or attenuation, usually expressed in units of cm$^{-1}$. Equation 11 can be expected to be accurate provided the sample is not excessively turbid, such that it would no longer exhibit idealized attenuation vs distance behavior, due to strong multiple scattering.

The second consequence of sample turbidity is that the (negative-going) pulses resulting from detectable particles passing through the OSZ are also diminished in height (voltage). The resulting measured pulse height, $\Delta V^T_{LE}$, for a given particle will decrease with respect to its value in the absence of turbidity, $\Delta V_{LE}$, by the same proportion that $V^T_0$ is decreased with respect to $V_0$, assuming moderate turbidity and a linear system response. Therefore, if no corrections are made to the set of pulse heights, the resulting PHD will be shifted systematically to lower pulse height values. The same will be true for the resulting dPHD, obtained by deconvolution of the PHD. Hence, the resulting PSD will be shifted to smaller particle diameters—i.e. all of the particles in the sample will be systematically undersized.

There are several methods that can be used to address the problem of shrinkage in pulse heights resulting from sample turbidity, typically caused by the large population of ultrafine particles lying below the size detection threshold—i.e. too small to contribute directly to the PHD. In the first, simplest approach, each measured pulse height can be "renormalized" (either in real time or after data collection) to its "ideal" value, $\Delta V_{LE}$, in the absence of turbidity, which is related to the measured pulse height, $\Delta V^T_{LE}$, by $$\Delta V_{LE} = (V_0/V^T_0) \times \Delta V^T_{LE} \quad (12)$$

The scale factor by which all of the measured pulse heights must be multiplied in order to obtain a new set of idealized pulse heights, corresponding to negligible turbidity, is $V_0/V^T_0$. The baseline voltage level in the absence of sample turbidity, $V_0$, can be easily measured by passing fluid substantially devoid of particles through the sensor. This value can be stored for future use whenever a turbid sample is to be analyzed, or it can be re-measured prior to each new sample analysis, using clean fluid. The baseline level in the presence of turbidity, $V^T_0$, can be measured by passing a portion of the sample suspension through the sensor, prior to data collection.

There are at least two ways in which $V^T_0$ can be determined. The easiest, analog approach consists of measuring the time-average value of the overall signal, $V_{LE}(t)$, over an appropriate period (e.g. 1 sec), using a passive or active filter, having an appropriate (RC) time constant. The average value can be measured using either a stationary or a flowing suspension. In the latter case the discrete pulses due to detectable particles will influence the measured average value. However, the extent of the influence will usually be relatively small, given that the average pulse rate is typically less than 10,000/sec and the pulse widths are usually shorter than 10-12 μsec, resulting in a "duty cycle" for the pulses of less than 10%. A second approach to measuring $VT_0$ consists of digitizing (using an analog-to-digital converter) a significant segment (e.g. 10-100 msec) of the entire signal, $V_{LE}(t)$, when the turbid sample is flowing through the sensor, and analyzing the resulting digitized signal, prior to collecting pulse height data for the sample. A computer, suitably programmed, can be used to identify and measure the "flat" (apart from small fluctuations due to noise) portions of the signal lying on either side of the discrete pulses, corresponding to the desired baseline level, $V^T_0$.

Figure 26A:
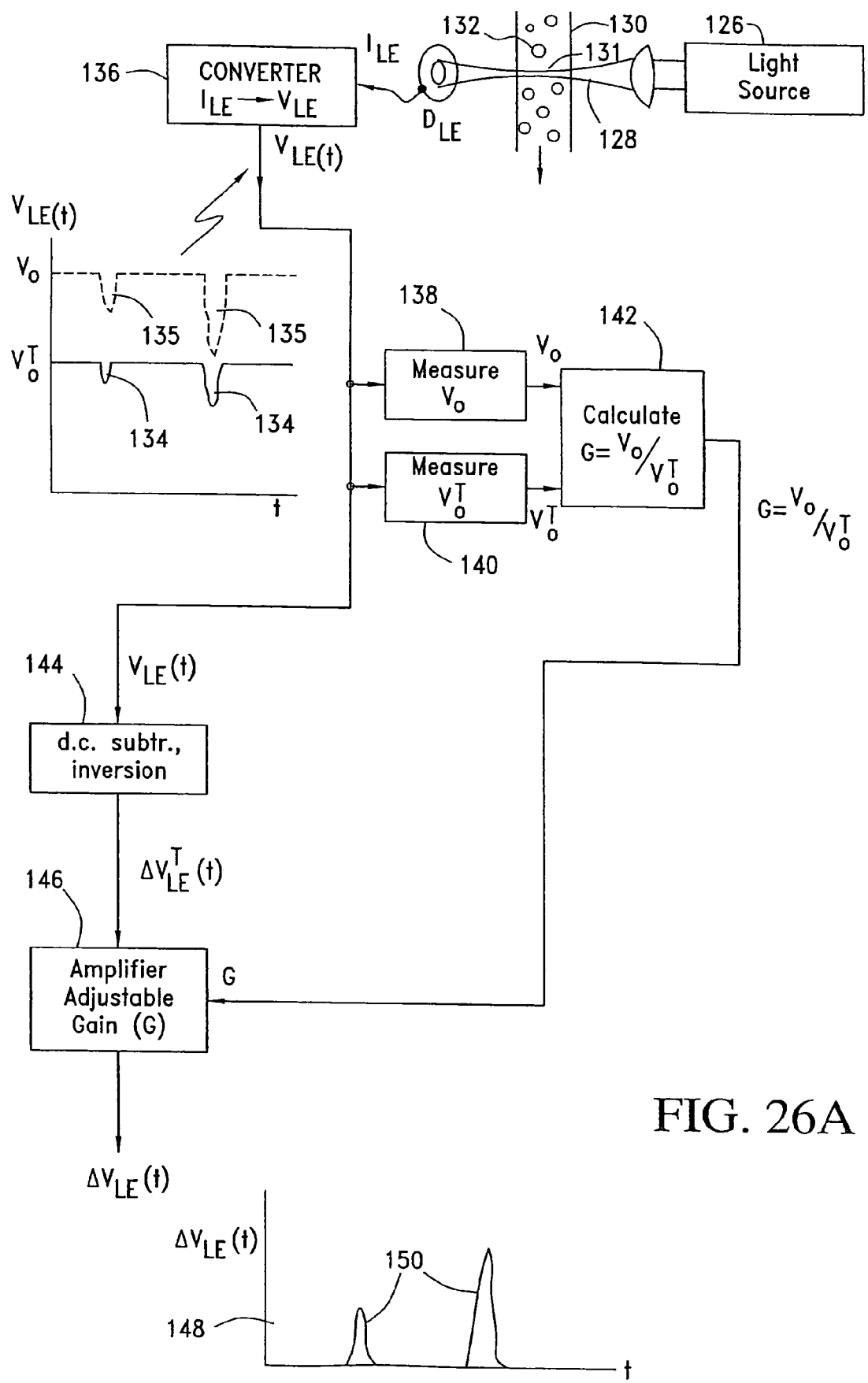
FIG. 26A, FIG. 26B, and FIG. 26C are block diagrams disclosing three techniques that can be used to compensate for the effects of sample turbidity on the signal generated by the new LE-type sensor.

FIG. 26A is a block diagram of one embodiment of means for compensation for turbidity by renormalizing the pulse heights to the value expected in the absence of turbidity. The sensor has a light source 126 and focusing lens 127 directing a beam of light 128 through a measuring flow channel 130 illuminating an optical sensing zone 131 within measurement flow channel 130. A fluid suspension of particles 132 flows through measurement flow channel 130 and a small fraction of particles 132 flowing through measurement flow channel 130 flow through optical sensing zone 131. When particles 132 pass through optical sensing zone 131, light is blocked and this is detected by a LE photodetector $D_{LE}$ as pulses 134 extending downwardly from baseline voltage $V_0^T$. It will be observed that baseline voltage $V_0^T$ and pulses 134 are both smaller than baseline voltage $V_0$ and pulses 135 which would be provided if the fluid suspension was not turbid. A converter 136 converts the current signal $I_{LE}(t)$ generated by photodectector $D_{LE}$ in response to the passage of particles 132 to a voltage signal $V_{LE}(t)$.

In order to compute a correction factor G, a non-turbid liquid is passed through the system, and the baseline voltage $V_0$ is measured at 138. Then, the specimen to be measured is passed through the system and the baseline voltage $V_0^T$ is measured at 140. The ratio $G=V_0/V_0^T$ is then calculated at 142.

The signal $V_{LE}(t)$ developed by converter 136 is processed to subtract the d.c. portion through the use of a.c. coupling and is inverted at 144. The output $\Delta V^T_{LE}(t)$ is then amplified by adjustable gain amplifier 146, the gain of which is controlled by correction factor G. The corrected signal $\Delta V_{LE}(t)$ as seen in plot 148 contains properly sized pulses with proper pulse heights 150.

Figure 24A:
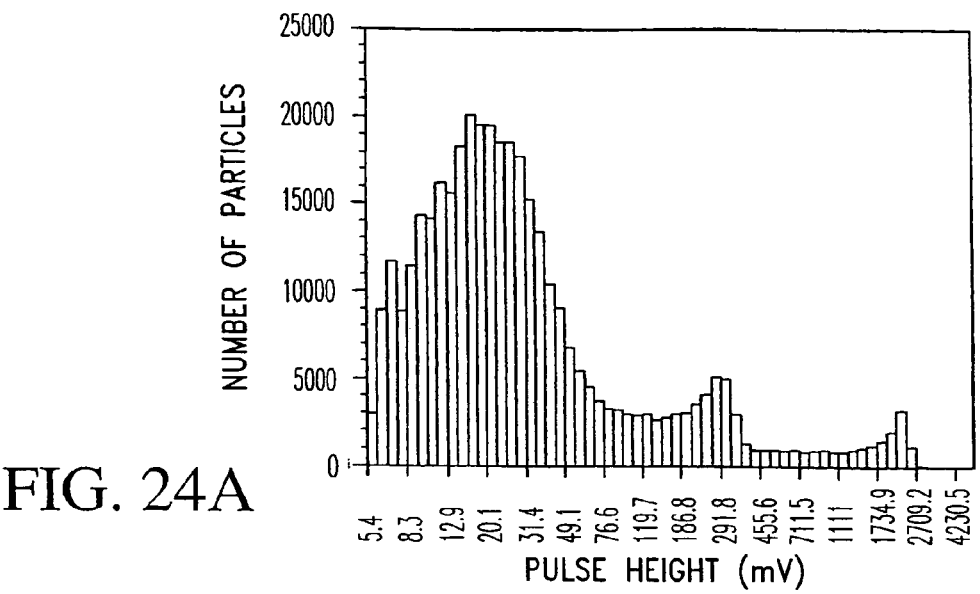
FIG. 24A shows the measured PHD (64-channels) obtained from a turbid sample containing fat emulsion (0.5% by volume) plus "spikes" of latex particles (2.013- and 10.15-μm), without correcting for the effects of sample turbidity on the signal voltage.

FIGS. 24A, B, C and 25A, B, C summarize the typical results obtained for a turbid sample before and after renormalization, respectively, of the measured pulse heights, using the first method described above. The sample consisted of a "double-spiked" suspension of relatively concentrated fat droplets, obtained from the same stock emulsion employed earlier. The fat droplet concentration was approximately 0.5% (by volume)—i.e. ten times larger than what was used for the previously discussed measurements. The resulting suspension was highly turbid from a visual point of view. Two "spikes" of uniform latex particles—2.013-μm and 10.15-μm—were added to the turbid sample suspension. The concentrations of added latex particles were large enough to yield an adequate, statistically stable number of counts during data collection, but small enough to have negligible effect on the overall turbidity of the suspension.

Figure 24B:
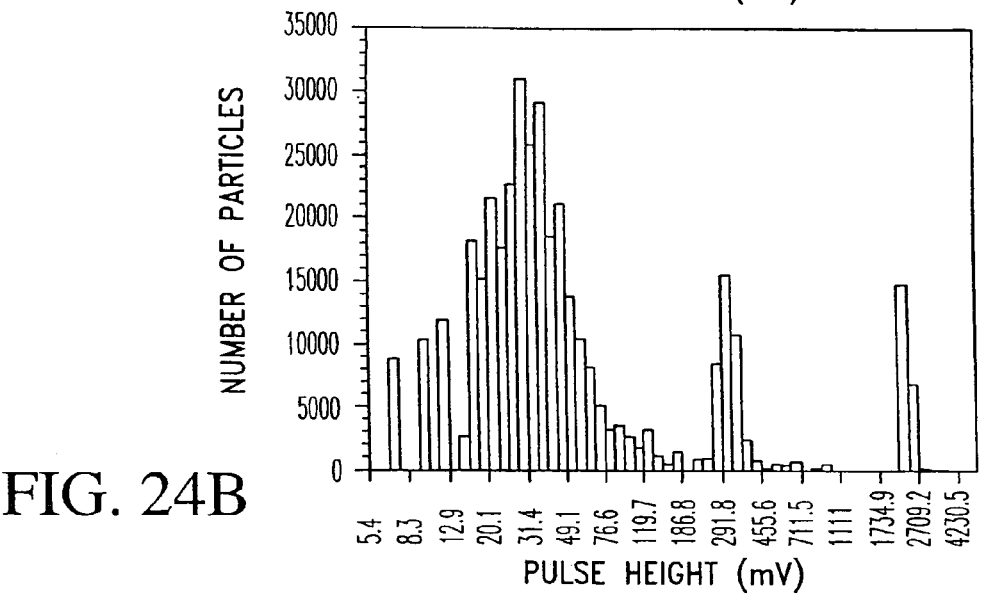
FIG. 24B shows the computed dPHD (successive subtraction) obtained from the PHD of FIG. 24A.
Figure 24C:
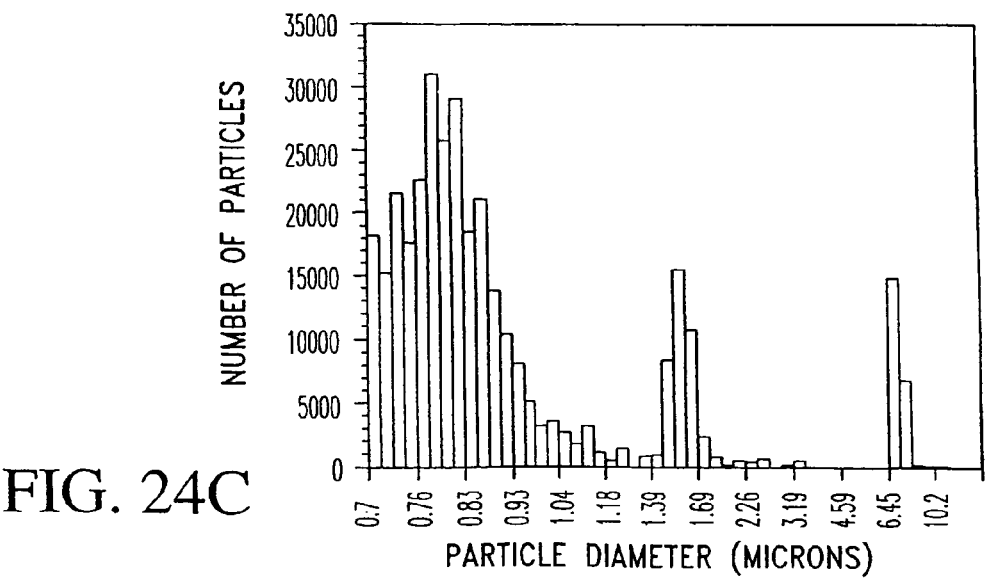
FIG. 24C shows the "raw" PSD (without correction for sensor efficiency) obtained from the computed dPHD of FIG. 24B, using the calibration curve (FIG. 8A)

FIG. 24A shows the measured PHD (64 channels) obtained for the mixture of concentrated fat droplets and added latex particles. FIG. 24B shows the resulting dPHD obtained from the PHD by deconvolution (successive subtraction). The resulting raw PSD, before correction for sensor efficiency, is shown in FIG. 24C. Clearly, the two peaks associated with the latex spikes are shifted to substantially lower diameters than the values that would be obtained for a bimodal latex mixture alone, in the absence of concentrated fat droplets. The mean diameters displayed for the two peaks are approximately 1.5-μm and 6.5-μm.

Figure 25A:
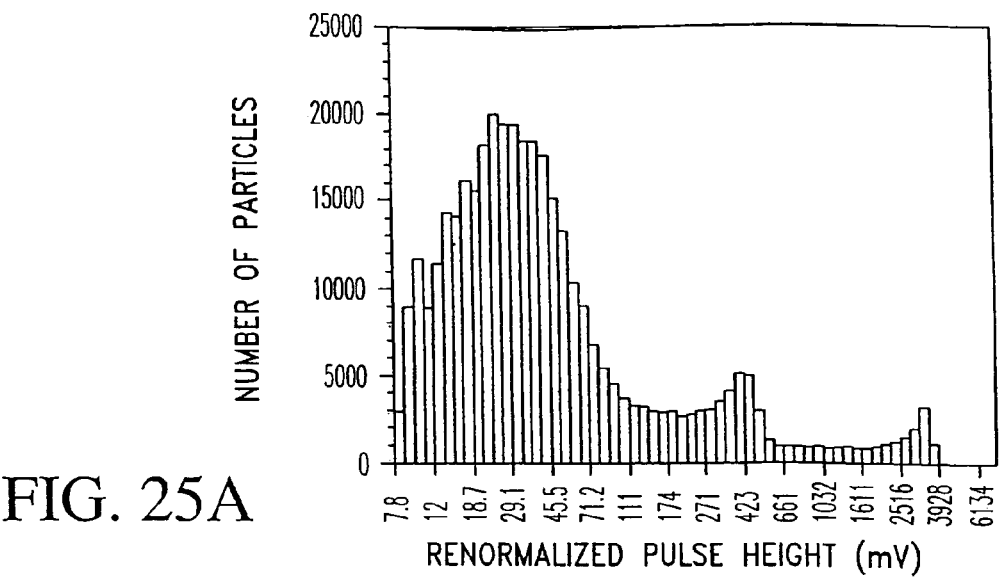
FIG. 25A shows the measured PHD (64-channels) obtained from the same sample used in FIG. 24A, but with the baseline signal level raised to its normal level in the absence of turbidity.
Figure 25B:
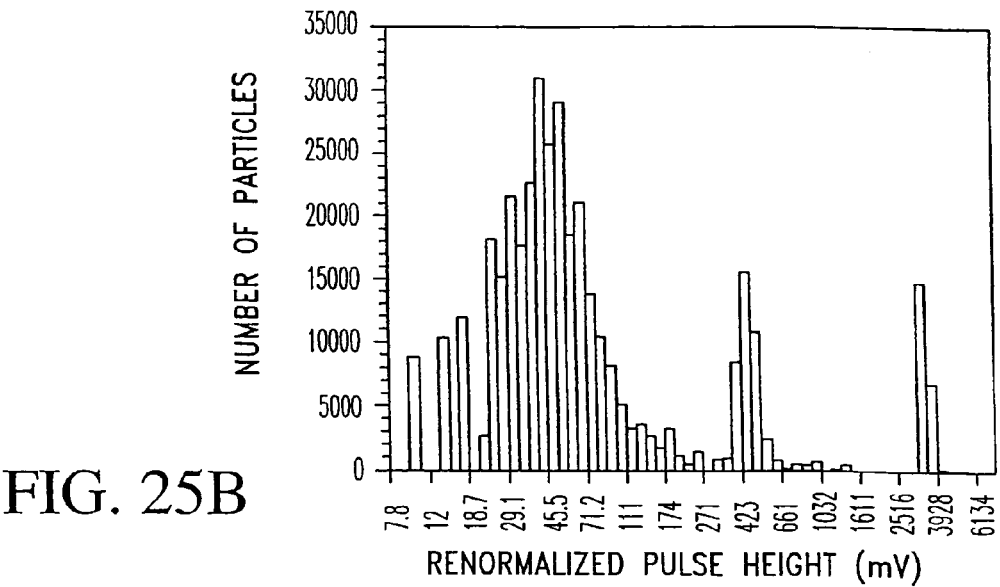
FIG. 25B shows the computed dPHD (successive subtraction) obtained from the PHD of FIG. 25A.
Figure 25C:
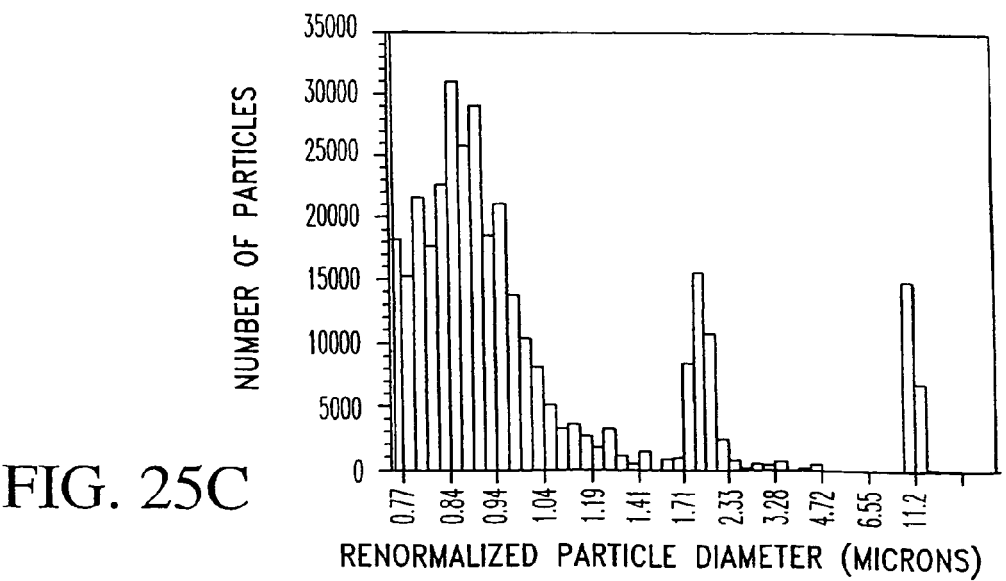
FIG. 25C shows the "raw" PSD (without correction for sensor efficiency) obtained from the computed dPHD of FIG. 25B, using the calibration curve (FIG. 8A)

The average baseline level, $V^T_0$, measured for this turbid sample was 3.45 volts—a significant decrease from the normal value of 5.00 volts, obtained in the absence of turbidity. It should therefore be possible to recover accurate PSD results by renormalizing the original PHD, using a scale factor of 5.00/3.45, or 1.45, and repeating the deconvolution calculations. The renormalized PHD is shown in FIG. 25A, and the resulting DPHD obtained by deconvolution (successive subtraction) is shown in FIG. 25B. The corresponding raw PSD is shown in FIG. 25C. The locations of the two peaks associated with the latex spikes, approximately 1.9-μm and 9.8-μm, are now very close to the expected values.

Figure 26B:
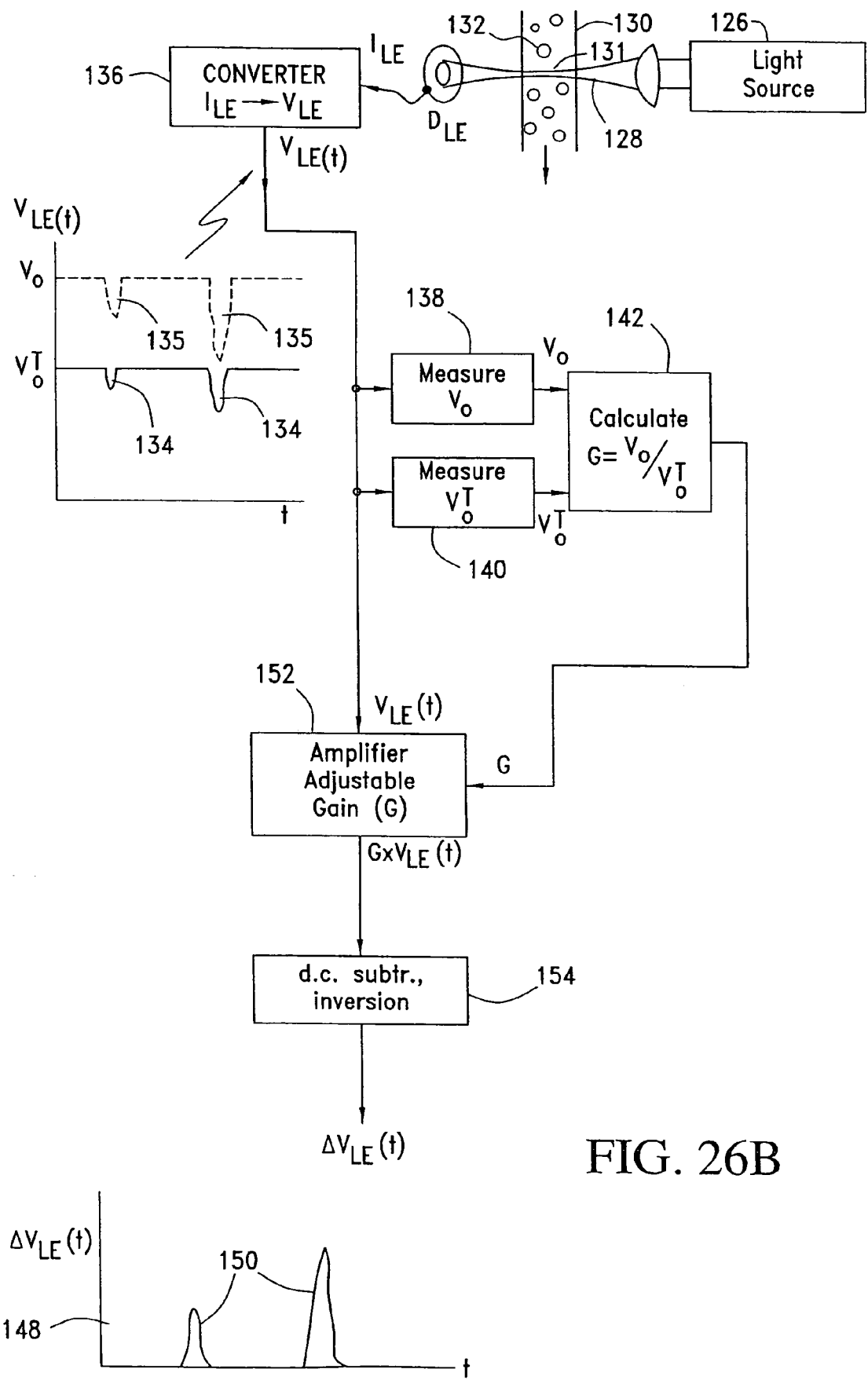

There is a second method that can be used to accommodate samples that are significantly turbid. The signal processing system can be designed to be adjusted automatically in order to substantially eliminate the effects of turbidity at the outset—i.e. before pulse height data are collected. The starting, depressed baseline level, $V^T_0$, can be increased by appropriate signal-conditioning means, so that it approximates the value, $V_0$ that would have been obtained in the absence of turbidity. For example, an amplifier means with adjustable, voltage-controlled gain can be used. A feedback circuit means can be used to sense the conditioned output signal amplitude and increase the gain of the amplifier means until the output baseline voltage reaches the desired, "ideal" level, $V_0$. This second method is illustrated in the embodiment of FIG. 26B. As before, converter 136 provides signal $V_{LE}(t)$. In this case, the signal is amplified by adjustable gain amplifier 152, the gain of which is controlled by correction factor G. The amplified signal $G \times V_{LE}(t)$ is adjusted so that the baseline level is equal to the "ideal" level $V_0$. The signal is now processed with the d.c. component subtracted and with the pulses inverted at 154, again producing the output shown in plot 148 with properly sized pulses with proper pulse heights 150.

Alternatively, the computer that is used to control the particle-sizing instrument can be used (in conjunction with a digital-to-analog converter) to control the gain of the amplifier means, so that the desired baseline level, $V_0$, is reached. In another scheme, an analog multiplier means can be used to multiply the uncorrected starting signal, $V_{LE}(t)$, by a second voltage, effectively equal to $V_0/V^T_0$, where the value of $V^T_0$ is obtained from the time average of $V_{LE}(t)$, before or during data collection.

Figure 26C:
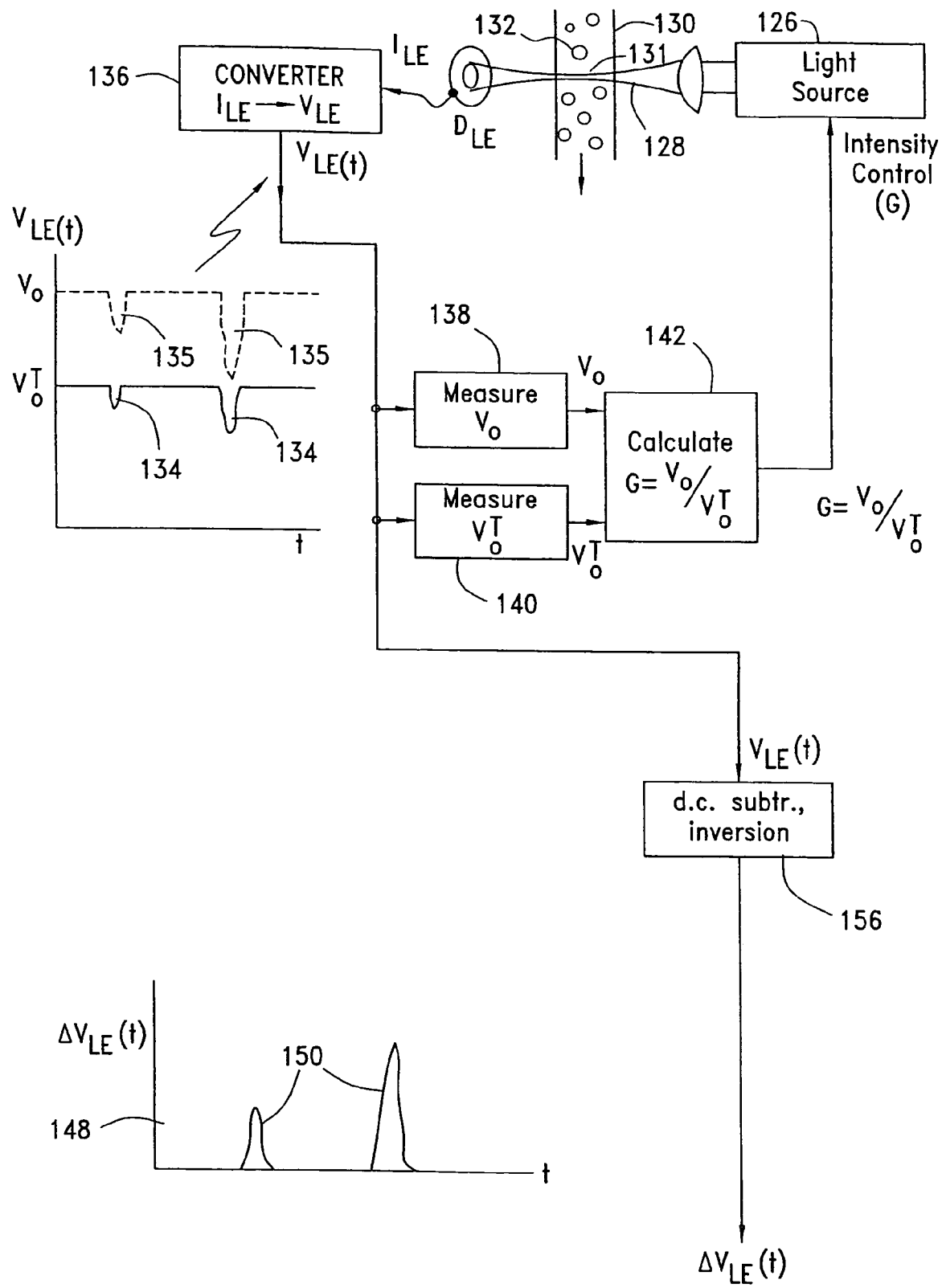

Each of these electronic schemes for raising $V^T_0$ up to $V_0$ effectively constitutes an automatic gain control, or AGC, system, that compensates either once (before data collection) or continuously (during data collection) for changes in the baseline level due to changes in sample turbidity. Then, data can be collected and analyzed using the desired deconvolution algorithm and related procedures, as discussed above. The resulting PHD will be substantially accurate, without the shifts to lower diameters that would otherwise result from the turbidity. (This conclusion assumes that the turbidity is not excessive, resulting in nonlinear response.) There is a third method, related to the second one discussed above, that, in principle, can be used to restore the baseline level to the value that it would have in the absence of turbidity. Rather than increasing the output signal using an amplifier means with an adjustable gain, the intensity of the light source means can be increased by the same desired factor, $V_0/V^T_0$. This method assumes that the light source means is normally operating at less than half of its available output power, allowing for increases of ×2, or greater, as needed. This method is shown in FIG. 26C in which the intensity of the light beam provided by light source 126 is controlled by control factor G. The output signal $V_{LE}(t)$ from converter 136 is then directly connected to be processed at 156 where the d.c. component is subtracted and the pulses are inverted. The output pulses 150 are again properly sized.

The second method of restoring the baseline level to $V_0$ before data collection was utilized for the measurements of the 0.05% fat emulsion samples (plain and spiked), summarized in FIGS. 21A, B, C through 23A, B, C. The uncorrected measured baseline level, $V^T_0$, was 4.82 volts, compared to $V_0$=5.00 volts without turbidity. From Equation 11 and x=0.02 cm, one obtains α=1.83 cm$^{-1}$. In the case of the 0.5% fat emulsion sample shown in FIGS. 24A, B, C and 25A, B, C, the measured value of 3.45 volts for $V^T_0$ implies α=18.55 cm$^{-1}$, which should theoretically be 10× larger than the value of α obtained for the 10× less concentrated sample. Indeed, there is close agreement. The small discrepancy may be ascribed to experimental error or departure from Beer's Law due to the onset of multiple scattering.

Figure 27A:
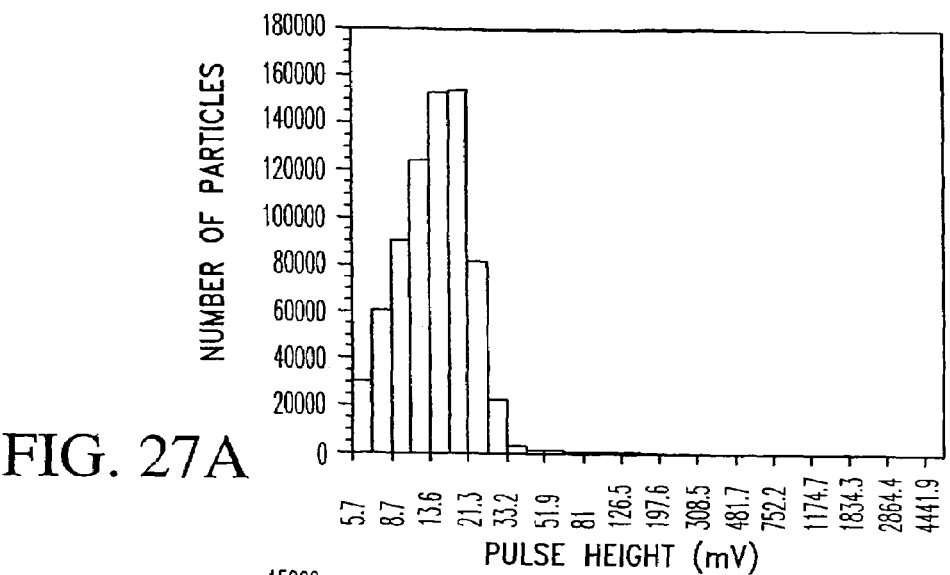
FIG. 27A shows the measured PHD (32-channels) obtained for an aqueous slurry of silica (fully concentrated) used for CMP processing.

FIGS. 27A, B, C and 28A, B, C summarize the results (32-channel resolution) obtained using the new LE-type sensor for another colloidal suspension—an aqueous slurry of silica, 12.5% (vol.) concentration, used for CMP processing. Each sample was measured without dilution, made possible because the refractive index of the silica is relatively close to the value for water. Even though the resulting turbidity was still significant, it was nevertheless much lower than the typical values obtained for suspensions of the same concentration containing particles much less matched in refractive index to the surrounding liquid.

Figure 27B:
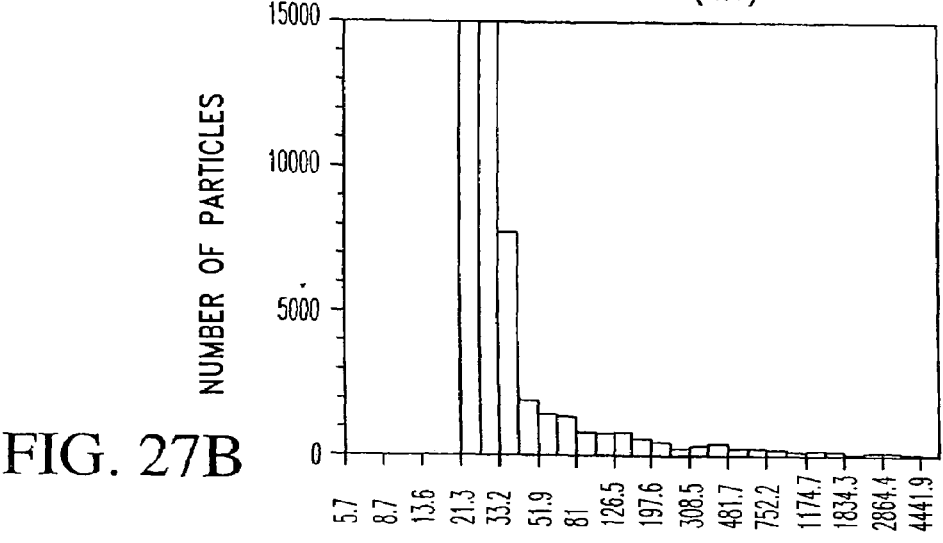
FIG. 27B shows the computed dPHD (successive subtraction, valid pulse-ht. region, expanded scale) obtained from the PHD in FIG. 27A.
Figure 27C:
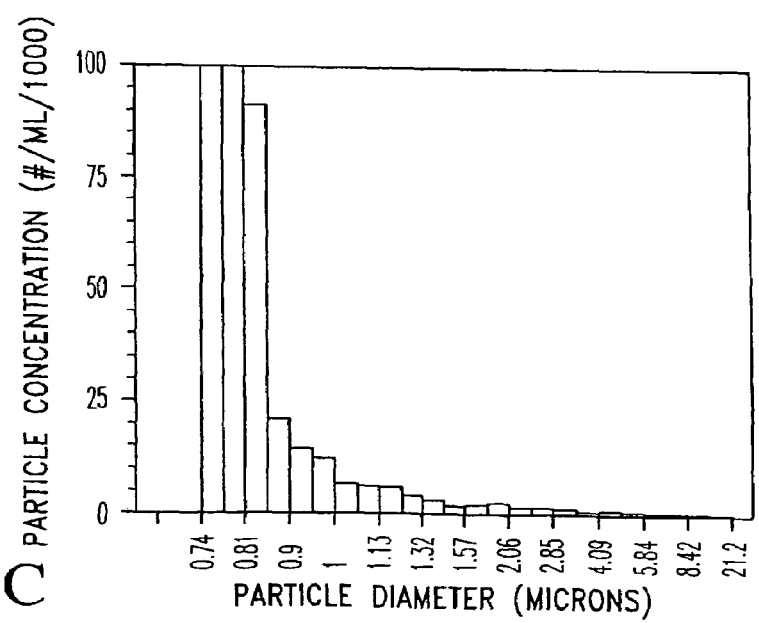
FIG. 27C shows the PSD (concentration, expanded scale) obtained from the computed dPHD in FIG. 27B, using the calibration curve (FIG. 8A) and sensor efficiency (FIG. 9)

The measured PHD for the fully concentrated silica CMP slurry is shown in FIG. 27A. The resulting dPHD (obtained by successive subtraction deconvolution) in the reliable pulse-height range is shown in FIG. 27B (expanded y-axis). The resulting PSD, expressed as the particle concentration in the original sample suspension, is shown in FIG. 27C. The y-axis is expanded 20-fold to accentuate the relatively low concentration of particles that populate the PSD tail.

Figure 28A:
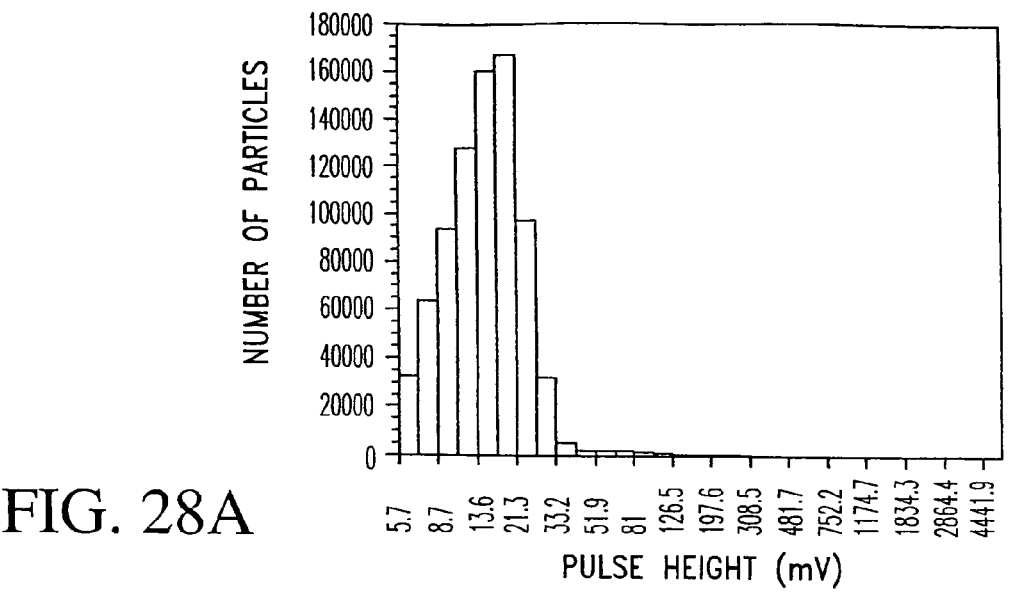
FIG. 28A shows the measured PHD (32-channels) obtained for the same silica slurry sample used in FIG. 27A, but with an added, low-concentration "spike" of 0.993-μm latex particles ($1.30 \times 10^5$/ml)
Figure 28B:
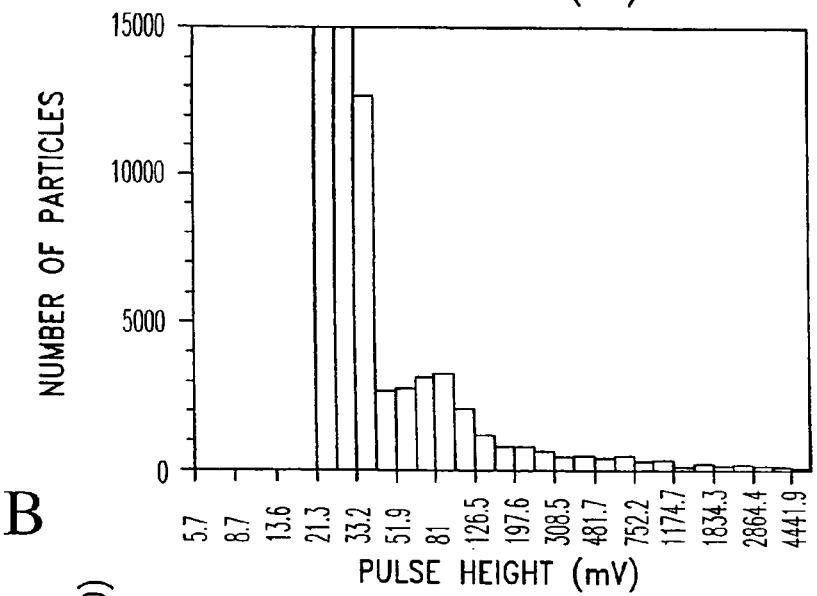
FIG. 28B shows the computed DPHD (successive subtraction, expanded scale) obtained from the PHD in FIG. 28A.
Figure 28C:
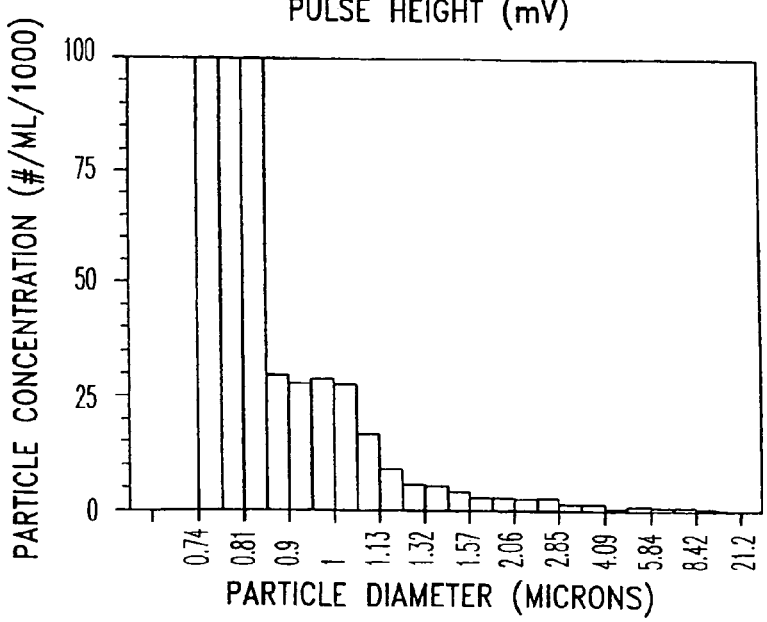
FIG. 28C shows the PSD (concentration, expanded scale) obtained from the computed dPHD in FIG. 28B, using the calibration curve (FIG. 8A) and sensor efficiency FIG. 9)

The same starting silica slurry was then spiked with a very low concentration of 0.993-μm latex particles—1.30×10$^5$/ml. The measured PHD is shown in FIG. 28A and the resulting DPHD is shown in FIG. 28B, where the effect of the latex perturbation is clearly evident. The final concentration PSD is shown in FIG. 28C. The added latex particles are easily detected. This is an impressive accomplishment for the new LE-type sensor, given the fact that this added latex spike represents only approximately 0.5 ppm of the total particle volume. Hence, this method possesses more than enough sensitivity to permit reliable, quantitative detection of outlier particle populations in silica-base CMP slurries caused by a variety of physical and chemical stress factors. Such increases in potentially damaging over-size particles are frequently correlated with increases in defects on wafer surfaces during CMP processing, resulting in lower yields of usable integrated circuit devices. The ability to monitor the "health" of potentially unstable CMP slurries during processing, with sensitivity to very small changes in the concentration of problematic particles, with little or no dilution required, represents a significant advance in CMP slurry metrology.

TABLE I

| Particle Diameter | Dilution/Concentration | Counts/16-ml | Maximum Pulse Ht, $^M\Delta V_{LE}$ |
|---|---|---|---|
| 0.806 μm ("A") | 800,000:1 of 10% (wt) | 37,870 | 33 mV (0.66% of 5 V) |
| 0.993 μm ("B") | 40,000:1 of 1% (wt) | 73,377 | 81 mV (1.62%) |
| 1.361 μm ("C") | 20,000:1 of 1% (wt) | 56,815 | 221 mV (4.42%) |
| 1.588 μm ("D") | 10,000:1 of 1% (wt) | 83,702 | 326 mV (6.52%) |
| 2.013 μm ("E") | 2,000:1 of 0.45% (wt) | 83,481 | 482 mV (9.64%) |
| 5.030 μm ("F") | 100:1 of 0.3% (wt) | 97,983 | 1552 mV (31.0%) |
| 10.15 μm ("G") | 40:1 of 0.2% (wt) | 31,423 | 3385 mV (67.7%) |
| 20.00 μm ("H") | 20:1 of 0.3% (wt) | 14,833 | 4473 mV (89.5%) |

TABLE II

| Latex Concentration (# Particles/ml) - Computed PSD vs Expected Values (*) | | | | | | |
|---|---|---|---|---|---|---|
| | 0.993-μm Peak | | 1.361-μm Peak | | 1.588-μm Peak | |
| Sample | PSD | Expected | PSD | Expected | PSD | Expected |
| A | 318 | 325 | 165 | 177 | 242 | 272 |
| B | 168 | 163 | 190 | 177 | 252 | 272 |
| C | 67 | 81 | 187 | 177 | 272 | 272 |

Figure 29:
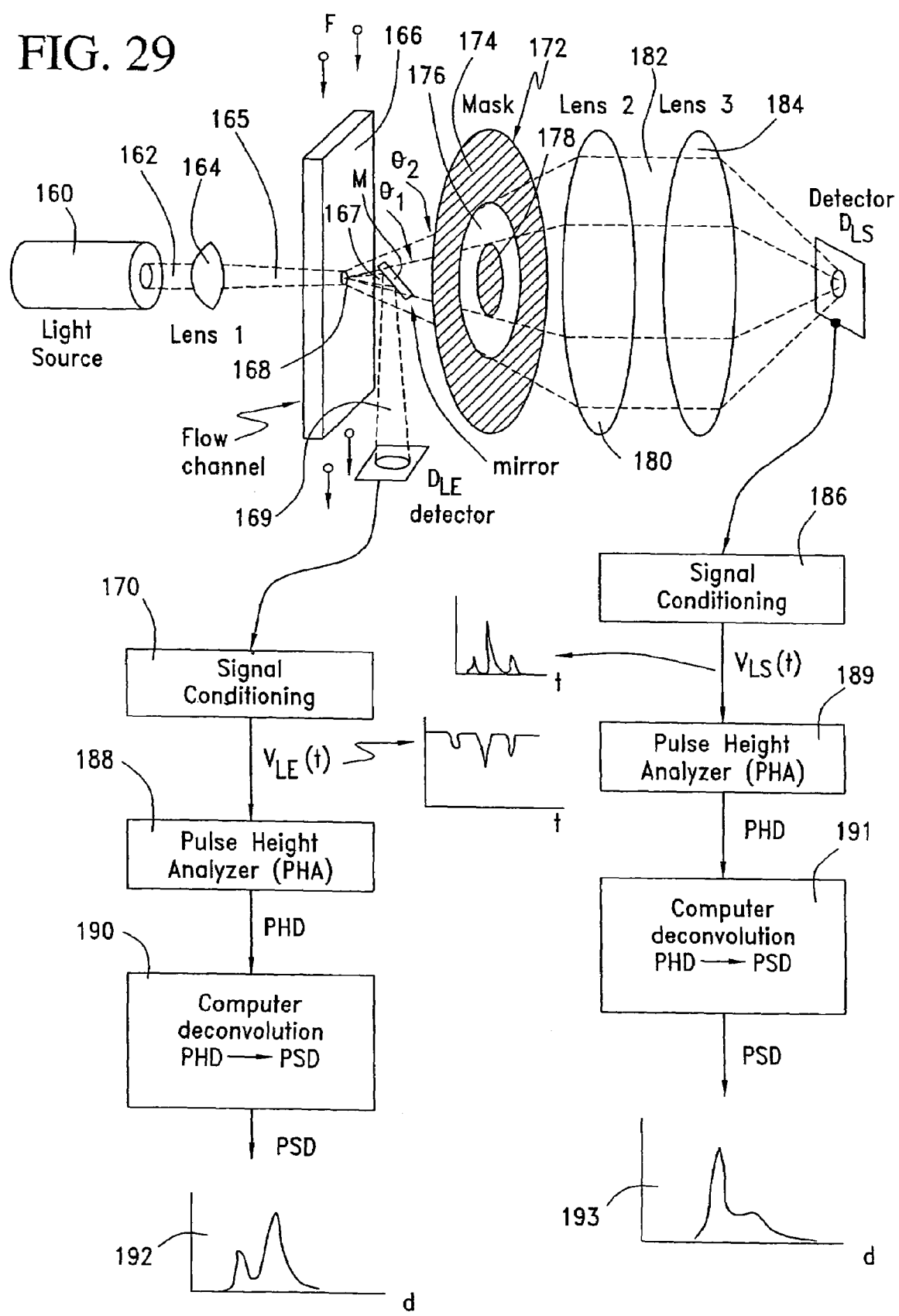
FIG. 29 is a block diagram showing the first, preferred embodiment of the invention.

A first preferred embodiment of the invention, shown schematically in FIG. 29, incorporates both the new LE- and LS-type SPOS sensors of the invention in a single sensor, having two independent output signals, $V_{LE}$ and $V_{LS}$. The resulting dual "LE+LS" design offers increased capability and flexibility, providing single-particle counting and sizing over a relatively large range of particle sizes. The LS-type sensor subsystem can be used to extend the size range below the lower detection limit provided by the new LE-type sensor subsystem. The extent to which the lower particle size limit can be extended depends on a variety of parameters. These include: the width, $2w$, of the narrow (typically focused) beam within the measurement flow cell; the power of the light source; the range of angles over which scattered light is collected for implementation of the new LS-type sensing function; and the physical properties, including the refractive index, of both the particles and the suspending fluid.

The new dual LE+LS sensor includes a light source 160, preferably consisting of a laser diode module, typically having an output wavelength in the range of 600 to 1100 nanometers (nm). The beam 162 produced by the light source means preferably is collimated (parallel) and "circularized"—i.e. the intensity is a function only of the distance, r, from the central axis. Furthermore, the beam preferably has a gaussian intensity profile, as described by Equation 7, along any axis normal to the axis of propagation of the beam. The new LE+LS sensor also includes a focusing means 164, typically a single- or multi-element lens, capable of focusing the starting collimated light beam 162 to the desired beam width, $2w$, at the center of the measurement flow channel 166 in the OSZ 168, consistent with the desired particle size range. It is assumed that the focusing means has an appropriate focal length, thus yielding acceptable values for both the width and depth of field of the focused beam. The latter is preferably significantly longer than the thickness, b, of the flow channel, in order to optimize the resolution of the resulting PSD.

The measurement flow cell 166 is fabricated from a suitable transparent material, such as glass, quartz or sapphire, or alternative semi-transparent material, such as PTFE (e.g. Teflon™, manufactured by DuPont) or other suitable plastic that is sufficiently transparent at the operating wavelength and compatible with the fluid-particle mixture. A suitable fluidics system, including a flow pump means and optional means for automatic dilution of the starting sample suspension (if needed), are typically required to facilitate the steady flow of the particle-fluid suspension through flow cell 166. The flow rate, F, is usually chosen to be the same as, or close to, the value used to generate the calibration curve for the LE- or LS-type sensor.

The thickness, b, of the flow channel should be small enough to achieve a high coincidence concentration limit and as uniform a beam width as possible (ideally with b<<depth of field), resulting in improved resolution for the final PSD. However, it must be large enough to prevent frequent clogging by over-size particles (e.g. agglomerated primaries and contaminants in the fluid/diluent). The width, a, of the flow channel is also chosen to strike a compromise between two competing effects. A relatively large value reduces the impedance to the flowing fluid-particle mixture and lowers the velocity (and increases the pulse width) for a given flow rate, F. However, the larger parameter a, the smaller the sensor efficiency, $\phi_d$, for any given particle diameter, d. This results in a smaller fraction of particles in the sample actually contributing to the measured PHD and final PSD, which, if too small, may be undesirable.

The new LE+LS sensor contains two separate light collection and detection subsystems, used independently to extract the desired LE- and LS-type signals. The LE-type signal can be captured using a small light reflecting means M (e.g. mirror), positioned so as to intercept the narrow beam 167 of incident light after it passes through the flow cell and fluid-particle mixture. The resulting transmitted beam 169, thus deflected away from the optical axis of the combined sensor, is caused to impinge on a nearby light detection means $D_{LE}$. The latter typically consists of a small-area, solid-state (silicon) detector, operating in a linear region and having a spectral response that is matched to the wavelength of light source 160, thus providing an output signal with an acceptable signal/noise (S/N) ratio. The output of the detector means is typically a current (the "photocurrent"), which can be conditioned by a current-to-voltage converter ("transimpedance" amplifier) 170, yielding an output signal in the generally desired form of a time-varying voltage, $V_{LE}(t)$, shown schematically in FIG. 2.

Alternatively, a small detector element can be placed directly in the path of the light beam 167 after it emerges from the flow cell, thus eliminating the need for the intermediate light reflecting means discussed above. Regardless of whether a mirror or detector element is used to "capture" the transmitted light beam, there are two requirements. First, the means used must function as an effective beam "stop." That is, it must be able to prevent any significant fraction of the arriving light flux from being reflected back toward the flow cell, thus becoming a source of "stray" light. Through unintended internal reflections from the various optical surfaces, a portion of the stray light can find its way to the scattering detection means $D_{LS}$, thus corrupting the resulting LS signal, by contributing a portion of the incident intensity to the latter. Second, the means used to capture the LE signal must be small enough not to intercept, and therefore block, scattered light rays at any angles that are intended to be captured and redirected to the light detection means $D_{LS}$, as discussed below.

Separately, scattered light originating from particles passing through OSZ 168 is collected over a range of scattering angles, $\theta$, with $\theta_1 < \theta < \theta_2$, where angles $\theta_1$ and $\theta_2$ are defined by a suitable aperture means, such as an annular mask 172 fabricated from a photographic negative with an outer opaque portion 174, a transparent intermediate portion 176, and an inner opaque portion 178. The scattered rays selected by mask 172 are allowed to impinge on a collecting lens 180 of appropriate focal length and location, which converts the diverging scattered rays into an approximately parallel beam 182. A second lens 184 is then typically used to refocus the rays onto a relatively small light detection means $D_{LS}$. As in the case of the LE subsystem, the output signal of $D_{LS}$ is typically a current, which can be optionally conditioned, typically by means of a transimpedance amplifier 186, so that the final output is in the form of a time-varying voltage, $V_{LS}(t)$, shown schematically in FIG. 12.

The signals $V_{LE}(t)$ and $V_{LS}(t)$ are organized into respective pulse height distributions PHD by pulse height analyzers 188 and 189. The PHDs are then respectively deconvoluted in computer deconvolution means 190 and 191, which ultimately compute a pair of respective particle size distributions PSD 192 and 193.

As should be obvious, this embodiment can be implemented as an LE-type or LS-type sensor only, simply by removing (or not installing in the first place) the optical elements, detection means and signal conditioning circuitry associated with the unwanted subsystem. In this case, it may be useful to adjust the width, $2w$, of the focused beam within the measurement flow channel, in order to optimize the resulting performance of the LE- or LS-type sensor. This parameter will impact the usable particle size range, coincidence concentration limit and minimum detectable particle size differently for the two sensing modes, as discussed earlier.

Figure 30:
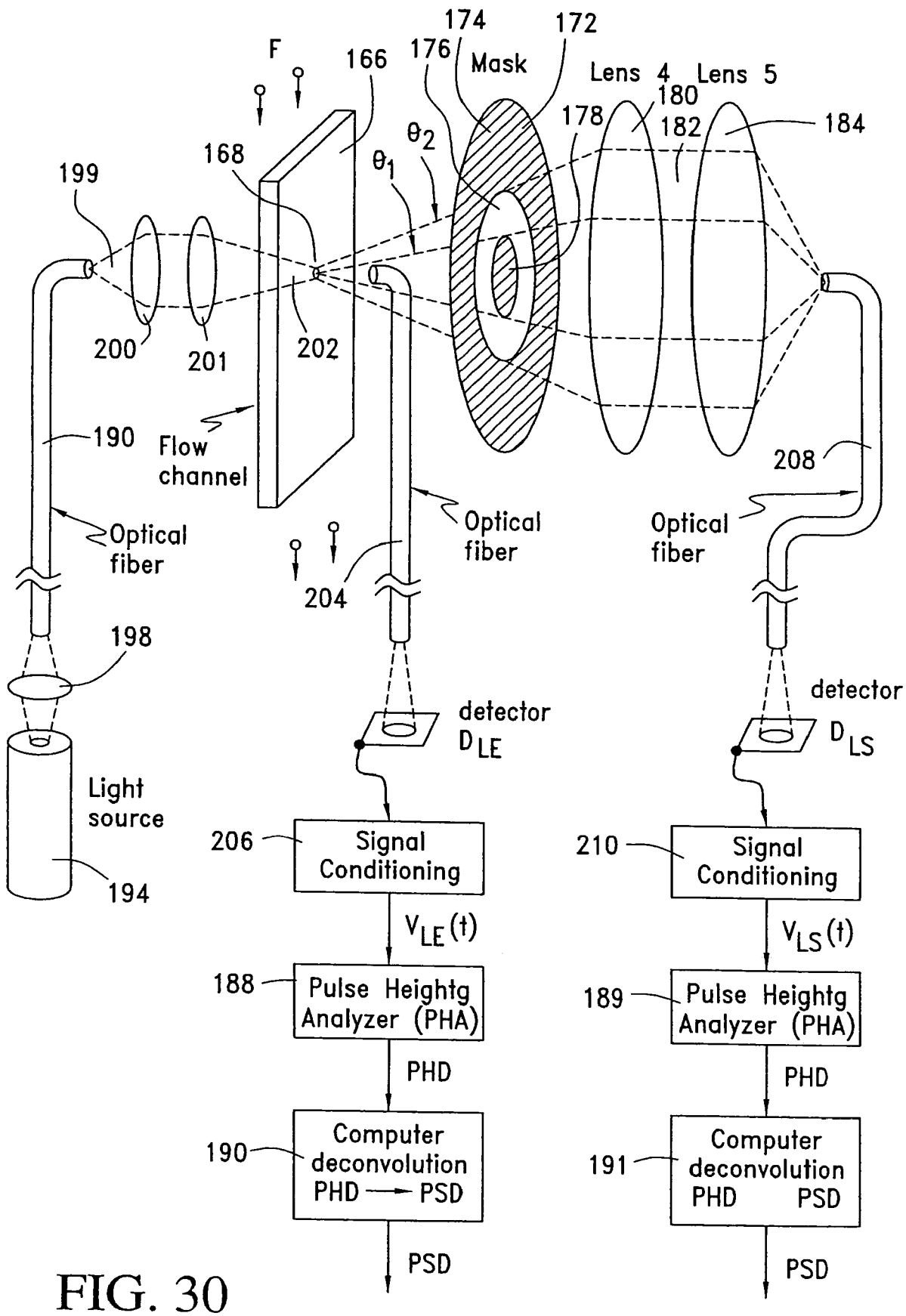
FIG. 30 is a block diagram showing the second embodiment of the invention.

A second embodiment is shown schematically in FIG. 30. For greatest capability and flexibility it also incorporates both LE- and LS-type subsystems. However, as in the case of the first embodiment, only those components that are needed for one or the other subsystem need be provided, if desired. The main difference between this embodiment and the embodiment of FIG. 29 concerns the use of optical fibers to convey light from a remote light source 194 into the sensor and to transmit the captured LE and LS light "signals" from the sensor to remote light detection means, similarly located outside the sensor. The main attribute of this design is the absence of electronic components or associated circuitry physically within the sensor proper. Consequently, a sensor based on this design requires no electrical power at the site of the sensor and is, by definition, immune to electrical interference, including stray electromagnetic radiation, which may exist in the immediate vicinity of use.

As shown in FIG. 30, an optical fiber 190 is used to carry light from an external light source 194 to within the sensor housing. It is useful, although not necessary, to use a single-mode (rather than a multi-mode) optical fiber for this purpose. When used in conjunction with a remote laser diode light source 194 (which, together with a suitable lens 198, launches light into the input end of fiber 190), this type of fiber acts usefully as an optical "spatial filter," or waveguide. By being able to support only a single mode of optical radiation, this fiber delivers a spatially "clean," circular beam 199 at its output end, having the desired gaussian intensity profile. Through the use of simple optics—e.g. two focusing lenses 200 and 201, as shown in FIG. 30—the diverging conical light beam is ultimately focused within measurement flow channel 166 into a narrow beam 202 with the desired final width, $2w$, as discussed above.

Optical fiber 204 is used to capture the focused light beam transmitted through the flow cell, conveying it to light detection means DLE, connected to signal conditioning circuitry 206, both of which are located outside the sensor. Optical fiber 208 is used to capture scattered light rays originating from OSZ 168 over a range of scattering angles, optionally using optical elements similar to those used to implement the LS subsystem in the first embodiment, including mask 172 with opaque portions 174 and 178, transparent portion 176, and lenses 180 and 184. The captured scattered light is conveyed to separate light detection means $D_{LS}$, connected to signal conditioning means 210, both of which are also located outside the sensor. Optical fibers 204 and 208 are typically chosen to be multimodal. The property of spatial filtering that is usefully provided by a single-mode fiber, such as fiber 190, for light input is typically not useful for light collection. Multimodal fibers are available with much larger cores, thus making it easier to capture all of the light rays of interest, thereby facilitating the optical alignment of both the LE and LS detection subsystems. The signals $V_{LE}(t)$ and $V_{LS}(t)$ provided by signal conditioning means 206 and 210 are analyzed at PHAs 188 and 189 and deconvoluted at 190 and 191 to provide respective PSDs.

As indicated, the embodiment of FIG. 30 yields a sensor that is electrically passive. Consequently, this design is potentially useful for particle sizing applications in challenging environments, often encountered in "online" process monitoring. One such example involves explosive environments. A sensor based on the embodiment of FIG. 30 would eliminate the need for a cumbersome and expensive explosion-proof enclosure (including an inert gas purging system) at the point of use/installation of the sensor. Another example is an environment containing high levels of electromagnetic radiation or electrical power-line noise, resulting in susceptibility of electronic circuitry to induced noise. Through the use of this embodiment of FIG. 30, the light source and detection means can be located in a remote area, where the electrical environment is quieter and the need for electrical shielding less demanding.

Another advantage of this embodiment is reduced complexity, and therefore cost. This may constitute a significant advantage in applications that require numerous sensors at different locations, where ease of replacement and service may be an important consideration. Apart from the possible need to replace a flow cell, because of damage to the inner surfaces due to particle contamination (coating) and/or solvent-related etching, there is no other component that would require replacing. Rather, the unpredictable, time-consuming and costly service associated with replacement of laser diode sources and repair of electronic circuitry (associated with the light detection means) would be performed at a central location. Environmental challenges at the point of use of the sensors, including temperature and humidity extremes, hazardous/explosive atmospheres and difficulty of access, can presumably be reduced or avoided altogether by performing most sensor service functions at a centralized, optimized location.

Figure 31:
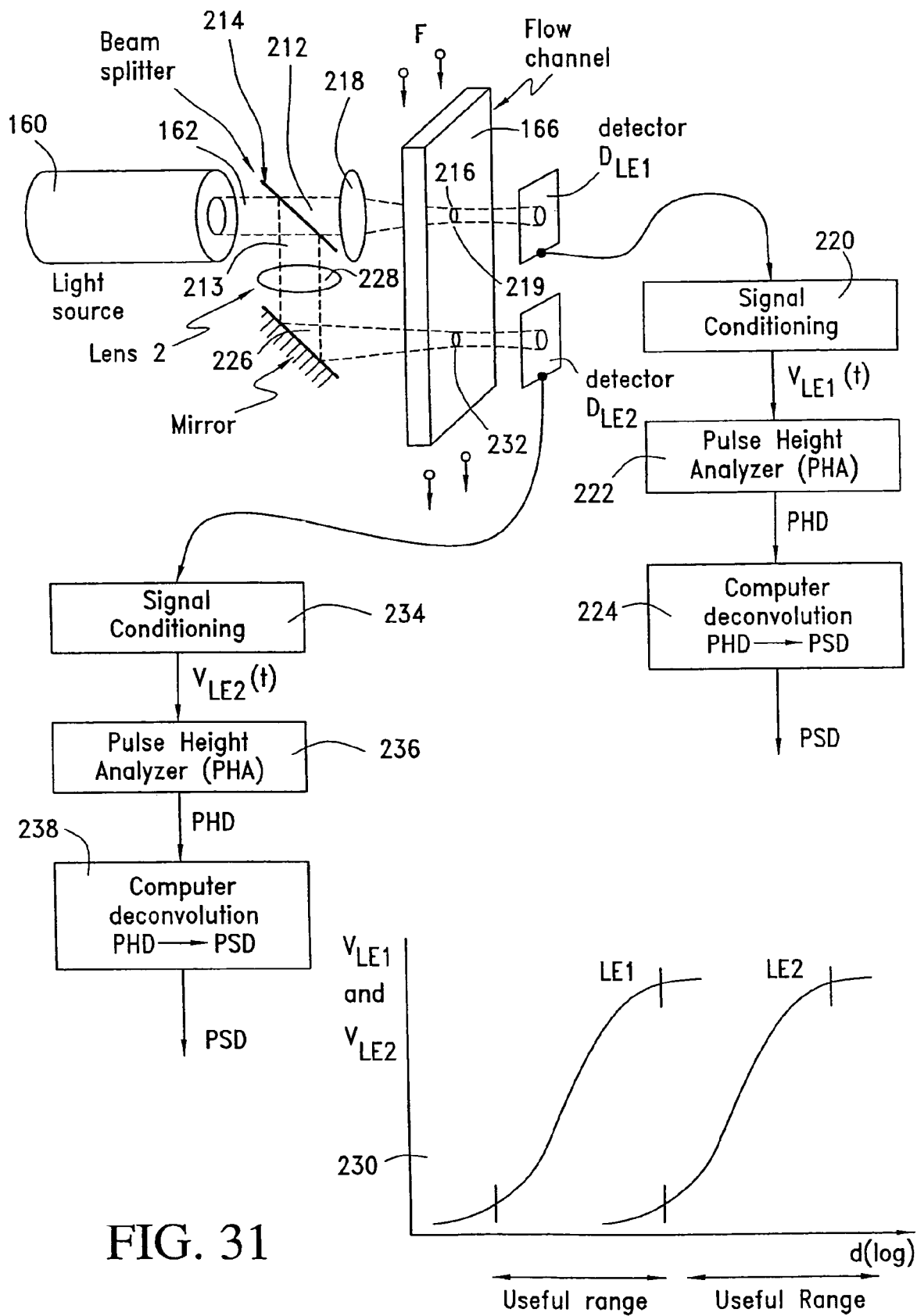
FIG. 31 is a block diagram showing the third embodiment of the invention.

A third embodiment, shown schematically in FIG. 31, incorporates two variations of the LE-type sensing apparatus of the invention within the same physical sensor. This new "dual LE-type" sensor includes the familiar light source 160—typically the same kind of laser diode module utilized in the embodiment of FIG. 29, producing a collimated, circular beam 162 with a gaussian intensity profile. (Alternatively, the starting light beam can be delivered by optical fiber from an outside light source means, as envisioned in the embodiment of FIG. 30.) This light beam is divided into two beams 212 and 213 of approximately equal intensity, by a beam splitter means 214. (An intensity ratio ranging from 50/50 to 60/40, or even 70/30, is typically acceptable.)

The portion of the original light beam passing through beam splitter 214 is reduced in width at 216 to the desired value, $2w_1$, at the center of measurement flow channel 166. It passes through a first OSZ 219 using an appropriate focusing means 218, which is typically a single- or multi-element lens, similar to the means used in the embodiment of FIG. 29. After this beam passes through the flow cell, it is caused to impinge on a light detection means $D_{LE1}$, typically consisting of a small silicon photodiode. The resulting photocurrent signal is conditioned at 220, typically using a transimpedance amplifier, so as to yield the desired time-varying LE-type signal, $V_{LE1}(t)$. (Alternatively, an optical fiber can be used to capture the transmitted light flux and deliver it to a remote light detection means, as envisioned in the second embodiment.) Signal $V_{LE1}(t)$ is analyzed at 222 to form the PHD and deconvoluted at 224, ultimately to form the desired PSD.

As discussed above in connection with FIGS. 8A and 10, for any given beam width there is a range of particle diameters over which there is acceptable sensitivity in the response—i.e. a significant change in the maximum pulse height, $^M\Delta V_{LE}$, with a small change in particle diameter, d. For a beam width of 10-11 μm, discussed extensively above, acceptable sensitivity and resolution are obtained over the approximate size range of 1 to 20 μm—i.e. from one-tenth to twice the beam width, or $(0.1-2)\times(2w_1)$.

Therefore, it is useful to provide a second LE-type measurement within the same sensor, for which the low-size end of its effective sizing range begins approximately where the high-size end of the first new LE subsystem terminates—e.g. 20 μm, using the example above. This can be accomplished if the beam width, $2w_2$, established in the flow channel by the second LE-type subsystem obeys the approximate relationship, $2\times(2w_1)\approx 0.1\times(2w_2)$, or $(2w_2)\ 20\times(2w_1)$. Using the example above, this implies a width of 200 μm for the second focused beam, yielding an effective size range for the second LE-type subsystem of approximately 20 to 400 μm.

The second LE-type subsystem is easily implemented, as indicated in FIG. 31. The portion 213 of the original light beam deflected by beam splitter 214 is redirected toward the flow cell using a mirror 226, appropriately oriented. Beam 213 is reduced in width to the desired value, $2w_2$, within the flow channel using an appropriate focusing means 228. The focal length and location of the latter will obviously be different than the corresponding parameters required for focusing beam 212. Alternatively, beam 213 may be passed directly through the flow channel without the use of a focusing means, provided that its width is already close to the desired value for the second LE-type subsystem. The second beam 213 is directed through a second OSZ 232 in measurement flow channel 166 to a second photo detector $D_{LE2}$. The signal is conditioned at 234 to provide signal $V_{LE2}(t)$ which is analyzed at 236, forming the PHD, which, in turn, is deconvoluted at 238, ultimately to produce the desired PSD.

The inset plot 230 in FIG. 31 shows schematically the relationship between the sensor responses for the two LE-type subsystems—i.e. $^M\Delta V_{LE}$, vs d and $^{M\Delta V}_{LE2}$ vs d. Using the example discussed above, a wide range of particle diameters can be analyzed by this dual LE-type subsystem—a conservative estimate is 1 to 400 μm.

The signals produced by the two new LE-type subsystems are independent of each other. In general, the PHDs produced by each subsystem will have been generated by completely different particles. Provided that each PHD contains a statistically significant number of particle counts (i.e. in each pulse height channel), it is unimportant whether any or all of the particles detected by one subsystem are also detected by the other subsystem during an analysis measurement. If the axes of the two beams are perfectly "lined up" (i.e. have the same x-axis value), then all of the particles that pass through the OSZ defined by the first beam should also pass through the OSZ defined by the second beam, given that it is larger. In practice it may be necessary to collect data in two intervals—first, at a relatively high concentration for the smaller, first beam, and then again at a lower concentration for the larger, second beam, to avoid coincidence effects.

Figure 32A:
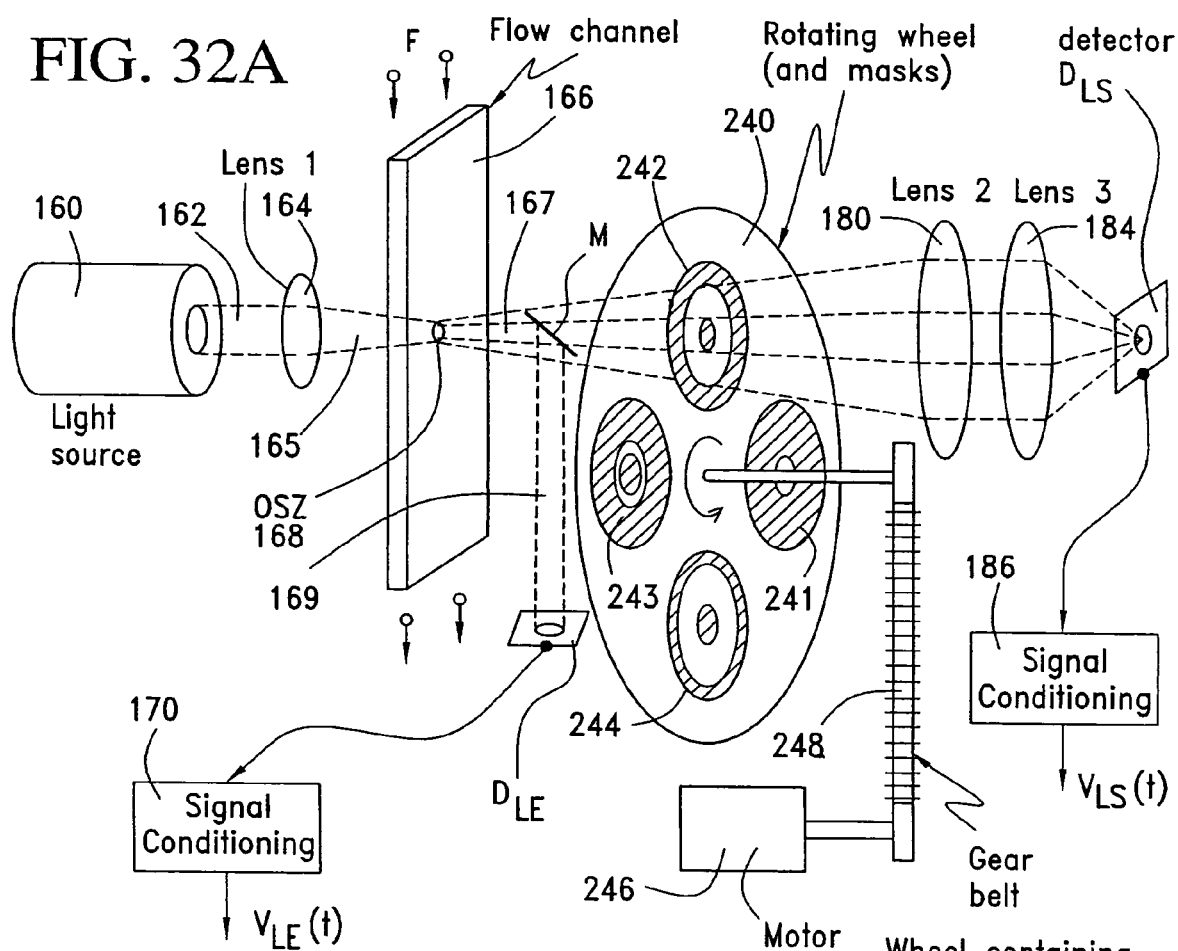
FIG. 32 is a block diagram showing the fourth embodiment of the invention.

A fourth embodiment is shown schematically in FIG. 32A. In addition to an optical LE-type sensor, it consists of a LS-type sensor of the invention that includes a means for selecting different ranges of angles over which scattered light is collected and directed onto a detection means DLs to obtain the desired LS signal, $V_{LS}(t)$. As discussed above, the scattered intensity is a strong function not only of the particle size, but also of the refractive indices of both the particle and the surrounding fluid. Proper selection of the range of angles permits the total intensity signal to be maximized, while avoiding "reversals" (non-monotonic behavior) in the response curve of integrated intensity vs particle diameter. Therefore, optimization of the sensor performance often requires a different angular range for each application (particle type) of interest.

As shown, the desired angular range is selected by rotating a wheel containing several different aperture masks 241, 242, 243, and 244. Each mask is designed to permit transmission of only those scattered rays that lie within the desired angular range, allowing them to reach the light-gathering lens. The wheel is rotated into one of several appropriate positions, each of which assures proper alignment of the desired mask—i.e. with its center on the optical axis defined by the incident beam and lenses. The wheel can be rotated manually to the desired position and then locked in place. Alternatively, a miniature motor 246 (e.g. stepper-type) and gear and belt system 248 can be used to position the desired mask automatically, by means of an electrical signal from the central control system of the sensor.

Figure 32B:
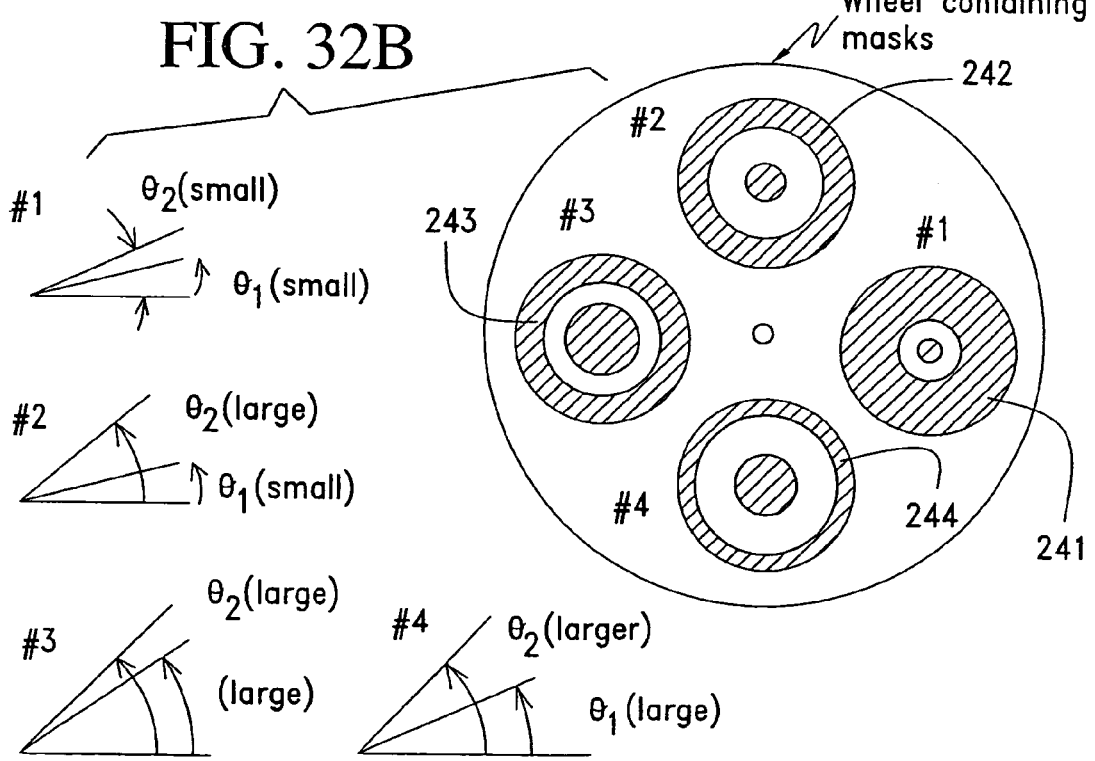

FIG. 32B shows an elevation view with the four masks 241-244 shown more clearly. The inset in FIG. 32B indicates four possible types of angular ranges that might be used, defined by the minimum and maximum angles of acceptance, $\theta_1$ and $\theta_2$, respectively. Mask 241 selects a narrow range of small angles θ i.e. both $\theta_1$ and $\theta_2$ relatively small. Mask 242 selects a wide range of angles—i.e. $\theta_1$ small and $\theta_2$ relatively large. Mask 243 selects a narrow range of relatively large angles—i.e. $\theta_1$ relatively large and $\theta_2$ only moderately larger. Mask 244 selects a wide range of relatively large angles—i.e. $\theta_1$ relatively large and $\theta_2$ substantially larger.

The other components shown in FIG. 32A are identical to the like numbered parts in the embodiment of FIG. 29.

In a variation of this embodiment, the rotating wheel in FIG. 32A can be replaced by a thin, rectangular-shaped plate, or card, fabricated from metal or plastic, that contains a single aperture mask. Insertion of the card into a properly located slot in the side of the sensor housing then brings the aperture mask into correct alignment between the flow cell and collecting lens. The desired angular range for measuring a particular sample can be selected by inserting the particular card containing the appropriate aperture mask for that sample. The calibration curve corresponding to the selected angular range is then used to obtain the PSD, following processing of the raw PHD data, as discussed above.

Alternatively, in another variation of this embodiment, the rotating wheel in FIG. 32B can be replaced by a single, adjustable annulus, consisting of an adjustable outer opaque iris, surrounding an adjustable inner opaque iris, having the same central axis. The annular region between the inner and outer opaque irises is transparent, allowing scattered light rays originating from the OSZ in the flow channel to reach the light collecting lens(es) and, ultimately, the LS detector means, $D_{LS}$. The range of scattering angles over which the scattered light rays are collected and contribute to the LS signal are defined by the inner and outer circumferences of the adjustable, transparent annulus. In one version of this, the annular region of acceptance can be adjusted using a mechanical device—e.g. two independently adjustable mechanical irises, similar to those used in cameras. In another version of this variation, the adjustable annulus can be realized using an electro-optical device, such as a two dimensional liquid-crystal display. By applying an appropriate voltage to two sets of contiguous, annular-shaped semi-transparent electrodes, an approximately transparent annular region can be defined between two opaque inner and outer regions. The desired range of scattering angles, θ, where $θ_1<θ<θ_2$, can be chosen by applying voltage to the sets of contiguous annular electrodes that define the regions which one desires to be opaque—i.e. $θ<θ_1$ and $θ>θ_2$.

Figure 33:
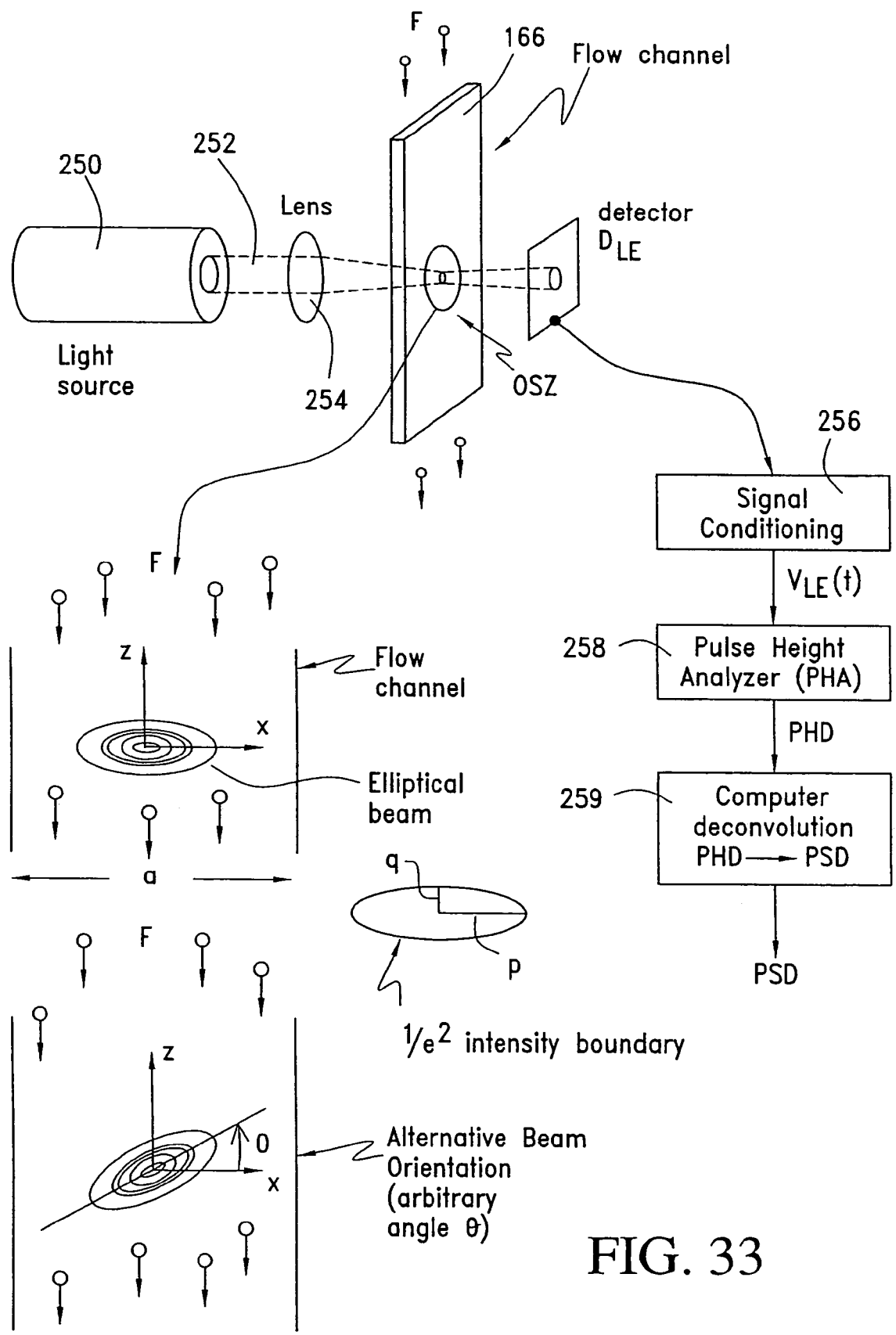
FIG. 33 is a block diagram showing the fifth embodiment of the invention.

A fifth embodiment is shown schematically in FIG. 33. Like the other embodiments, it may include either the new LE- or LS-type SPOS subsystem of this invention, or both, using a single light source and beam focusing means to define the OSZ. The distinguishing feature of the sixth embodiment is the use of a light beam with an elliptical gaussian intensity profile, rather than the circular gaussian profile used in the other embodiments. The resulting intensity profile of the focused beam in the flow channel is still described by Equation 7, but where the quantity $r^2/w^2$ is replaced by $(x/p)^2+(z/q)^2$, with p>q. Parameters p and q are, respectively, the semi-major and semi-minor axes of the elliptical-shaped imaginary surface of the beam, on which the intensity falls to $(1/e^2) \times I_0$, or $0.135\, I_0$, where $I_0$ is the intensity at the center of the beam (x=z=0). The "aspect" ratio of the resulting elliptical focused beam—the extent to which it is elongated—is defined as p/q. The elliptical beam becomes circular in the limiting case, where p/q=1.

An elliptical beam may be provided with the use of a laser-diode light source, which typically provides an elliptical light beam to begin with, before collimation. A beam of this shape may also be provided with a combination of cylindrical lenses or with the use of an aspherical lens. When an elliptical beam with a particular aspect ratio is required, it is possible to use a laser light source in combination with lenses of these types or to use such a combination to form a light source with an adjustable aspect ratio. Thus, light source 250 may be a laser light source which projects a beam with an appropriate aspect ratio or it may include a combination of cylindrical and/or aspherical lens to provide the required aspect ratio in an elliptical beam 252. A lens 254 then focuses the elliptical beam in the OSZ of measurement flow channel 166. Light from the OSZ then is detected by the photodetector DLE. The signal $V_{LE}(t)$ is then produced by conditioning the output signal at 256. This signal is analyzed in PHA 258 to provide the PHD, which is deconvoluted at 259 to ultimately produce the desired PSD.

As before, the focusing means causes the incident light beam to become reduced in cross-sectional size within the flow channel. The "width" of the resulting focused beam now has meaning only with respect to a particular chosen axis, normal to the axis of the beam. Whereas a single parameter, 2w, suffices to describe the width of a circular beam, two parameters—2p and 2q—are now required to describe an elliptical beam. The aspect ratio of the focused elliptical gaussian beam is the same as that of the original (collimated) beam before focusing. As shown in FIG. 33, the desired orientation of the focused elliptical beam within the flow channel is usually such that the major axis, of width 2p, is perpendicular to the direction of flow of the particles. This axis is also parallel to the x-axis, along the direction that defines the width, a, of the flow channel (FIG. 3). The minor axis of the focused beam, of width 2q, is parallel to the z-axis and the direction of flow.

There are several significant consequences of the change in beam shape, from circular to elliptical, causing the zone of illumination to extend further across the width, a, of the flow cell. First, the resulting OSZ also possesses an elliptical-shaped cross section. A given level of incident light intensity now extends further from the central axis (x=z=0) of the beam than it would for a circular beam. Therefore, a larger fraction of the particles flowing through the channel will cause the minimum necessary perturbation in the LE (or LS) signal to be detected, and thereby contribute to the measured PHD. Hence, the sensor efficiency, $φ_d$, corresponding to a given particle diameter, d, will increase relative to the value that would be obtained for a circular beam of width 2w, having the same total intensity (i.e. light flux), with 2p>2w. At first glance, it might appear that an increase in $φ_d$ represents an improvement in the performance of the sensor. However, this "gain" is accompanied by a decrease in the coincidence concentration limit of the sensor. If the major goal is maximization of the concentration at which the starting sample suspension can be measured, without further dilution, then an improvement in $φ_d$ achieved at the expense of degradation in the coincidence concentration probably results in a net disadvantage. One of the major defining characteristics of the new LE- or LS-type sensor of this invention is its ability to obtain relatively accurate and reproducible PSDs, regardless of the fact that only a relatively small fraction of the particles that pass through the sensor actually contributes to the measured result. All that is necessary is that a statistically significant number of particle counts are collected in each relevant pulse height channel.

A second consequence of the substitution of an elliptical beam for the normal circular one is that the sensitivity of the sensor is degraded to some extent. The cross-sectional area illuminated by the incident focused beam and therefore the cross-sectional area of the corresponding OSZ are increased by virtue of the elongation of the beam along the width of the flow channel. Thus, the fraction of the illuminated area that is effectively "blocked," in the light-extinction sense, by a particle of a given size is reduced, relative to the fraction blocked for a circular beam for which 2w=2q, but 2w<2p. Hence, the minimum detectable particle size threshold for the sensor will be higher than it would otherwise be for a circular beam.

A third consequence of the elliptical beam, by contrast, is advantageous. The resulting sensor will possess higher resolution—i.e. in principle the PHD will provide a "cleaner" distinction between particles of nearly the same size. There is now a longer region extending along the x-axis over which the incident intensity is nearly the same. This constitutes the "top" of the gaussian profile in intensity, extended in length along the major axis. Therefore, there is a larger set of trajectories, of differing |x| values, for which particles are exposed to a similar intensity as they pass through the OSZ. Therefore, the PHD response for uniform particles of a given size becomes "sharper." There is a larger fraction of particle counts in a narrow range of pulse heights immediately adjacent to, and including, the peak of the PHD, with the distribution falling more steeply to lower count values for pulse heights below the maximum cutoff value. The same, therefore, is true for the various basis vectors that are used for deconvolution of the PHD, resulting in higher resolution for the resulting dPHD and corresponding PSD. This last characteristic constitutes the only potential advantage of an elliptical-shaped beam, which may outweigh the accompanying disadvantages, noted above. The user must determine the net advantage or disadvantage, depending on the application.

It is useful to recognize the fact that an elliptical-shaped beam represents an intermediate step in the evolution from one "extreme" of sensor illumination to another. At one end of the sensor-design spectrum, introduced in the current invention, there is a "tight" circular beam of width $2w$, yielding the narrowest possible region of illumination and, consequently, producing the greatest non-uniformity of response. Different particle trajectories give rise to the largest range of pulse heights for particles of the same size, as discussed extensively above. There is a major disadvantage associated with this maximal-nonuniform illumination—i.e. the greatest possible ambiguity between pulse height and particle size, requiring the use of a deconvolution procedure to "recover" a reasonably reliable PSD from the measured PHD.

At the other end of the sensor-design spectrum, there is the traditional illumination scheme employed by a conventional LE- or LS-type sensor, reviewed earlier (FIG. 1), in which a thin "knife-edge" of incident light extends across the flow channel. Ideally, there is very little variation in incident intensity along the x-axis (e.g. at maximum intensity, z=0). The variation along the z-axis, for any given x-axis value, obeys a gaussian profile. In this other "extreme" case, the pulse heights produced by particles of a given size are ideally the same for all trajectories. Therefore, the measured PHD requires no deconvolution procedure, as it effectively is equivalent to the final desired PSD, apart from a calibration factor. This situation represents the most complete tradeoff in sensor characteristics, achieving the highest possible resolution in exchange for relatively poor sensitivity and dramatically lower coincidence concentration. This illumination scheme, utilized in conventional LE- or LS-type sensors, is conceptually achieved by employing an elliptical-shaped beam and "stretching" its major axis, so that p/q approaches ininity in the ideal limit. It should be clear that the choice of an elliptical-shaped beam of moderate aspect ratio—e.g. p/q=2 to 4—for use in a new LE- or LS-type sensor results in a compromise in sensor performance. Somewhat improved particle size resolution is obtained, at the expense of somewhat reduced sensitivity and coincidence concentration.

Figure 34:
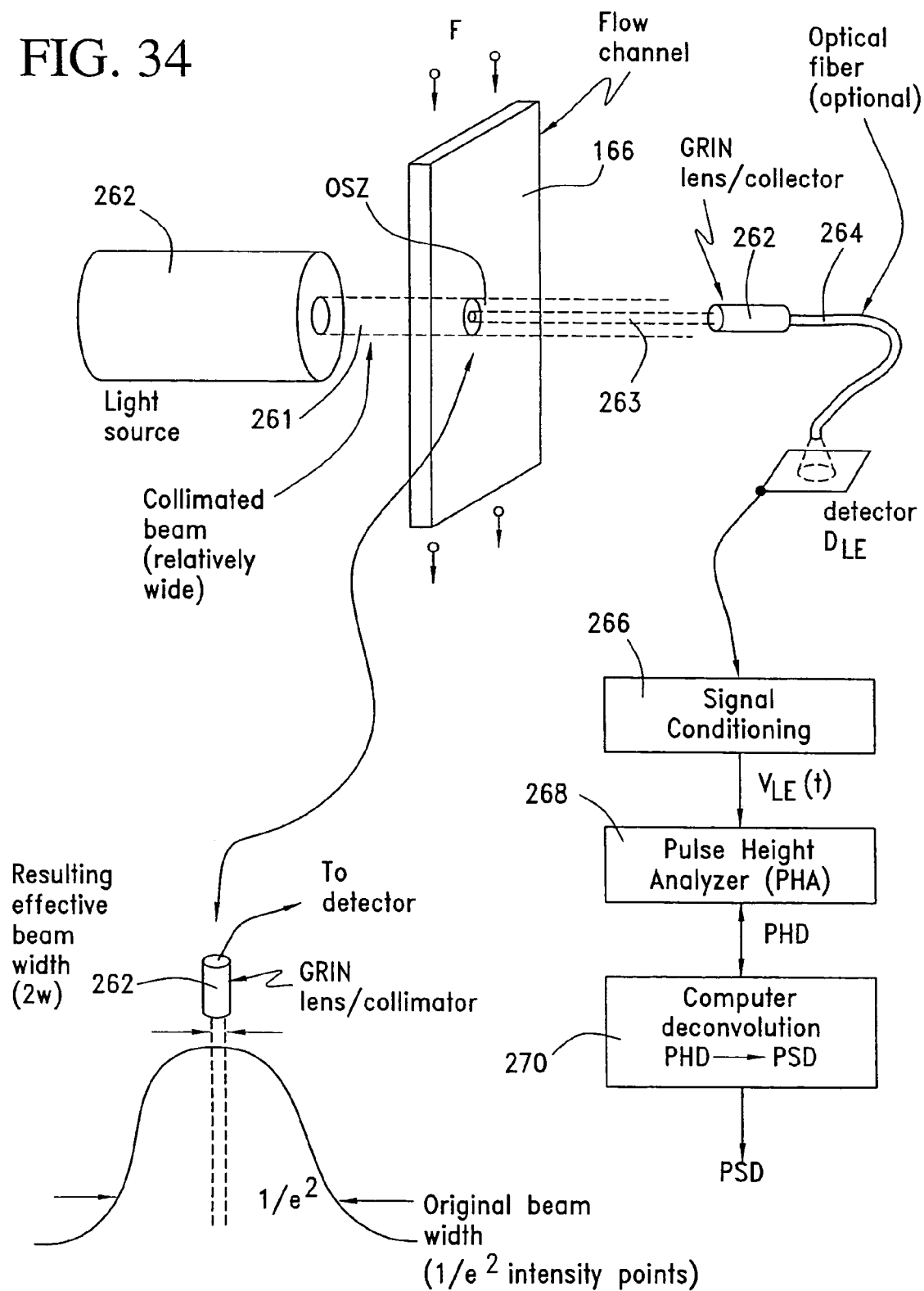
FIG. 34 is a block diagram showing the sixth embodiment of the invention.

A sixth embodiment of the new LE-type sensor is shown schematically in FIG. 34. A collimated, relatively wide starting beam 261 of light produced by a light source 262 is caused to pass through a flow channel 166 without the use of a focusing means, as employed in the other six embodiments. Typically, the effective width of the resulting cylindrical-shaped OSZ would be unacceptably large, yielding relatively poor sensitivity (i.e. a relatively high minimum diameter threshold) and relatively low coincidence concentration. A narrower, more acceptable effective width can be achieved for the OSZ through the use of a novel means for limiting the region from which transmitted light rays are allowed to contribute to the LE signal. This objective can be achieved through the use of special collimating optics on the "detection side" (as opposed to the light-source side) of the LE-type sensor design shown in FIG. 34.

For example, a specially designed graded-index ("GRIN") collimating lens 262, having a very narrow range of acceptance angles and an appropriately small aperture size can be utilized to capture a relatively small fraction of the total light flux transmitted through the flow channel. Typically, the output from GRIN collimating lens 262 can be conveniently conveyed by optical fiber 264 to a light-detection means $D_{LE}$ connected to appropriate signal conditioning circuitry 266, yielding the desired LE signal, $V_{LE}$, suitable for subsequent processing in PHA 268 and deconvolution at 270, as discussed extensively above. GRIN collimating lens 262, depending on its acceptance aperture, ideally captures only those light rays 263 that closely surround the central axis of incident beam 261, thus reducing the effective width of the resulting OSZ. In effect, GRIN element 262 captures only those rays that lie at or near the top of the gaussian intensity profile associated with incident (transmitted) light beam 261.

The intensity of illumination across the resulting OSZ is therefore relatively uniform, with a relatively sharp "cutoff" to nearly zero illumination outside the cylindrical region of acceptance defined by GRIN lens 262. As a result, the sensor efficiency, $\phi_d$, for a given particle diameter, d, will be smaller than it would otherwise be, given the relatively wide starting beam. This also results in a higher sensitivity to smaller particles and a higher coincidence concentration. In the present case, the OSZ more closely resembles a cylinder of uniform intensity over its cross section, with a "hard" imaginary surface, beyond which the intensity drops precipitously to zero. In principle, the resulting PHDs have higher, narrower peaks, because particles that pass through the OSZ give rise to pulses having more similar heights. The resulting PSDs therefore have better size resolution. An unavoidable disadvantage is relatively poor size resolution at the high end of the diameter scale, owing to the sharper cutoff ("hard" outer boundary) of the OSZ. The characteristics and performance of the resulting sensor, based on the simple scheme shown in FIG. 34, will depend on the detailed design specifications of GRIN lens 262.

Although the matrix used in the deconvolution of the PHD is shown-with basis vectors in vertical columns that increase in particle size from left to right and rows which extend horizontally across the matrix and increase in pulse height channel size from top to bottom, the matrix could be altered in various ways. For example, the column basis vectors could become row basis vectors, or the increase in particle size for the columns could increase from right to left. If row basis vectors are used, the particle size could increase from top to bottom or from bottom to top. Likewise, if pulse height columns are used, the pulse height channels could increase from left to right or from right to left. It should be observed as well that the column data source vector, containing the measured PHD, could be arranged as a row and/or the direction of increase could be in one direction or in the reverse direction. It is to be understood therefore that as used in this specification and in the claims it is intended that the terms "column" and "row" are interchangeable and that the directions of increase can be reversed.

While the invention has been particularly shown and described with reference to preferred embodiments thereof, it will be understood by those skilled in the art that the foregoing and other changes in form and detail may be made therein without departing from the spirit and scope of the invention.

The invention claimed is:

1. A method of compensating a single-particle optical sizing sensor for sizing particles in a relatively concentrated fluid suspension sample for turbidity of said suspension sample, said sensor operating on a light extinction principle whereby a photo-detector produces signal $V_{LE}(t)$ having a baseline voltage level and a response to blockage of light by a particle as a downwardly extending pulse from said baseline voltage level, said method comprising:

passing a non-turbid suspension through said sensor;

measuring a baseline voltage level $V_0$ produced in response to said non-turbid suspension;

passing said relatively concentrated suspension sample through said sensor;

measuring a baseline voltage $V_0^T$ produced in response to said relatively concentrated suspension sample;

calculating the ratio $$G = \frac{V_0}{V_0^T};$$

and adjusting said sensor in response to G to compensate for said turbidity when said relatively concentrated suspension sample passes through said sensor.

2. The method of claim 1, wherein said baseline voltage $V_0^T$ is effectively subtracted from said signal $V_{LE}(t)$, the remaining signal is inverted to produce a pulse height signal $\Delta V_{LE}^T(t)$, adjustable gain amplifying means is used to amplify said pulse height signal $\Delta V_{LE}^T(t)$, and said adjustable gain amplifying means is controlled by said ratio G to provide a compensated pulse height signal $\Delta V_{LE}(t)$.

3. The method of claim 1, wherein said signal $V_{LE}(t)$ produced by said sensor in response to said relatively concentrated suspension sample is amplified by adjustable gain amplifier means, the gain of which is controlled by said ratio G to provide a compensated signal $V_{LE}(t)$ having a compensated baseline voltage $V_0$, subtracting said baseline voltage $V_0$ from said compensated signal $V_{LE}(t)$, and inverting the remaining signal to produce compensated pulse height signal $\Delta V_{LE}(t)$.

4. The method of claim 1 wherein said single-particle optical sizing sensor comprises a light source producing a light beam of adjustable intensity, wherein said intensity is increased in response to said ratio G to compensate for said turbidity.

* * * * *